US010940171B2

(12) United States Patent
Shepherd et al.

(10) Patent No.: US 10,940,171 B2
(45) Date of Patent: Mar. 9, 2021

(54) MICROBIAL PRODUCTION OF PURE SINGLE STRANDED NUCLEIC ACIDS

(71) Applicant: Massachusetts Institute of Technology, Cambridge, MA (US)

(72) Inventors: Tyson Shepherd, Arlington, MA (US); Rebecca Du, Cambridge, MA (US); Mark Bathe, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 54 days.

(21) Appl. No.: 16/189,418

(22) Filed: Nov. 13, 2018

(65) Prior Publication Data

US 2019/0142882 A1 May 16, 2019

Related U.S. Application Data

(60) Provisional application No. 62/584,664, filed on Nov. 10, 2017.

(51) Int. Cl.
| | |
|---|---|
| *A61K 35/76* | (2015.01) |
| *C12N 15/86* | (2006.01) |
| *C12N 15/63* | (2006.01) |
| *A61K 47/69* | (2017.01) |
| *C07K 7/06* | (2006.01) |
| *C07K 14/005* | (2006.01) |
| *C12N 15/10* | (2006.01) |
| *C12N 15/11* | (2006.01) |
| *C12N 15/65* | (2006.01) |

(52) U.S. Cl.
CPC .......... *A61K 35/76* (2013.01); *A61K 47/6901* (2017.08); *C07K 7/06* (2013.01); *C07K 14/005* (2013.01); *C12N 15/1044* (2013.01); *C12N 15/1096* (2013.01); *C12N 15/11* (2013.01); *C12N 15/63* (2013.01); *C12N 15/65* (2013.01); *C12N 15/86* (2013.01); *C12N 2795/14122* (2013.01); *C12N 2795/14142* (2013.01); *C12N 2795/14143* (2013.01); *C12N 2810/60* (2013.01)

(58) Field of Classification Search
CPC ..................................................... A61K 35/76
See application file for complete search history.

(56) References Cited

U.S. PATENT DOCUMENTS

| | | |
|---|---|---|
| 4,816,567 A | 3/1989 | Cabilly |
| 5,356,802 A | 10/1994 | Chandrasegaran |
| 5,436,150 A | 7/1995 | Chandrasegaran |
| 5,487,994 A | 1/1996 | Chandrasegaran |
| 5,624,821 A | 4/1997 | Winter |
| 6,140,081 A | 10/2000 | Barbas |
| 6,194,551 B1 | 2/2001 | Idusogie |
| 6,453,242 B1 | 9/2002 | Eisenberg |
| 6,534,261 B1 | 3/2003 | Cox |
| 6,610,512 B1 | 8/2003 | Barbas |
| 6,746,838 B1 | 6/2004 | Choo |
| 6,866,997 B1 | 3/2005 | Choo |
| 7,067,617 B2 | 6/2006 | Barbas |
| 8,227,242 B2 | 7/2012 | Bradbury |
| 8,501,923 B2 | 8/2013 | Rothemund |
| 2002/0165356 A1 | 11/2002 | Barbas |
| 2003/0215914 A1 | 11/2003 | Houtzager |
| 2004/0180422 A1 | 9/2004 | Hoet |
| 2004/0197892 A1 | 10/2004 | Moore |
| 2005/0147962 A1 | 7/2005 | Wagstrom |
| 2007/0117109 A1 | 5/2007 | Rothemund |
| 2007/0128728 A1 | 6/2007 | Bradbury |
| 2007/0154989 A1 | 7/2007 | Barbas |
| 2007/0213269 A1 | 9/2007 | Barbas |
| 2012/0251583 A1 | 10/2012 | Rothemund |
| 2013/0295614 A1* | 11/2013 | Hareendran ........... C12N 15/86 435/91.4 |
| 2019/0203242 A1 | 7/2019 | Praetorius |

FOREIGN PATENT DOCUMENTS

| | | |
|---|---|---|
| CN | 106119269 | 11/2016 |
| WO | 9853059 | 11/1998 |
| WO | 9958572 | 11/1999 |
| WO | 2000071694 | 11/2000 |

(Continued)

OTHER PUBLICATIONS

Paul W. K. Rothemund. Folding DNA to create nanoscale shapes and patterns. 2006. Nature. vol. 440. 297-302. (Year: 2006).*
New England Biolabs: Catalog #N4040S (Year: 2007).*
Part:BBa_K1445000, 2014, Registry of Standard Biological Parts, Group: iGEM14_Cu-Boulder (Year: 2014).*
Li et al. Engineering nucleic acid structures for programmable molecular circuitry and intracellular biocomputation. 2017. Nature Chemistry. vol. 9. 1056-1067 (Year: 2017).*
Zhou et. al. A new biochromatography model based on DNA origami assembled PPARγ: construction and evaluation. 2017 Anal Bioanal Chem 409:3059-3065 (Year: 2017).*

(Continued)

*Primary Examiner* — Neil P Hammell
*Assistant Examiner* — Tiffany Nicole Grooms
(74) *Attorney, Agent, or Firm* — Pabst Patent Group LLP

(57) ABSTRACT

Methods and compositions for bacterial production of pure single-stranded DNA (ssDNA) composed of custom sequence and size have been developed. The methods enable scalability and bio-orthogonality in applications of scaffolded DNA origami, offering one-step purification of large quantities of pure ssDNA amendable for immediate folding of DNA nanoparticles. The methods produce pure ssDNA directly from bacteria. In some embodiments the *E. coli* helper strain M13cp combined with a phagemid carrying only an f1-origin allows for, without the need for additional purification from contaminating dsDNA. This system is useful for generalized circular ssDNA synthesis, and here is applied to the assembly of DNA nanoparticles folded both in vitro and direct from phage.

28 Claims, 14 Drawing Sheets

Specification includes a Sequence Listing.

(56) References Cited

FOREIGN PATENT DOCUMENTS

| WO | 2003016496 | 2/2003 | | |
|---|---|---|---|---|
| WO | WO-2004048543 A2 | * | 6/2004 | ............... C12N 7/00 |
| WO | 2007067818 | 6/2007 | | |
| WO | 2013176772 | 11/2013 | | |
| WO | 2014018423 | 6/2014 | | |
| WO | 2017089567 | 6/2017 | | |
| WO | 2017089570 | 6/2017 | | |
| WO | 2017189870 | 11/2017 | | |
| WO | 2017189914 | 11/2017 | | |

OTHER PUBLICATIONS

Nayak et. al. Cas9-mediated genome editing in the methanogenic archaeon Methanosarcina acetivorans. 2017. PNAS. 114(11) 2976-2981. (Year: 2017).*
Sattar et. al. Ff-nano, short functionalized nanorods derived from Ff (f1, fd, or M13) filamentous bacteriophage. 2015. Methods. 6(316) 1-13 (Year: 2015).*
SEQ ID No. 1-139 Alignment (Year: 2020).*
New England Biolabs: Catalog #N4018S (Year: 2007).*
Brown et. al. An easy-to-prepare mini-scaffold for DNA origami. 2015 Nanoscale. 7, 16621-1662 (Year: 2015).*
Abramoff, et al., "Image processing with ImageJ", Biophotonics Int., 11(2):36-42 (2004).
Ailenberg, et al., "An improved Huffman coding method for archiving text, images, and music characters in DNA", BioTechniques., 47:747-754 (2009).
Amunts, et al., "Ribosome. The structure of the human mitochondrial ribosome", Science., 348(6230):95-98 (2015).
Angal, et al., "A single amino acid substitution abolishes the heterogeneity of chimeric mouse/human (IgG4) antibody", Mol. Immunol., 30:105-08 (1993).
Anonymous, et al., "M13mp18 (Cloning Vector)", New England BioLabs Catalog, http://international.neb.com/-/media/nebus/page-images/tools/dna-sequences-and-maps/m13mp18_map.pdf?la=en&hash+ABF432A1085CFA7CA7850D00B69ACBE654DFC580( 2002).
Arita, et al., "Chapter 368: DNA Memory", Handbook of Natural Compu, 1281-1318 (2012).
Arizona State University, "Top-down design brings new DNA structures to life", retrieved from the internet: URL:https://phys.org/news/2016-05-top-down-dna-life.html :1-4 (2016).
Babaei, "A novel text and image encryption method based on chaos theory and DNA computing", Nat Comput., 12:101-107 (2013).
Bai, et al., "Cryo-EM structure of a 3D DNA-origami object", Proc. Natl. Acad. Sci. 109, 20012-20017 (2012).
Benson, et al., "Computer-Aided Production of Scaffolded DNA Nanostructures from Flat Sheet Meshes", Angewandte Chemie, 55(31):8869-8872 (2016).
Benson, et al., "DNA rendering of polyhedral meshes at the nanoscale", Nature, 523:441-444 (2015).
Benson, et al., "Supplementary Information to DNA rendering of polyhedral meshes at the nanoscale", Nature, 523(7561):441-444 (2015).
Bent, et al., "On non-intersecting Eulerian circuits", Discrete Appl. Math. 18(1):87-94 (1987).
Bhatia, et al., "Icosahedral DNA nanocapsules by modular assembly", Angew. Chem. Int. Ed., 48(23):4134-4137 (2009).
Bornholt, et al., "A DNA-based Archival Storage System", 21th ACM International Conference on Architectural Support for Programming Languages and Operating Systems, 1-13, (2016).
Braasch, et al., "Locked nucleic acis (LNA): fine-tuning the recognition of DNA and RNA", Chem. Biol., 8(1):1-7 (2001).
Brown, et al., "An easy-to-prepare mini-scaffold for DNA origami", Nanoscale, 7:16621-4 (2015).
Brudno, et al., "Recent progress toward the templated synthesis and directed evolution of sequence-defined synthetic polymers", Chem Biol., 16(3):265-276 (2009).

Castro, et al., "A primer to scaffolded DNA origami", Nat. Methods., 8(3):221-229 (2011).
Chandran, et al., "DNA origami: Folding DNA into Desired Shapes", Fourth Warft Workshop on Brain Modeling and Supercomputing, (2009).
Chasteen, et al., Eliminating helper phage from phage display Nucleic Acids Res., 34(21):e145 (2006).
Cho, "An unnatural biopolymer", Science, 261(5126):1303-1305 (1993).
Church, et al. "Next-generation digital information storage in DNA", Science, 337(6102):1628 (2012).
Clelland, et al., "Hiding messages in DNA microdots", Nature, 399(673):533-534 (1999).
Cong, "Multiplex genome engineering using CRISPR/Cas systems-",Science, 15:339(6121):819-823 (2013).
Cui, et al., "An encryption scheme using DNA technology", 2008 Third International Conference on Bio-Inspired Computing: Theories and Applications., 37-41(2008).
Dietz, et al., "Folding DNA into twisted and curved nanoscale shapes", Science, 325(5941):725-730 (2009).
Dotto, et al., "Initiation and termination of phage f1 plus-strand synthesis ", Proc. Natl. Acad. Sci. U.S.A., 79:7122-7126 (1982).
Douglas, et al., "Self-assembly of DNA into nanoscale three-dimensional shapes", Nature, 459(7425):414-418 (2009).
Douglas, et al., "A logic-gated nanorobot for targeted transport of molecular payloads", Science, 335(6070):831-834 (2012).
Douglas, et al., "Rapid prototyping of 3D DNA-origami shapes with caDNAno", Nucleic Acids Res., 37:5001-5006 (2009B).
Dunn, et al., "Guiding the folding pathway of DNA origami", Nature, 525(7567):82-86 (2015).
Dutta, et al., "DNA-directed artificial light-harvesting antenna", Journal of the American Chemical Society, 133(31):11985-11993 (2011).
Elbashir, et al., "Duplexes of 21-nucleotide RNAs mediate RNA interference in cultured mammalian cells", Nature, 411:494-498 (2001).
Elbaz, et al., "Genetic encoding of DNA nanostructures and their self-assembly in living bacteria", Nat Commun, 7:11179 (2016).
Ellis-Monaghan, et al., "DNA origami and the complexity of Eulerian circuits with turning costs", Nat. Comput., 14(3):491-503 (2015).
Ennifar, et al., "Targeting the dimerization initiation site of HIV-1 RNA with aminoglyocosides: from crystal to cell", Nucleic Acids Research. 34, 2328-2339 (2006).
Faber, et al., "Structural Rearrangements of HIV-1 Tat-responsive RNA upon Binding of Neomycin B*", The Journal of Biological Chemistry. 275:20660-20666 (2000).
Fan, et al., "Gating machinery of InsP3R channels revealed by electron cryomicroscopy", Nature, 527:336-341 (2015).
Fang, et al., "An unusual Topological Structure of the HIV-1 Rev Response Element" Cell, 155:594-605 (2013).
Fang, et al., "Small-angle X-ray scattering: a bridge between RNA secondary structures and three-dimensional topological structures" Current Opinion in Structural Biology. 30, 147-160 (2015).
Fire, et al. "Potent and specific genetic interference by double-stranded RNA in Caenorhabditis elegans", Nature, 391(6669):806-11 (1998).
Fu, et al., "Controlled drug release by a nanorobot", Nature Biotechnology, 30(5):407-408 (2012).
Fu, et al., "DNA double-crossover molecules", Biochemistry, 32(13):3211-3220 (1993).
Geary, et al., "RNA nanostructures. A single-stranded architecture for cotranscriptional folding of RNA nanostructures", Science, 345:799-804 (2014).
Gehani, et al., "DNA-based Cryptography", Lect Notes Comput Sc., 2950:167-188 (2004).
Gellman, "Foldamers: A Manifesto", Acc. Chem. Res., 31(4):173-180 (1998).
Goldman et al., "Towards practical, high-capacity, low-maintenance information storage in synthesized DNA", Nature, 494(7435):77-80 (2013).

(56) References Cited

OTHER PUBLICATIONS

Gradišar, et al., "Design of a single-chain polypeptide tetrahedron assembled from coiled-coil segments", Nat. Chem. Biol., 9(6):362-366 (2013).
Grass, et al., "Robust chemical preservation of digital information on DNA in silica with error-correcting codes", Angew. Chem. Int. Ed., 54(8):2552-2555 (2015).
Gruber, et al., "Efficient tumor cell lysis mediated by a bispecific single chain antibody expressed in *Escherichia coli*.", J. Immunol., 152(11):5368 (1994).
Gu, et al., "Dynamic patterning programmed by DNA tiles captured on a DNA origami substrate", Nature Nanotechnology, 4(4):245-248 (2009).
Han, et al., "DNA gridiron nanostructures based on four-arm junctions", Science. 339(6126):1412-1415 (2013).
Han, et al., "DNA origami with complex curvatures in three-dimensional space", Science, 332(6027):342-346 (2011).
Han, et al., "Single-stranded DNA and RNA origami", Science, 358(6369) (2017).
Hannon, "RNA interference", Nature, 418(6894):244-251 (2002).
He, et al., "Hierarchical self-assembly of DNA into symmetric supramolecular polyhedra", Nature, 452(7184):198-201 (2008).
He, et al., "On the Chirality of Self-Assembled DNA Octahedra", Angew. Chem., 122(4):760-763 (2010).
Henderson, et al., "Outcome of the first electron microscopy validation task force meeting", Structure, 20(2):205-214 (2012).
Hollinger, et al., "Diabodies: small bivalent and bispecific antibody fragments", Proc. Natl. Acad. Sci. U.S.A., 90(14):6444-6448 (1993).
Howe, et al., "Seletive small-molecule inhibition of an RNA structural element", Nature, 526:672-677 (2015).
Iinuma et al., "Supplementary Material for Polyhedra self-assembled from tripods and Chracterized with 3D DNA-PAINT", Science, 344(6179):65-69 (2014).
Iinuma, et al., "Polyhedra Self-Assembled from DNA-PAINT", Science, 344(6179): 65-69 (2014).
International Search Report for PCT/US2018/060727 dated Apr. 25, 2019.
Irobalieva, et al., "Structural diversity of supercoiled DNA", Nat. Commun., 6:8440 (2015).
Jiang, et al., "DNA origami as a carrier for circumvention of drug resistance", Journal of the American Chemical Society 134(32):13396-13403 (2012).
Jinek, et al., "A programmable dual-RNA-guided DNA endonuclease in adaptive bacterial immunity", Science, 337(6096):816-21 (2012).
Jones, et al., "Nanomaterials. Programmable materials and the nature of the DNA bond", Science, 347(6224):1260901 (2015).
Jones, et al., "Small-angle X-ray scattering-derived structure of the HIV-1 5' UTR reveals 3D tRNA mimicry", Proceedings of the National Academy of Sciences of the United States of America. 111:3395-3400 (2014).
Kallenbach, et al., "An immobile nucleic acid junction constructed from oligonucleotides", Nature, 305:829-831 (1983).
Kazantsev, et al., Proceedings of the National Academy of Sciences of the United States of America. 100: 7497-7502 (2003).
Ke, et al. "Multilayer DNA Origami Packed on a Square Lattice", J. A. Chem. Soc., 131:15903-15908 (2009).
Ke, et al., "DNA brick crystals with prescribed depths", Nat. Chem., 6:994-1002 (2014).
Ke, et al., "Self-Asssembled Water-Soluble Nucleic Acid Probe Tiles for Label-Free RNA Hyrbidization Assays", Science, 319:180-183 (2008).
Ke, et al., "Three-dimensional structures self-assembled from DNA bricks", Science, 338(611): 1177-1183 (2012).
Ke, et al., "Two design strategies for enhancement of multilayer-DNA-origami folding: underwinding for specific intercalator rescue and staple-break positioning",Chem. Sci., 3(8):2587-2957 (2012B).
Keane, et al., "Structure of the HIV-1 RNA packaging signal", Science, 348(6237):917-921 (2015).
Kertesz, et al., "Genome-wide measurement of RNA secondary structure in yeast", Nature, 467:103-107 (2010).
Kick, et al., "Efficient Production of Single-Stranded Phage DNA as Scaffolds for DNA Origami", Nano Lett, 15:4672-6 (2015).
Kim et al., "Extending Lifetime of Flash Memory Using Strong Error Correction Coding", IEEE Trans. Consum. Electron., 61:206-214 (2015).
Kim, et al. "Insertion and deletion mutants of FokI restriction endonuclease", J. Biol. Chem., 269:31978-31982 (1994B).
Kim, et al., "Chimeric restriction endonuclease", Proc. Natl. Acad. Sci. USA., 91:883-887 (1994A).
Ko, et al., "Synergistic self-assembly of RNA and DNA molecules", Nature Chemistry, 2(12):1050-1055 (2010).
Kostelny, et al., "Formation of a bispecific antibody by the use of leucine zippers", J. Immunol., 14 8(5):1547-1553 (1992).
Krishnan, et al., "Designer nucleic acids to probe and program the cell", Trends in Cell Biology, 22(12):624-633 (2012).
Kurreck, et al., "Design of antisense oligonucleotides stabilized by locked nucleic acids", Nucleic Acids Res., 30(9):1911-1918 (2002).
Kuzyk, et al., "DNA-Based Self-Assembly of Chiral Plasmonic Nanostructures With Tailored Optical Response", Nature, 483(7389):311-314 (2012).
Leier, et al., "Cryptography with DNA binary strands", Biosystems, 57(1):13-22 (2000).
Li, et al., "Alteration of the cleavage distance of Fok I restriction endonuclease by insertion mutagenesis", Proc. Natl. Acad. Sci. USA, 90(7):2764-2768 (1993).
Li, et al., "Functional domains in Fok I restriction endonuclease", Proc., Natl. Acad. Sci. USA, 89(10):4275-4279 (1992).
Li, et al., "Nucleic-based nanoengineering: novel structures for biomedical applications", Interface Focus, 1(5): 702-724 (2011).
Li, et al., "Quantifying Absolute Protein Synthesis Rates Reveals Principles Underlying Allocation of Cellular Resources", Cell, 157(3):624-635 (2014).
Liedl, et al., "Self-assembly of 3D prestressed tensegrity structures from DNA", Nature Nanotechnology, 5:520-524 (2010).
Linko, et al., "Automated design of DNA origami", Nature Biotechnology, 34(8):826-827 (2016).
Liu et al., "Crystalline two-dimensional DNA-origami arrays", Angew. Chem. Int. Ed. Engl., 50(1):264-267 (2011).
Liu, et al., "Diamond family of nanoparticle superlattices", Science, 351(6273):582-586 (2016).
Liu, et al., "Quantifying Absolute Protein Synthesis Rates Reveals Principles Underlying Allocation of Cellular Responses", Nano Letters, 12:4254-4259 (2012).
Lutz, et al., "Sequence-controlled Polymers", Science, 341:1238149 (2013).
Marchi, et al., "Toward larger DNA origami", Nano Lett, 14:5740-7 (2014).
Martin, et al., "Magnesium-free self-assembly of multi-layer DNA objects", Nat. Commun., 3:1103 (2012).
Masanori, et al., "Chapter 368: DNA Memory", Handbook of Natural Compu, 1281-1318 (2012).
Maxam et al., "A new method for sequencing DNA", Proc. Nat. Acad. Sci. USA, 74(2):560-564 (1977).
Mercer, et al., "Structure and function of long noncoding RNAs in epigenetic regulation", Nature Structural & Molecular Biology. 20, 300-307 (2013).
Michelotti, et al., "Beyond DNA origami: a look on the bright future of nucleic acid nanotechnology", Wiley Interdiscip Rev Nanomed Nanobiotechnol., 4(2):139-152 (2012).
Morrison, et al., "Chimeric human antibody molecules: mouse antigen-binding domains with human constant region domains", Proc. Natl. Acad. Sci. USA, 81:6851-6855 (1984).
Nafisi, et al., "Construction of a novel phagemid to produce custom DNA origami scaffolds", Synthetic Biology, 3(1), ysy015 (8 pages) (2018).
Napoli, et al., Introduction of a Chimeric Chalcone Synthase Gene into Petunia Results in Reversible Co-Suppression of Homologous Genes in trans., Plant Cell, 2(4):279-289 (1990).
Nelson, "Droplet Actuation by Electrowetting-on-Dielectric (EWOD): A Review", Journal of Adhesion Science and Technology, 26:747-1771 (2012).
Nickels, et al., "DNA origami structures directly assembled from intact bacteriophages", Small, 10:1765-9 (2014).

(56) References Cited

OTHER PUBLICATIONS

Nielsen, et al., "Sequence-selective recognition of DNA by strand displacement with a thymine-substituted polyamide", Science, 254(5037): 1497-1500 (1991).
Nogales, et al., "Cryo-EM: A Uniquw Tool for the vizualization of Macromolecular Complexity", Molecular Cell, 58:677-689 (2015).
Olson, et al., "New Structue Sheds Light on Selective HIV-1 Genomic RNA Packaging", Viruses, 7:4826-4835 (2015).
Pan, et al., "Lattice-free prediction of three-dimensional structure of programmed DNA assemblies", Nature Communications., 5:5578 (2014A).
Pan, et al., "Structure-based model for light-harvesting properties of nucleic acid nanostructures", Nucleic Acids Research, 42(4):2159-2170 (2014B).
Pandey, et al., "Algorithmic design of self-folding polyhedral", Proc. Natl. Acad. Sci. 108(50):19885-19890 (2011).
Pardee, et al., "Paper-based synthetic gene networks", Cell, 159(4):940-954 (2015).
Pasqualini, et al., "Organ targeting in vivo using phage dislay peptide libraries", Nature, 380:364-366 (1996).
Peng, et al., "Bottom-up nanofabrication using DNA nanostructures", Chem Matter, 28(4):1012-1021 (2016).
Praetorius, et al., "Biotechnological mass production of DNA origami", Nature, 552(7683):84-7 (2017).
Prim, "Shortest connection networls and some generalizations", Bell Syst. Tech. J., 36(6):1389-1401 (1957).
Rich, "The rise of single-molecule DNA biochemistry", Proc. Natl. Acad. Sci. U. S. A., 95(24):13999-14000 (1998).
Rothemund, "Scaffolded DNA Origami: from Generalized Multicrossovers to Polygonal Networks", Nanotechnology: Science and Computation, 3-21 (2006b).
Rothemund, et al., "Algorithmic self-assembly of DNA Sierpinski Triangles", PLoS Biol., 2:2041-2053 (2004).
Rothemund, et al., "Folding DNA to create nanoscale shapes and patterns", Nature, 440(7082):297-302 (2006).
Rouskin, et al., "Genome-wide probing of RNA structure reveals active unfoldinng of mRNA strucutres in vivo", Nature. 505:701-705 (2014).
Said, et al., "M1.3—a small scaffold for DNA origami", Nanoscale, 5(1):284-290 (2013).
Sanger, et al., "DNA sequencing with chain-terminating inhibitors", Proc. Natl. Acad. Sci. U.S.A., 74(12):5463-5467(1977).
Santangelo, et al., "Nanostructred Probes for RNA Detection in Living Cells", Annals of Biomedical Engineering, 34:39-50 (2006).
Seeman, et al., "Design of immobile nucleic acid junctions", Biophys. J., 44(2):201-209 (1983).
Seeman, et al., "DNA nicks and nodes and nanotechnology", Nano Lett., 1:22-26 (2001).
Sharma, et al., "Control of self-assembly of DNA tubules through integration of gold nanoparticles", Science, 323:112-6 (2009).
Shaw, et al., "Purification of functionalized DNA origami nanostructures", ACS Nano, 9(5): 4968-4975 (2015).
Shih, et al., "A 1.7-kilobase single-stranded DNA that folds into a nanoscale octahedron", Nature, 427(6975):618-621 (2004).
Siegfried, et al.," RNA motif discovery by SHAPE and mutational profiling (SHAPE-MaP)", Nature Methods, 11(9):959-965 (2014).
Sinclair, et al., "Generation of protein lattices by fusing proteins with matching rotational symmetry", Nat. Nanotechnol. 6(9):558-562 (2011).
Smola, et al., "Selective 2'-hydroxyl acylation analyzed by primer extension and mutational profiling (SHAPE-MaP) for direct, versatile and accurate RNA structure analysis", Nat Protoc.10(11):1643-1669 (2015).
Sobczak, et al., "Rapid folding of DNA into nanoscale shapes at constant temperature", Science, 338(6113):1458-1461 (2012).
Songsivilai, et al., "Bispecific antibody: a tool for diagnosis and treatment of disease", Clin. Exp. Immunol., 79(3):15-321 (1990).
Specthrie, et al., "Construction of a microphage variant of filamentous bacteriophage", Mol. Biol., 228:720-724 (1992).
Spink, et al., "Thermodynamics of forming a parallel DNA crossover", Biophysical Journal, 97(2):528-538 (2009).
Staple, et al., "Solution structure and thermodynamic investigation of the HIV-1 frameshift inducing element", Journal of Molecular Biology, 349:1011-1023 (2005).
Stephenson, et al., "Three-Dimensional RNA Structure of the major HIV-1 Packaging Signal Region", Structure, 21:951-962 (2013).
Sun, et al., "Casting inorganic structures with DNA molds", Science, 346(6210):1258361 (2014).
Tintore, et al., "DNA origami as a DNA repair nanosensor at the single-molecule level", Angew Chem Int Ed Engl.,52(30):7747-7750 (2013).
Tomley, et al., "M13 Phage Growth and Single-Stranded DNA Preparation", Methods Mol. Biol., 58:359-362 (1996).
Torring, et al., "DNA origami: a quantum leap for self-assembly of complex structures", Chem. Soc. Rev., 40:5636-5646 (2011).
Tumpane, et al., "Triplex addressability as a Basis for Functional DNA Nanostructures", 7(12):3832-3839 (2007).
Ubaidurrahman, et al., "A Novel DNA Computing Based Encryption and Decryption Algorithm", Procedia Comput Sci., 46:463-475 (2015).
Ui-Tei, et al., "Sensitive assay of RNA interference in *Drosophila* and Chinese hamster cultured cells using firefly luciferase gene as target", FEBS Lett, 479(3):79-82 (2000).
Untergasser, et al., "Primer3—new capabilities and interfaces", Nucleic Acids Res. 40(15): e115-e115 (2012).
Veneziano, et al, "Designer nanoscale DNA assemblies programmed from the top down.", Science, 352(6293):1534 (2016).
Veneziano, et al., "Designer nanoscale DNA assemblies programmed from the top down", Science, Supplementary Materials (2016).
Veneziano, et al., "Enzymatic Synthesis of gene-length single-stranded DNA", bioRxiv (2017).
Vogel, et al., Hfq and its constellation of RNA, Nature Reviews Microbiology. 9:578-589 (2011).
Wahlestedt, et al., "Potent and nontoxic antisense oligonucleotides containing locked nucleic acids", Proc. Natl Acad. Sci. USA, 97(10):5633-5638 (2000).
Wang, "Double-stranded DNA homology produces a physical signature", PNAS, 107(28):12547-12552 (2010).
Wang, et al., "An atomic model of brome mosaic virus using direct electron detection and reasl-space optimization", Nature Communications, 5(4808) (2014).
Watts, et al., "Architecture and secondary structure of an entire HIV-1 RNA genome", Nature, 460:711-716 (2009).
Wei, et al., "Complex shapes self-assembled from single-stranded DNA tiles", Nature, 485(7400): 623-626 (2012).
Wilkinson, et al., "Selective 2'-hydroxyl acylation analyzed by primer extension (SHAPE): quantitative RNA structure analysis at single nucleotide resolution", Nature Protocols, 1(3)1610-1616 (2006).
Winfree, et al., "Design and self-assembly of two-dimensional DNA crystals", Nature, 394(6693):539-544 (1998).
Winter, et al., "Making antibodies by Phage Display Technology", Annu Rev Immunol., 12:433-455 (1994).
Wong, et al., "Organic Data Memory Using the DNA Approach", Communications of the ACM., 46:95-98 (2003).
Woo, et al., "Programmable molecular recognition based on the geometry of DNA nanostructures", Nat. Chem., 3(8):620-627 (2011).
Wooddell, et al., "Use of asymmetric PCR to generate long primers and single-stranded DNA for incorporating cross-linking analogs into specific sites in a DNA probe", Genome Res. 6(9):886-892 (1996).
Wynn, et al., "HIV-1 drug discovery: targeting folded RNA structures with branched peptides", Organic & Biomolecular Chemistry, 13, 5848-5858 (2015).
Xu, et al., "Design of 240,000 orthogonal 25mer DNA barcode probes", PNAS., 106(7):2289-2294 (2009).
Xuan, "Ultrasound-responsive block copolymer micelles based on a new amplification mechanism", Langmuir, 28(47):16463-16468 (2012).
Yan, et al., "DNA-templated self-assembly of protein arrays and highly conductive nanowires", Science, 301:1882-1884 (2003).

(56) References Cited

OTHER PUBLICATIONS

Yang, et al, "Self-assembly of DNA rings from scaffold-free DNA tiles," Nano Letters, 13(4):1862-1866 (2013).
Yazdi, et al., "A Rewritable, Random-Access DNA-Based Storage System", Scientific reports, 5:14138 (2015).
Yim, et al., "The Essential Component in DNA-Based Information Storage System: Robust Error-Tolerating Module", Frontiers in bioengineering and biotechnology, 2:49 (2014).
Zhang, et al., "Complex wireframe DNA origami nanostructures with multi-arm junction vertices", Nat. Nanotechnol, 10(9):779-784 (2015).
Zhao, et al., "Organizing DNA origami tiles into larger structures using preformed scaffold frames", Nano Lett., 11(7):2997-3002 (2011).
Zhirnov, et al., " Nucleic acid memory", Nat Mater., 15(4):366-70 (2016).
Zuckermann, et al., "Efficient method for the preparation of peptoids [oligo(N-substituted glycines)] by submonomer solid-phase synthesis", J. Am. Chem. Soc., 114(26):10646-10647(1992).

\* cited by examiner

MICROBIAL PRODUCTION OF PURE SINGLE STRANDED NUCLEIC ACIDS

CROSS-REFERENCE TO RELATED APPLICATIONS

This application claims the benefit of and priority to U.S. Application No. 62/584,664 filed Nov. 10, 2017, and which is incorporated by reference in its entirety.

STATEMENT REGARDING FEDERALLY SPONSORED RESEARCH

This invention was made with government support under Grant Nos. N00014-16-1-2953; and N00014-17-1-2609 awarded by the Office of Naval Research. The government has certain rights in the invention.

REFERENCE TO SEQUENCE LISTING

The Sequence Listing submitted as a text file named "MIT_19562_ST25.txt," created on Nov. 9, 2018, and having a size of 73,832 bytes is hereby incorporated by reference pursuant to 37 C.F.R. § 1.52(e)(5).

FIELD OF INVENTION

The present invention relates generally to compositions and methods of bacterial production of pure, homogeneous single-stranded nucleic acid products composed nearly completely of non-natural nucleotide sequences for application to scaffolded nucleic acid origami synthesis, in addition to other molecular and biochemical techniques based on kilobase single-stranded DNA.

BACKGROUND OF THE INVENTION

Scaffolded deoxyribonucleic acid (DNA) origami folds a long single-stranded DNA (ssDNA; "scaffold") into a user-defined shape by slowly annealing the scaffold in the presence of shorter oligonucleotides ("staples") containing segments or regions of complementary sequences to the scaffold that bring sequences that are far apart in sequence space to nearby locations in Euclidian space. These interactions and geometries are stabilized by specific Watson-Crick base pairing in the presence of salt that uses immobile Holliday junctions ("crossovers") to constrain neighboring duplexes physically in space. Crossovers are generally engineered to occur between two parallel DNA duplexes at positions closest or nearest between the two or more helices of the DNA within a 1D, 2D, or 3D structure. Scaffolded DNA origami was initiated by William Shih using a combination of parallel and anti-parallel crossovers (Shih, et al., Nature, 427(6975):618-21 (2004)) and subsequently Paul Rothemund using solely anti-parallel crossovers that has become the most ubiquitous form of scaffolded DNA origami (Rothemund, P W, Nature, 440, 297-302 (2006)), where Rothemund used M13 genomic ssDNA as the scaffold, and the technique has been further modified and generalized by numerous laboratories (Sharma, J et al., Science, 323, 112-116 (2009); Dietz, H. et al., Science, 325, 725-730 (2009); Douglas, S. M. et al., Nature, 459, 414-418. (2009); Brown, S et al., Nanoscale, 7, 16621-16624 (2015); Marchi, A. N. et al., Nano Lett, 14, 5740-5747 (2014)) using M13 or Phage lambda DNA. Additional, top-down design of scaffolded DNA origami nanostructures has been enabled to automatically generate the scaffold routing and complementary ssDNA staple strands to self-assemble under appropriate folding conditions into user-defined geometries of 1D, 2D, or 3D shapes (Veneziano, R et al., Science, 352, 1534 (2016); Benson, E et al., Nature, 523, 441-444 (2015); Douglas, S. M. et al., Nucleic Acids Res, 37, 5001-5006 (2009)), and was the subject of prior work, demonstrating generality of sequence design for scaffold DNA (see, for example, US20030215914A1, US20050147962A1, WO2017089567A1, WO2017089570A1, and CN106119269A).

One tile-based method allowed for generation of 2D wireframe objects (Yan, H et al., Science, 301, 1882-1884 (2003)) that was subsequently implemented experimentally using M13-based scaffolded DNA origami to a include diversity of 2D and closed 3D shapes (Zhang, et al., Nat Nanotechnol., 10(9):779-84 (2015)). This latter scaffolded DNA origami approach was subsequently generalized and fully automated for 3D shapes by Veneziano et al., (Veneziano, et al., Science, 352(6293):1534 (2016)).

Non-scaffolded DNA origami is an alternative approach that uses purely short strands of synthetic single-stranded DNA to self-assemble via thermally annealed folding large-scale arrays of structured DNA via a process known as 'tile-based' assembly (Yan, H et al., Science, 301, 1882-1884 (2003); Winfree, E et al., Nature, 394, 539-544 (1998); Ke, Y et al., Science, 338, 1177-1183 (2012); Ke, Y et al., Nat Chem, 6, 994-1002 (2014)). In vivo production of top-down designed nanoparticles has long been one goal of the field, with recent promising successes in RNA and DNA (Elbaz, J et al., Nat Commun, 7, 11179 (2016); Geary, C et al., Science, 345, 799-804 (2014); Nickels, P. C. et al., Small, 10, 1765-1769 (2014); Han, et al., Science, 358 (6369) (2017)).

Historically, scaffolded DNA origami has largely relied on the natural M13 phage genomic single-stranded DNA as the scaffold (Rothemund, P W, Nature, 440, 297-302 (2006)). This is because it is natively single stranded and easy to produce in the bacteria *E. coli*, and therefore is available at low cost in large quantities. Efforts to increase production of M13 phage DNA have shown success, obtaining up to 410 mg of ssDNA from 1 liter of *E. coli* growth (Kick, B et al., Nano Lett, 15, 4672-4676 (2015)). A drawback of this approach is that the native M13 genome is minimally approximately 7,000 nucleotides with wild-type variation in sequence. While this genomic DNA sequence can be increased or decreased in length, historically, demonstration that the DNA sequence itself can be varied from wildtype variations has been limited (Praetorius, et al., Nature, 552 (7683):84-87 (2017), Nafisi, et al., Synthetic Biology, 3(1), ysy015 (8 pages) (2018), Chasteen, et al., Nucleic Acids Res. 34(21):e145 (2006)). This limits use of the M13-based scaffold to applications that do not rely on synthetic, non-wildtype sequences for folding, conjugation, interaction with secondary RNAs and proteins, or other important variations for function. For lower molecular weight scaffolded DNA origami nanoparticles, length control in addition to sequence control over M13 phage produced scaffold can be limiting.

The wildtype M13 genome encodes 10 proteins (gene 1 protein-gene 10 protein; G1P-G10P) that are produced within the *E. coli* as part of its life cycle. Functional viral production is achieved by self-assembly of 2,700 copies of the major coat protein, G8P, together with 5 copies of each of the four minor coat proteins: G7 and G9 proteins at the tail of the virion and G3 and G6 proteins at the head. In addition, G2P is responsible for cleavage of the double-stranded genomic intermediate at the origin of replication, and ligation of the newly synthesized, replicated single-stranded genome. G10P binds the double-stranded intermediate and acts as a control to prevent hydrolysis and over-generation of ssDNA, while G5P binds to the ssDNA and prevents formation of dsDNA. G1P and G4P are subsequently involved in packaging the genomic ssDNA into the viral particle and exporting fully-formed viral particles from the cell. The packaging signal is additionally part of the origin of replication (f1) that encodes the initiation point for replication, which partially relies on E. coli replication enzymes.

M13 phage has found major application in phage display of proteins. In phage display, a protein-protein or protein-DNA interaction is interrogated by expressing and displaying proteins of interest on the surface of the phage particle by encoding it as part of the gene 3 protein (Pasqualini, R et al., Nature, 380, 364-366 (1996); Winter, G et al., Annu Rev Immunol, 12, 433-455 (1994)). This generates the particle with the protein exposed to the outside, and thus allows for external, solvent-exposed access to interrogate its biomolecular and other surface-based interactions while simultaneously containing the gene encoding the protein of interest inside the particle, linking phenotype with genotype. This phage display system has been greatly aided by the development of the helper plasmid with associated phage-encoding plasmids ("phagemids;" e.g. M13KO7, New England Biolabs, Ipswitch, Mass., product N0315S). In this system, the 10 genes encoding the phage proteins are placed onto a plasmid ("helper plasmid") that persists in E. coli, typically, for example, replicating under the p15A origin of replication. Phagemids also contain an f1-origin to package the phagemid into the phage particle, allowing for viral spread of the phagemid within an E. coli culture containing the fertility epitope. The utility of this phagemid approach is that a separate plasmid containing an f1-origin and typically encoding the phage gene 3 modified by the gene sequence of the protein of interest to be displayed on the phage particle is introduced to the infected E. coli culture through routine transformation and then packaged and displayed. For ease of cloning, phagemid DNA generally also contains a high-copy origin of replication such as the pUC origin, thus producing dsDNA in the cell with moderate leakage of dsDNA into the phage particle.

The phagemid system has been shown to be useful for scaffolded DNA origami by production of a phagemid that encodes the f1-origin, a pUC origin, and an ampicillin selection marker. This was combined with a normal helper plasmid to produce ssDNA that could be used to fold DNA nanoparticles, but was significantly contaminated both by dsDNA phagemid and helper phage. These dsDNA impurities require subsequent purification steps to isolate the target ssDNA for any further scale-up. The authors pointed out that the ssDNA is contaminated by the dsDNA. The dsDNA contamination can be purified away using size exclusion chromatography, agarose gel purification, charge-based purification, or sequence-based purification, but efforts to scale these to the 100-mg and higher scales have not been reported.

Thus, there is a need in the art for a cost-effective and time-effective strategy allowing the large-scale production of homogeneous single-stranded DNA without the need for in vitro production or purification techniques.

Therefore, it is an object of the invention to provide compositions and methods for the in vivo production of isolated single-stranded DNAs of user-defined size and sequence, using only one line of genetically-engineered microorganisms.

It is also an object of the invention to provide microorganisms producing bacteriophage encapsulating a highly-pure single-stranded DNA, without contamination of double-stranded DNA.

It is also an object of the invention to generate compositions and methods for bacteriophage libraries of homogeneous and highly-pure single-stranded DNAs, amenable to folding into nanoscale DNA origami objects without further purification.

It is a further object of the invention to generate compositions and methods for folding of single-stranded DNAs into nanoscale DNA origami objects in vivo.

It is another object of the invention to provide a system that encodes both the ssDNA (e.g., for scaffolded DNA origami) as well as therapeutic/CRISPR RNAs/proteins for full production and packaging.

SUMMARY OF THE INVENTION

Compositions and methods for in vivo production of highly-pure single-stranded DNAs isolated within bacteriophage have been established. The bacteriophage particles are produced by engineered bacteria containing both a phagemid and a helper plasmid. In some embodiments, the helper plasmid does not include the f1-origin of replication, and is under the control of a selection factor. An exemplary selection factor is exposure to chloramphenicol. This plasmid is still under the control of the p15A origin of replication for medium copy number (~10 copies per cell) and produces all 10 M13 phage proteins, but does not get packaged into the phage particle because the packaging signal does not reside within the helper plasmid sequence and the helper plasmid sequence is not single-stranded. Thus, the particles that are produced contain genetically pure ssDNA. To achieve gram-scale quantity of ssDNA composed of an arbitrary sequence that is also genetically pure and produced by bacteria, the helper system M13cp can be used to clone and produce phage particles that meet these specifications.

Synthesis of single-stranded DNA (ssDNA) can be scaled up by using a helper-strain Escherichia coli (E. coli) system to produce highly pure ssDNA exported from the E. coli without the need for additional biochemical purifications away from the contaminating dsDNA and other non-target ssDNA. The target ssDNA can be composed of custom sequence and size ranging from 427 nt to 10,000 nt or longer than 10,000 nt, and any number of nucleotides between these sizes (e.g. 428, 429, 9,998, 9,999, etc.). The phasmid carrying the target ssDNA sequence need only contain the target DNA sequence, a bacteriophage origin of replication, for example, the f1-origin of replication, and a packaging sequence. Thus, the target ssDNA may can contain the sequence of a bacteriophage origin of replication, for example, the f1-origin of replication, and a packaging sequence.

In an exemplary proof-of-principle embodiment, a variation of the M13cp helper strain E. coli transformed with phagemids containing only the 427 nt f1-origin of replication and either biological or purely synthetic (i.e., naturally occurring or non-naturally occurring, respectively) sequences were used. Because these phagemids do not contain any origins besides the f1-origin, they are only capable of being replicated within the helper plasmid-transformed E. coli, and are packaged within the produced phage particles. By combining centrifugation or filtration with DNA extraction techniques, this strategy enables complete purification of ssDNA without the requirement of additional purification steps to remove contaminating DNA.

Applications of this approach are also illustrated and described below, including using the purified ssDNA for folding scaffolded DNA origami nanoparticles, user-defined DNA encoding paranemic crossover origami, and binding sites for CRISPR proteins, single guide or CRISPR RNAs, or siRNAs for packaging of pure biomolecules. Typically the ssDNA produced by the methods is isolated from dsDNA and/or other sources of ssDNA. For example, the isolated ssDNA can be present in a bacteriophage that includes no dsDNA, or includes only a small amount of dsDNA. For example, the amount of dsDNA present in the bacteriophage can be less than 10% by weight of the total, less ten a 5% by weight, less than 4%, 3%, 2%, 1%, or less than 0.1% by weight of the total DNA within the bacteriophage. Typically, the ssDNA of user-defined size and sequence is of sufficient purity to facilitate folding into a DNA origami nanostructure without the need for further purification. Generally, any dsDNA or other contaminants are not present in sufficient quantity to prevent or disrupt the hybridization or folding of the ssDNA into a DNA origami nanostructure.

Methods for assembling two or more nucleic acid sequences to form a long single-stranded nucleic acid scaffold sequence for a nucleic acid nanostructure are also disclosed. Typically, the methods include mixing two or more nucleic acids to create a reaction mix, and producing a long single-stranded nucleic acid scaffold sequence including the one or more naturally or non-naturally occurring nucleic acid sequences within the reaction mix using asymmetric Polymerase Chain Reaction (aPCR). Typically, the long single-stranded nucleic acid scaffold sequence includes the origin of replication from a class 1 filamentous bacteriophage and one or more naturally or non-naturally occurring nucleic acid sequences of between 1 and 1,000,000 nucleotides in length. An exemplary origin of replication is the 427 nucleotide f1-origin of replication form a class 1 filamentous bacteriophage. In some embodiments, the long single-stranded nucleic acid scaffold sequence includes a selection marker. An exemplary is the 1,249-nt ampicillin resistance cistron.

In some embodiments, methods include mutagenizing the long single-stranded nucleic acid. Exemplary mutagenic agents include $MnSO_4$, caffeine, or Ultra Violet (UV) light. In certain embodiments, the single-stranded nucleic acid is complementary by 1, 2, 3, 4, 5, or 6 nucleotides, or greater than 6 nucleotides, to a second single-stranded nucleic acid generated by asymmetric PCR. In certain embodiments, the long single-stranded nucleic acid scaffold sequence is a phagemid of between 400 and 1,000,000 nucleotides in length. The methods can include the step of producing a double-stranded nucleic acid corresponding to the long single stranded nucleic acid sequence using a polymerase enzyme.

The methods can include the step of encapsulating the long single-stranded nucleic acid scaffold sequence within a bacteriophage particle. Preferably, the nucleic acid within the bacteriophage particle comprises less than 10%, less than 5%, preferably less than 1% weight:weight of double-stranded DNA.

Single-stranded nucleic acid scaffold sequence produced according to the methods are also disclosed. In some embodiments, the nucleic acid sequence encodes digital bitstream data, or a bait or capture sequence that can anneal or bind biological materials including DNA, RNA, or nucleic-acid-binding proteins. An exemplary nucleic-acid-binding protein is specific for a gene editing ribonucleoprotein complex. In some embodiments, the nucleic acid scaffold sequence folds into a nucleic acid nanoparticle without staples. In other embodiments, the nucleic acid scaffold sequence folds into a nucleic acid nanoparticle with 1, 2, 3, or more than 3 staples.

Methods for the in vivo production of a long single-stranded nucleic acid scaffold sequence of between 1 and 1,000,000 nucleotides in length, are also provided. The methods include one or more of the steps of producing a long single-stranded nucleic acid sequence that is a scaffold for a nucleic acid nanoparticle formation within a microorganism; packaging the long single-stranded nucleic acid scaffold sequence within a bacteriophage particle within the microorganism; and isolating the long single-stranded nucleic acid scaffold sequence from the bacteriophage particle. The methods can optionally include the step of folding the long single-stranded nucleic acid scaffold sequence into a nucleic acid nanoparticle. Isolating the long single-stranded nucleic acid scaffold sequence from the bacteriophage particle can include harvesting phage particles directly from clarified growth media. Harvesting phage from the media typically includes buffer-exchanging the clarified growth media; and concentrating the phage particles. Typically, the methods do not require removal of double-stranded DNA from the bacterially-produced single-stranded nucleic acid scaffold prior to folding into a nucleic acid nanoparticle Phage particles, microorganisms, phagemids and nucleic acid nanoparticles folded from the single single-stranded nucleic acid sequence produced by the described methods are also described.

For example, isolated nucleic acids including, encoding, or a combination thereof a bacteriophage origin of replication, a sequence encoding a bacteriophage packaging signal, and a heterologous sequence encoding a target single-strand DNA (ssDNA) sequence of interest are provided. Preferably, the isolated nucleic acid does not include or encode a plasmid origin of replication. The isolated nucleic acid optionally include or encode a selectable marker. The isolated nucleic acid can be single stranded or double stranded. The isolated nucleic acid can be linear or circular. Preferably, the isolated nucleic acid is circular. The target ssDNA sequence of interest can be a scaffold sequence. The scaffold sequence can form a 2D or 3D DNA origami structure. The target ssDNA sequence of interest can encode bitstream data.

In some embodiments, the isolated nucleic acid is a phagemid including the nucleic acid sequence of any one of SEQ ID NO:1, or 4-7, or a variant thereof with at least 75%, 80%, 85%, 90%, or 95% sequence identity to any one of SEQ ID NO:1, or 4-7. The phagemid can include, for example, the backbone of SEQ ID NO:1 or 4-7, wherein a target single-strand DNA (ssDNA) sequence of interest is inserted into the backbone or substituted for an existing sequence without disrupting the bacteriophage origin of replication or sequence encoding the bacteriophage packaging signal.

In some embodiments, the phagemid is a variant of the phagemid of any one of SEQ ID NO:1 or 4-7 comprising a nucleic acid sequence encoding a bacteriophage origin of replication, absence of a plasmid origin of replication, and optionally nucleic acid sequences encoding a selectable marker and/or a target single-strand DNA (ssDNA) sequence of interest, wherein the bacteriophage origin of replication is substituted with an alternative origin of replication, any selectable marker is substituted with an alternative selectable marker or deleted, any target single-strand DNA (ssDNA) sequence of interest is substituted with an alternative target single-strand DNA (ssDNA) sequence of interest or deleted, or a combination thereof relative to SEQ ID NO:1 or 4-7.

Host cells including the disclosed isolated nucleic acids, phagemids, and plasmids are also provided. For example, in some embodiments, the host cell includes one or more of the isolated nucleic acids or phagemids alone or in combination with a double stranded nucleic acid helper plasmid, wherein the helper plasmid includes one or more proteins capable of packaging single stranded nucleic acids including the bacteriophage packaging signal into a bacteriophage particle, wherein the helper plasmid itself lacks a packaging signal.

In some embodiments, the helper plasmid, or a second plasmid, encodes one or more additional functional elements that can be incorporated into or onto the target ssDNA of interest. The one or more functional elements can be, for example, single-guide- or crispr-RNAs (crRNA), anti-sense DNA, anti-sense RNA, one or more proteins, or a combination thereof. The anti-sense RNA can be, for example, RNAi, miRNA, piRNA and siRNA. The one or more proteins can be therapeutic, non-therapeutic, or a combination thereof. In particular embodiments, the one or more proteins includes a Cas protein, TAL effector protein, or zinc-finger protein. In some embodiments, the host cells also express single-guide- or crispr-RNAs (crRNA) alone or in combination with a Cas protein. Thus, the disclosed compositions and methods can be used to package a gene editing composition including a CRISPR/Cas system into a ssDNA scaffold carrier.

In particular embodiments, a plasmid encoding one or more functional elements includes the nucleic acid sequence of SEQ ID NO:8, or a variant thereof with at least 75%, 80%, 85%, 90%, or 95% sequence identity to SEQ ID NO:8. Exemplary cloning cassettes and staple sequences are provided as SEQ ID NOS:2, 3, and 62-64.

BRIEF DESCRIPTION OF THE DRAWINGS

FIG. 8A shows the chromatogram corresponding to gel densitometry from an agarose gel run with a miniprep of the bacterial pellet containing the F1-Amp phagemid. FIG. 8B shows the chromatogram corresponding to gel densitometry from an agarose gel run with purified ssDNA from the supernatant media. Vertical line indicates the placement of the ssDNA band.

FIG. 9A shows the chromatogram corresponding to gel densitometry from a 12 mM MgCl2-containing agarose gel run with purified F1-Amp phagemid. FIG. 9B shows the chromatogram corresponding to gel densitometry from the same gel run with DNA combined with staples and annealed after 13 hours from 95 C to 25 C. Vertical line indicates the placement of the ssDNA band. Peak shift indicates folding of nanoparticles.

DETAILED DESCRIPTION OF THE INVENTION

Figure 1:
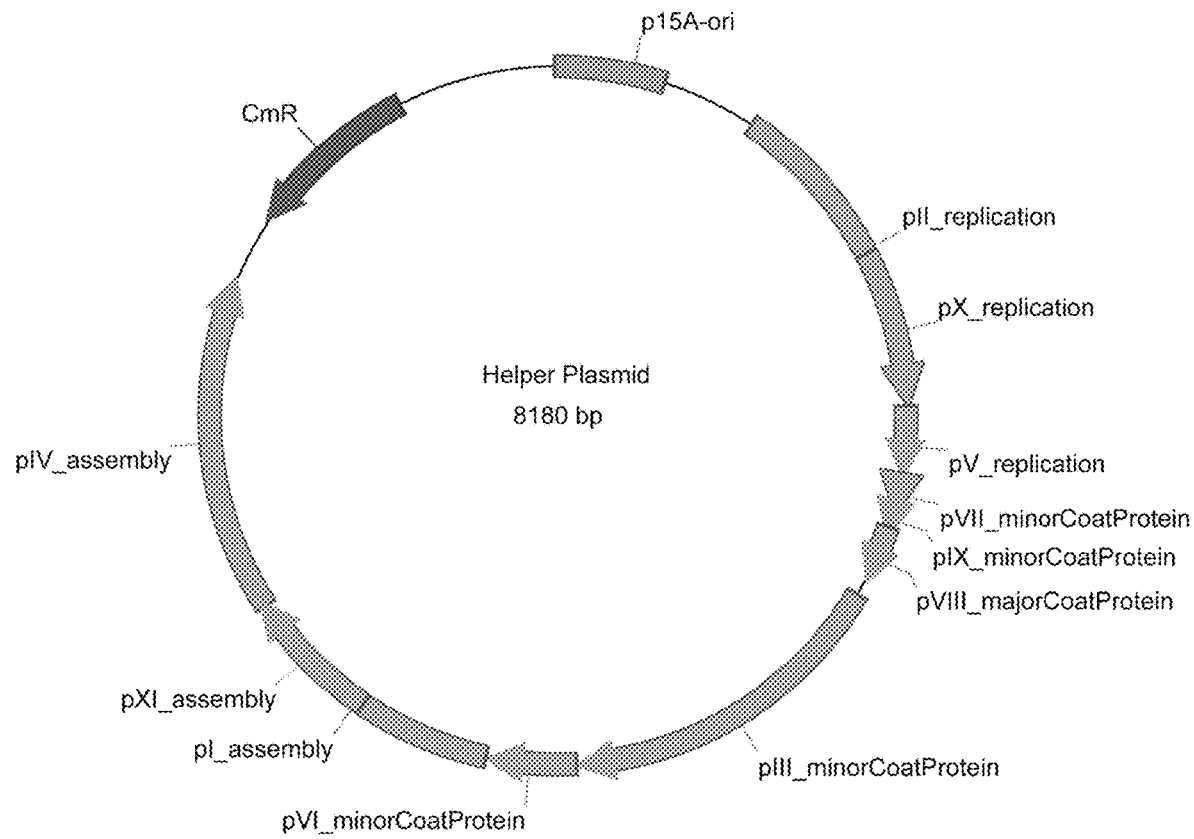
FIG. 1 is a schematic representation of the plasmid map of a helper plasmid, generated by cloning the M13 gene-encoding section of DNA containing 10 Open Reading Frames (ORFs) to the chloramphenicol acetyl transferase and p15A origin of replication from the pACYC184 plasmid. Each open reading frame is indicated by an arrow, and the origin of replication is indicated by a box. Additionally, each arrow or box is labeled with the gene name and function.

Disclosed are isolated nucleic acids comprising or encoding (i) a bacteriophage origin of replication, (ii) a bacteriophage packaging signal, and (iii) a heterologous target single-strand DNA (ssDNA) sequence of interest, where the isolated nucleic acid does not comprise or encode a plasmid origin of replication. In some forms, the isolated nucleic acid further comprises or encodes a selectable marker. In some forms, the isolated nucleic acid is single stranded. In some forms, the isolated nucleic acid is double stranded. In some forms, the isolated nucleic acid is circular. In some forms, the isolated nucleic acid is linear. In some forms, the isolated nucleic acid is circular and double stranded. In some forms, the target ssDNA sequence of interest is a scaffold sequence. In some forms, the scaffold sequence can form a 2D or 3D DNA origami structure. In some forms, the target ssDNA sequence of interest encodes bitstream data.

Also disclosed are host cell that comprise one or more of the disclosed isolated nucleic acids. In some forms, the host cell further comprises a double stranded nucleic acid helper plasmid, where the helper plasmid encodes one or more bacteriophage factors capable of packaging a single strand of the isolated nucleic acid into a bacteriophage particle, and where the helper plasmid lacks a packaging signal. In some forms, the helper plasmid, or a second plasmid, encodes one or more additional functional elements that can be incorporated into or onto the target ssDNA of interest. In some forms, the one or more functional elements are selected from the group consisting of single-guide- or crispr-RNAs (crRNA), anti-sense DNA, anti-sense RNA, one or more proteins, or a combination thereof. In some forms, the anti-sense RNA is selected from the group consisting of RNAi, miRNA, piRNA and siRNA. In some forms, the one or more proteins is a Cas protein, TAL effector protein, or zinc-finger protein. In some forms, the functional elements comprise single-guide- or crispr-RNAs (crRNA) alone or in combination with a Cas protein. In some forms, the host cell comprises a lipopolysaccharide pathway, and wherein the lipopolysaccharide pathway is disrupted. In some forms, the host cell lacks a functional RNase H gene (rnh). In some forms, the host cell expresses one or more stable strand nucleic acids that facilitate folding of the ssDNA into a 2D or 3D DNA origami structure.

Also disclosed are phagemids comprising the nucleic acid sequence of any one of SEQ ID NO:1, or 4-7, or a variant thereof with at least 75%, 80%, 85%, 90%, or 95% sequence identity to any one of SEQ ID NO:1, or 4-7. Also disclosed are phagemids comprising the backbone of SEQ ID NO:1 or 4-7, where a target single-strand DNA (ssDNA) sequence of interest is inserted into the backbone or substituted for an existing sequence without disrupting the bacteriophage origin of replication or sequence encoding the bacteriophage packaging signal.

Also disclosed are variants of a phagemid of any one of SEQ ID NO:1 or 4-7 comprising a nucleic acid sequence encoding a bacteriophage origin of replication, absence of a plasmid origin of replication, and optionally nucleic acid sequences encoding a selectable marker and/or a target single-strand DNA (ssDNA) sequence of interest. In some forms, the bacteriophage origin of replication is substituted with an alternative origin of replication, any selectable marker is substituted with an alternative selectable marker or deleted, any target single-strand DNA (ssDNA) sequence of interest is substituted with an alternative target single-strand DNA (ssDNA) sequence of interest or deleted, or a combination thereof relative to SEQ ID NO:1 or 4-7.

Also disclosed are plasmids comprising the nucleic acid sequence of SEQ ID NO:8, or a variant thereof with at least 75%, 80%, 85%, 90%, or 95% sequence identity to SEQ ID NO:8.

Also disclosed are methods of assembling two or more nucleic acid sequences to form a long single-stranded nucleic acid scaffold sequence for a nucleic acid nanostructure, comprising the steps of (a) mixing two or more nucleic acids to create a reaction mix, and (b) producing a long single-stranded nucleic acid scaffold sequence from the reaction mix using asymmetric Polymerase Chain Reaction (aPCR), where the two or more nucleic acids comprise (i) the nucleic acid sequence corresponding to the origin of replication from a class 1 filamentous bacteriophage; and (ii) one or more naturally or non-naturally occurring nucleic acid sequences of between 1 and 1,000,000 nucleotides in length; and (iii) optionally a nucleic acid sequence corresponding to one or more selection markers, where the long single-stranded nucleic acid scaffold comprises the one or more naturally or non-naturally occurring nucleic acid sequences within the reaction mix.

In some forms, the step of (b) producing a long single-stranded nucleic acid from the reaction mix using aPCR further comprises mutagenizing the long single-stranded nucleic acid. In some forms, mutagenizing the long single-stranded nucleic acid comprises exposure to an agent selected from $MnSO_4$, caffeine, or Ultra Violet (UV) light. In some forms, the single-stranded nucleic acid is complementary by 1, 2, 3, 4, 5, or 6 nucleotides, or greater than 6 nucleotides, to a second single-stranded nucleic acid generated by asymmetric PCR. In some forms, long single-stranded nucleic acid scaffold sequence is a phagemid of between 400 and 1,000,000 nucleotides in length. In some forms, the origin of replication from a class 1 filamentous bacteriophage is the 427 nucleotide f1-origin of replication. In some forms, the nucleic acid sequence corresponding to one or more selection markers is the 1,249-nt ampicillin resistance cistron. In some forms, the method further comprises a step of (c) producing a double-stranded nucleic acid corresponding to the long single stranded nucleic acid sequence using a polymerase enzyme. In some forms, complementarity exists on two regions of the second strand to delete or remove sequences from a plasmid. In some forms, the method further comprises a step of (d) encapsulating the long single-stranded nucleic acid scaffold sequence within a bacteriophage particle, where the nucleic acid within the bacteriophage particle comprises less than 10%, less than 5%, preferably less than 1% weight:weight of double-stranded DNA.

Also disclosed are methods for the in vivo production of a long single-stranded nucleic acid scaffold sequence of between 1 and 1,000,000 nucleotides in length, comprising the steps of (a) producing a long single-stranded nucleic acid sequence that is a scaffold for a nucleic acid nanoparticle formation within an microorganism; (b) packaging the long single-stranded nucleic acid scaffold sequence within a bacteriophage particle within the microorganism; and (c) isolating the long single-stranded nucleic acid scaffold sequence from the bacteriophage particle. In some forms, the method further comprises a step of (d) folding the long single-stranded nucleic acid scaffold sequence into a nucleic acid nanoparticle.

In some forms, the step of (c) isolating the long single-stranded nucleic acid scaffold sequence from the bacteriophage particle comprises or consists of harvesting phage particles directly from clarified growth media. In some forms, the harvesting comprises or consists of (i) buffer-exchanging the clarified growth media; and (ii) concentrating the phage particles. In some forms, the folding does not require removal of double-stranded DNA. In some forms, the microorganism is selected from the group consisting of a bacterium, a protozoan, a fungi, and an algae. In some forms, the method further comprises the step of isolating the single-stranded nucleic acid scaffold sequence from the microorganism. In some forms, the step of isolating the single-stranded nucleic acid scaffold sequence from the microorganism comprises (i) lysing the organism to create a lysate; and (ii) optionally isolating the DNA origami nanoparticle from the lysate. In some forms, folding the nanoparticle comprises incubating the organism at a temperature that enables hybridization and folding of the ssDNA scaffold into a nanoparticle. In some forms, the temperature that enables hybridization and folding of the DNA scaffold into a nanoparticle is 37 degrees C. In some forms, the temperature that enables hybridization and folding of the DNA scaffold into a nanoparticle is room temperature or 21 degrees C. In some forms, the temperature that enables hybridization and folding of the DNA scaffold into a nanoparticle is any target temperature based on the hybridization properties of the sequence and staple strands that may be LNA, PNA, RNA, or DNA.

In some forms, the single-stranded nucleic acid sequence is produced in the organism at a temperature that does not facilitate hybridization or folding of the ssDNA scaffold into a nanoparticle, such that hybridization and folding are initiated by exposure of the organism to the required temperature. In some forms, the microorganism is a bacteria. In some forms, the bacteria is a strain of *Escherichia coli*. In some forms, the nucleic acid nanostructure or nanoparticle includes paranemic crossover motifs. In some forms, the crossover motifs are PX-only, DX-only, or some combination of PX- and DX-crossovers. In some forms, the single-stranded nucleic acid is directly folded into a nucleic acid nanoparticle or nanostructure without removal of double stranded DNA.

In some forms, folding the single stranded nucleic acid into a nucleic acid nanostructure or nanoparticle is carried out using a buffer. In some forms, the folding buffer comprises 1-, 2-, 21, 22- or more than 22-fold molar excess of one or more staple strands. In some forms, the folding buffer comprises 2, 3, 4, 5, 6, 7, 8, 9, 10, 11, 12, 13, 14, 15, 16, 17, 18, 19, 20 or greater than 20 mM $MgCl_2$. In some forms, the folding buffer further comprises sodium dodecyl sulfate, triton x100, or other detergents. In some forms, the single-stranded nucleic acid sequence comprises digital bitstream data. In some forms, the single-stranded nucleic acid sequence comprises a bait or capture sequence that can anneal or bind biological materials including DNA, RNA, or nucleic-acid-binding proteins. In some forms, the bait or capture sequence can anneal or bind a gene editing ribonucleoprotein complex. In some forms, the single-stranded nucleic acid sequence comprises the scaffold sequence of a nucleic acid nanoparticle that can fold in the absence of one or more staple sequences.

Also disclosed are nucleic acid nanoparticles folded from a single single-stranded nucleic acid sequence made according to the disclosed methods. Also disclosed are single-stranded nucleic acid scaffold sequences produced according to the disclosed methods. In some forms, the nucleic acid sequence encodes digital bitstream data. In some forms, the nucleic acid scaffold sequence comprises a bait or capture sequence that can anneal or bind biological materials including DNA, RNA, or nucleic-acid-binding proteins. In some forms, the nucleic-acid-binding protein is specific for a gene editing ribonucleoprotein complex. In some forms, the scaffold sequence folds into a nucleic acid nanoparticle without staples. In some forms, the scaffold sequence folds into a nucleic acid nanoparticle with 1, 2, 3, or more than 3 staples. In some forms, the scaffold sequence folds into a nucleic acid nanoparticle with 1, 2, 3, or more than 3 staples using either PX-only, DX-only, or some combination of PX- and DX-crossovers.

Also disclosed are microorganisms that produces pure single stranded nucleic acid of a user-defined length and sequence, the microorganism comprising (a) a phagemid, and (b) a double stranded nucleic acid helper plasmid, where the phagemid comprises a phage origin of replication and a single stranded nucleic acid scaffold of a user-defined length and sequence and lacks a plasmid origin or replication, and where the helper plasmid comprises genes of the corresponding phage and optionally lacks the phage packaging signal. In some forms, the origin of replication is the f1 or M13 origin of replication. In some forms, the plasmid lacks the genes encoding the major coat protein. In some forms, the only phage genes the plasmid comprises correspond to those required for replication of the phagemid. In some forms, the plasmid encodes one or more transcribable RNAs that can serves as one or more staples of the single stranded nucleic acid scaffold. In some forms, the microorganism comprises two or more transcribable RNAs, where the transcribable RNAs are separated by transcription terminators and initiated by transcription promoters. In some forms, the transcribable RNAs comprise a ribozyme or ribozymes that cleaves the RNA into two or more staple sequences. In some forms, the ribozymes are Twister and Pistol ribozymes that cleave near their 5' and 3' ends, respectively. In some forms, the microorganism comprises the genome of the M13 bacteriophage.

Also disclosed are bacteriophages produced by any of the disclosed microorganisms. In some forms, the total amount of DNA within the bacteriophage particle comprises less than 10%, less than 5%, preferably less than 1% weight:weight of double-stranded DNA. In some forms, the bacteriophage genome is mutated to disrupt the capsid package to directly export ssDNA to the media.

I. Definitions

The terms "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides (DNA) or ribonucleotides (RNA), or analogs or modified nucleotides thereof, including, but not limited to locked nucleic acids (LNA) and peptide nucleic acids (PNA). An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides. In some cases nucleotide sequences are provided using character representations recommended by the International Union of Pure and Applied Chemistry (IUPAC) or a subset thereof. IUPAC nucleotide codes used herein include, A=Adenine, C=Cytosine, G=Guanine, T=Thymine, U=Uracil, R=A or G, Y=C or T, S=G or C, W=A or T, K=G or T, M=A or C, B=C or G or T, D=A or G or T, H=A or C or T, V=A or C or G, N=any base, "." or "-"=gap. In some embodiments the set of characters is (A, C, G, T, U) for adenosine, cytidine, guanosine, thymidine, and uridine respectively. In some embodiments the set of characters is (A, C, G, T, U, I, X, Ψ, R, Y, N) for adenosine, cytidine, guanosine, thymidine, uridine, inosine, uridine, xanthosine, pseudouridine respectively. The modified sequences, non-natural sequences, or sequences with modified binding, may be in the genomic, the guide or the tracr sequences.

The terms "staple strands" or "helper strands" are used interchangeably. "Staple strands" or "helper strands" refer to oligonucleotides that work as glue to hold the scaffold nucleic acid nanostructure in its three-dimensional geometry. Additional nucleotides can be added to the staple strand at either 5' end or 3' end, and those are referred to as "staple overhangs." Staple overhangs can be functionalized to have desired properties such as a specific sequence to hybridize to a target nucleic acid sequence, or a targeting element. In some instances, the staple overhang is biotinylated for capturing the DNA nanostructure on a streptavidin-coated bead. In some instances, the staple overhang can be also modified with chemical moieties. Non-limiting examples include Click-chemistry groups (e.g., azide group, alkyne group, DIBO/DBCO), amine groups, and Thiol groups. In some instances some bases located inside the oligonucleotide can be modified using base analogs (e.g., 2-Aminopurine, Locked nucleic acids, such as those modified with an extra bridge connecting the 2' oxygen and 4' carbon) to serve as linker to attach functional moieties (e.g., lipids, proteins). Alternatively DNA-binding proteins or guide RNAs can be used to attach secondary molecules to the DNA scaffold.

The terms "scaffolded origami," "origami" or "nucleic acid nanostructure" are used interchangeably. They refer to a long, single strand of polynucleotide (scaffold strand) that is folded into desired shapes on the order of about 10 nm to a micron, or more. In some embodiments, nucleic acid scaffold sequences are folded into nucleic acid nanostructures by hybridization to small nucleic acid "staple sequences." Alternatively, single-stranded nucleic acid scaffolds can be designed to fold into an origami object without helper strands, for example, using parallel or paranemic crossover motifs. The scaffolded origami or origami can be composed of deoxyribonucleotides (DNA) or ribonucleotides (RNA), or analogs or modified nucleotides thereof, including, but not limited to locked nucleic acids (LNA) and peptide nucleic acids (PNA). A scaffold or origami composed of DNA can be referred to as, for example a scaffolded DNA origami or DNA origami, etc. It will be appreciated that where compositions, methods, and systems herein are exemplified with DNA (e.g., DNA origami), other nucleic acid molecules can be substituted. Typically, the nucleic acid nanostructures are nucleic acid objects made from scaffold nucleic acid with or without staple nucleic acid sequences, or from encapsulated nucleic acid of any arbitrary length/form, or any combinations thereof. The nucleic acid nanostructure can be composed of deoxyribonucleotides (DNA) or ribonucleotides (RNA), or analogs or modified nucleotides thereof, including, but not limited to locked nucleic acids (LNA) and peptide nucleic acids (PNA).

The term "single stranded nucleic acid scaffold sequence" refers to a single-stranded nucleic acid sequence that is routed throughout the entire structure of a nucleic acid nanostructure. The nucleic acid structure assemblies optionally include oligonucleotide staple strands that hybridize to the scaffold sequence and create the polyhedral structure. When the polyhedral nucleic acid assemblies do not include staple strands, the scaffold sequence hybridizes to itself to create the nucleic acid nanostructure.

The terms "nucleic acid overhang," "DNA overhang tag," and "staple overhang tag," and "address tag" are used interchangeably to refer to any additional nucleotides added to the nucleic acid nanostructures that can be functionalized. In some embodiments, these additional nucleotides are added to the staple strand. In some instances, the overhang tag contains one or more nucleic acid sequences that encode metadata for the associated nucleic acid nanostructures. In some instances, the overhang tag contains sequences designed to hybridize other nucleic acid sequences such as those on tags of other nucleic acid nanostructures. In other instances, the overhang contains one or more sites for conjugation to a molecule. For example, the overhang tag can be conjugated to a protein, or non-protein molecule, for example, to enable affinity-binding of the nucleic acid nanostructures. Exemplary proteins for conjugating to overhang tags include biotin and antibodies, or antigen-binding fragments of antibodies.

The term "bit stream encoded sequence" is any nucleic acid sequence that encodes for data to be stored. Bit stream-encoded nucleic acid can be in the form of a linear nucleic acid sequence, a two-dimensional nucleic acid object or a three-dimensional nucleic acid object. Bit stream-encoded nucleic acid can include a sequence that is synthesized, or naturally occurring. The term "bit" is a contraction of "binary digit." Commonly "bit" refers to a basic capacity of information in computing and telecommunications. A "bit" conventionally represents either 1 or 0 (one or zero) only, though other codes can be used with nucleic acids that contain 4 nucleotide possibilities (ATGC) at every position, and higher-order codecs including sequential 2-, 3-, 4-, etc. nucleotides can alternatively be employed to represent bits, letters, or words.

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "polypeptide" includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term, "isolated nucleic acid" refers to a nucleic acid that is separated from other nucleic acid molecules that are present in a naturally-occurring genome, including nucleic acids that normally flank one or both sides of the nucleic acid in a naturally-occurring genome. An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a bacteriophage, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The term "pure" and "purified" and like terms relate to the isolation of a molecule or compound in a form that is substantially free (at least 60% free, preferably 75% free, and most preferably 90% free) from other components normally associated with the molecule or compound in a native environment, or of a molecule or compound relative to one or more other components prepared in one system relative to preparation in another system. For example, one system may produce a desired nucleic acid (e.g., a single stranded nucleic acid) at a higher purity relative to another component (e.g., double stranded nucleic acid) when compared to another system of production.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "percent (%) sequence identity" is defined as the percentage of nucleotides or amino acids in a candidate sequence that are identical with the nucleotides or amino acids in a reference nucleic acid or amino acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

II. Methods and Systems for Microbial Production of Pure Single Stranded Nucleic Acid Scaffold Sequences Pure single-stranded DNA (ssDNA) can be produced directly from bacteria using an engineered M13 phage that is produced from a plasmid that only encodes double-stranded DNA (dsDNA) and a phagemid plasmid that only contains a single f1-origin of replication and the packaging signal. The phage particles are produced containing only the ssDNA that has the f1-origin. The phagemid DNA can additionally contain an insert of DNA of any user-defined size and sequence that will be produced with the f1-origin as pure ssDNA and released as phage particles into the media. The phage particles are easy to purify away from the *E. coli* and the contaminating dsDNA and are produced in very high yield compared to other methods of ssDNA production known in the art.

The generation of a platform for the production of pure ssDNA direct from bacteria allows for applications in building DNA, RNA, or protein libraries, single-cell barcoding, RNA sequence complementarity, gene circuit switches, and as a bait for nucleic acid binding proteins and binding to complementary DNA or RNA designed sequences.

In some embodiments, the target ssDNA sequence is cloned directly to the f1-origin with a selection marker, such as the ampicillin resistance gene. In other embodiments, the target ssDNA sequence is cloned directly to the f1-origin without a selection marker. For example, the absence of a selection marker can further reduce sequence requirements and completely unlink the phagemid from biological sequences. Further, ssDNA production directly from bacterial allows for the cloning and scaling of information encoded in bacteria to be extruded to surrounding media for subsequent purification or processing.

Methods for producing long single-stranded nucleic acid scaffold sequences of sufficient purity for directly folding into nucleic acid nanostructures are described.

Typically, the methods include one or more of the following steps:

(A) Providing a target nucleic acid scaffold sequence in the form of a long single stranded nucleic acid;

(B) Forming a phagemid molecule including the long single stranded target nucleic acid sequence;

(C) Packaging the phagemid into a bacteriophage particle in the absence of contaminating nucleic acid, such as double-stranded DNA;

(D) Isolating the bacteriophage;

(E) Optionally isolating the long single stranded target nucleic acid sequence from the bacteriophage; and (F) Creating a nucleic acid nanostructure including the target sequence.

The long single stranded target nucleic acid sequence can be of sufficient purity to be folded into a nucleic acid nanostructure without the need for subsequent purification steps, for example, without the need to remove contaminating dsDNA.

Methods for the in vivo production of a single-stranded nucleic acid sequence that is a scaffold for a nucleic acid nanoparticle are also described.

The methods include the step of producing a single-stranded nucleic acid sequence that is a scaffold for a nucleic acid nanoparticle formation within a microorganism. Exemplary microorganisms include a bacterium, a protozoan, a fungi, and an algae. A preferred micro-organism is a bacteria, such as an *Escherichia coli* strain.

The methods optionally include the step of isolating the single-stranded nucleic acid scaffold sequence from the microorganism. The step of isolating the single-stranded nucleic acid scaffold sequence from the microorganism can include lysing the organism to create a lysate; and optionally isolating the DNA origami nanoparticle from the lysate. The methods optionally also include the step of folding the single-stranded nucleic acid scaffold sequence into a nucleic acid nanoparticle.

Folding the nanoparticle typically includes incubating the organism or lysate or isolate at a temperature that enables hybridization and folding of the ssDNA scaffold into a nanoparticle. In some embodiments, the temperature that enables hybridization and folding of the DNA scaffold into a nanoparticle is 37 degrees C. Typically, the single-stranded nucleic acid sequence is produced in the organism at a temperature that does not facilitate hybridization or folding of the ssDNA scaffold into a nanoparticle, such that hybridization and folding are initiated by exposure of the organism to the required temperature. In some embodiments, the nucleic acid nanoparticles includes paranemic (PX) cross-over motifs, or double-crossover (DX) motifs.

Figure 3:
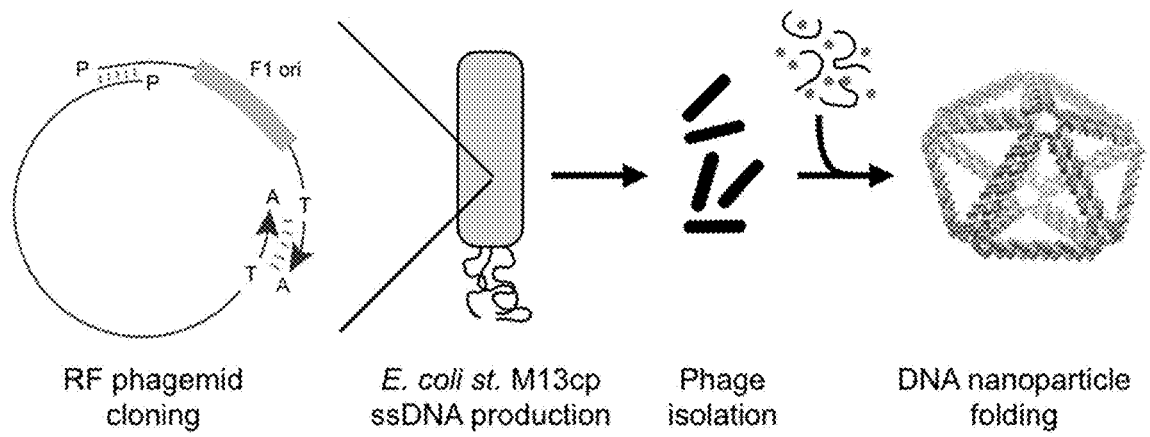
FIG. 3 is a schematic representation of the work flow for selection and purification of ssDNA from plasmid insertion, to phage isolation, to nanoparticle folding, by adding staples, ions, and slowly annealing.
Figure 4:
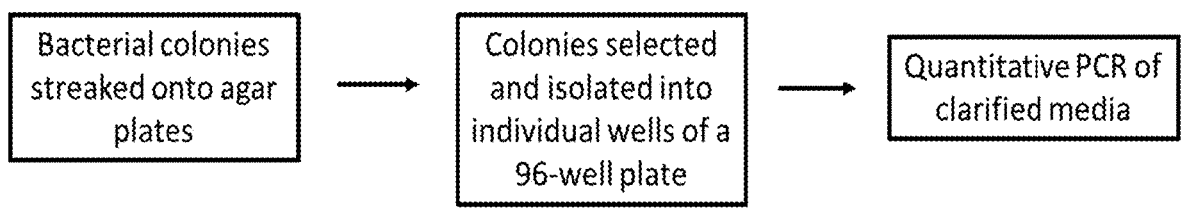
FIG. 4 is a flowchart representing how individual colonies are selected and placed into individual wells of a 96- or 384-well plate, grown up in TB, spun down, and the supernatant media is tested for ssDNA by quantitative PCR.
Figure 5:
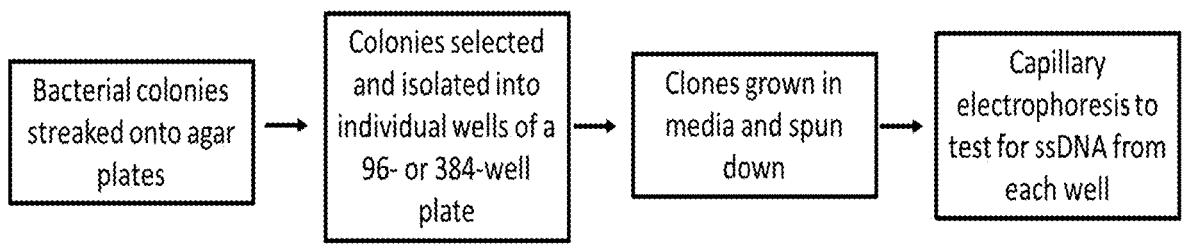
FIG. 5 is a flowchart representing how individual colonies are selected and placed into individual wells of a 96- or 384-well plate, grown up in TB, spun down, and the supernatant media is tested for ssDNA by capillary electrophoresis.
Figure 6:
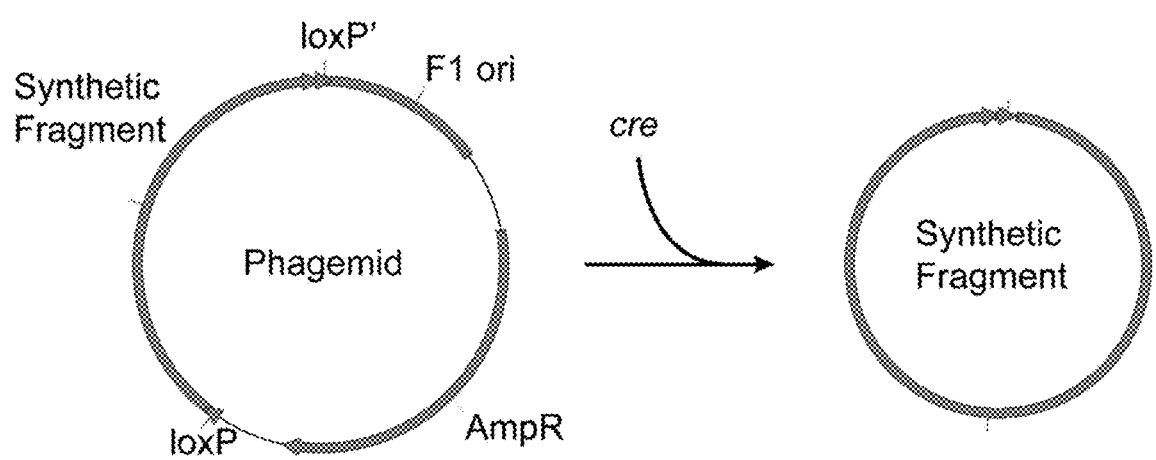
FIG. 6 is a schematic representation of the production of recombined ssDNA production in microorganisms using loxP recombination with cre recombinase to remove extraneous sequences.

Methods for the in vivo production of nucleic acid nanoparticles are provided, including the steps of producing a single-stranded nucleic acid sequence that is a scaffold for a nucleic acid nanoparticle formation within a bacteriophage particle; and folding the single-stranded nucleic acid scaffold into a nucleic acid origami nanoparticle. The methods optionally include the step of isolating the DNA origami nanoparticle from the microorganism. The described methods are depicted in FIGS. 3, 4 and 5. Exemplary methods of screening for production of nanostructures are depicted in FIGS. 8A, 8B, 9A, 9B and 11A-11D.

In some embodiments, the single-stranded nucleic acid is directly folded into a nucleic acid nanoparticle without removal of double stranded DNA.

Generally, folding of the single stranded nucleic acid into a nucleic acid nanostructure is carried out using a suitable buffer.

Exemplary folding buffers include 1-, 2-, 21, 22- or more than 22-fold molar excess of staple strands. Exemplary buffers also include a suitable ionic concentration to facilitate folding, such as 2, 3, 4, 5, 6, 7, 8, 9, 10, 11, 12, 13, 14, 15, 16, 17, 18, 19, 20 mM, or greater than 20 mM $MgCl_2$. Exemplary buffers also include sodium dodecyl sulfate, triton ×100, or other detergents.

A. Providing a Target Nucleic Acid Sequence

The desired target ssDNA can be any desired nucleic acid sequence. For example, the ssDNA sequence can be one that is or forms a scaffold structure, stores data, encodes genetic information, or carries out another biological or non-biological function. Thus, the disclosed compositions and methods typically include providing a target nucleic acid sequence, optionally, one that can be folded into a nucleic acid nanostructure. Many known methods are available to design scaffolded nucleic acid sequences, and any such scaffold sequences can used in the disclosed target ssDNA sequences, and the compositions and methods associated therewith.

In some embodiments, the target ssDNA is the sequence of DNA origami structure. Exemplary methods for designing and exemplary sequences for forming DNA origami include those described by Veneziano, et al., (Veneziano, et al., Science, 352, 1534 (2016)), Benson E et al (Benson E et al., Nature 523, 441-444 (2015)), Rothemund P W et al (Rothemund P W et al., Nature. 440, 297-302 (2006)), Douglas S M et al., (Douglas S M et al., Nature 459, 414-418

(2009)), Ke Y et al (Ke Y et al., Science 338: 1177 (2012)), Zhang F et al (Zhang F et al., Nat. Nanotechnol. 10, 779-784 (2015)), Dietz H et al (Dietz H et al., Science, 325, 725-730 (2009)), Liu et al (Liu et al., Angew. Chem. Int. Ed., 50, pp. 264-267 (2011)), Zhao et al (Zhao et al., Nano Lett., 11, pp. 2997-3002 (2011)), Woo et al (Woo et al., Nat. Chem. 3, pp. 620-627 (2011)), and Torring et al (Torring et al., Chem. Soc. Rev. 40, pp. 5636-5646 (2011)), Said, et al., *Nanoscale*, 5(1):284-90 (2013), and Brown, et al., Nanoscale, 7, 16621-16624 (2015) each of which are incorporated by reference herein in its entirety. Strategies for designing nucleic acid nanostructures of various shapes and sizes are also described in WO 2017/189870, which is specifically incorporated by reference herein in its entirety, and can be used to design target nucleic acid scaffold sequences incorporated into the disclosed phagemids for improved production and/or purity of the desired ssDNA.

In some embodiments, the single-stranded nucleic acid targets sequence is a user-defined nucleic acid that includes one or more pieces of enclosed digital bitstream data. Arbitrary sequence can be used to encode digital files, packaged into phage that can be desiccated, silicanized, and can display molecular identifiers. Strategies for data storage using nucleic acid scaffold sequences are described in more detail in WO 2017/189914, which is specifically incorporated by reference herein in its entirety, and can be used to design target nucleic acid scaffold sequences incorporated into the disclosed phagemids for improved production and/or purity of the desired ssDNA.

For example, nucleic acid nanostructures formed from single-stranded nucleic acid scaffolds of up to tens of kilobases (kb) are folded into well-defined, discrete structures that serve as nucleic acid memory objects (NMOs). Distinct packages of information can be provided as three-dimensional nucleic acid structures with multiple faces that include one or more specific sequence tags. Through manipulation of NMO structures, the methods enable the partitioning, association, and re-assortment of information encoded in the single-stranded nucleic acid scaffold backbone of each NMO. Information retrieval can be achieved rapidly by sequencing. Therefore, these compositions enable rapid and efficient organization and access of "memory" information stored within NMOs.

The information can include any desired media in any format. In some embodiments, a desired media includes any kind of media useful to communicate information. The information or media can be obtained from any source known in the art, including exemplary print media, such as books, magazines, newspapers, etc.), televisual media, including movies, video games, televised news, cartoons, images, etc.), audible media, such as music, or radio broadcasts, cellular phone data, various kinds of software, and media available on the Internet, such as media in an html format, databases, government or private records documents, financial data or ledgers, or any other digital format, or databases of cDNA or natural DNA sequences. Internet data or other information storage data including data with properties that need to be classified automatically through machine learning or other classification strategies may also benefit from the proposed molecular memory approach. Monitoring or profiling data from flights, transportation, military, or other sources may also be of use, together with financial data, banking data, health records, patient data, and personnel-related data, and autonomous vehicle data. For example, in some embodiments, the desired media is the text of a book, or the text of one or more chapters of a book, or the text of one line of one page of a book.

In some embodiments, a portion or portions of a digital format of information, such as an html format of information or any other digital format such as a book with text and/or images, audio, or movie data, is converted to bits, i.e. zeros and ones. In some embodiments, the information can be otherwise converted from one format (e.g., text) to other formats such as through compression by Lempel-Ziz-Markov chain algorithm (LZMA) or other methods of compression, or through encryption such as by Advanced Encryption Standard (AES) or other methods of encryption. Other formats of information that can be converted to bits are known to those of skill in the art.

In other embodiments, the single-stranded nucleic acid target sequence comprises a bait or capture sequence that can anneal or bind biological materials including DNA, RNA, or nucleic-acid-binding proteins. An exemplary bait or capture sequence can anneal or bind a gene editing ribonucleoprotein complex.

Scaffold nucleic acid sequences and oligonucleotide staple sequences can be synthesized or purchased from numerous commercial sources. In some embodiments, the scaffold nucleic acid sequence is the M13mp18 single-stranded DNA scaffold. The M13mp18 ss DNA can be purchased from multiple commercial sources, including New England Biolabs (Cat #N4040S) or from Guild Biosciences for various M13mp18 size.

Typically, scaffold DNA of the desired length is produced using polymerase chain reaction (PCR) methodologies. Standard methods for PCR are known in the art. In some embodiments, the nucleic acid scaffold sequences are produced using asymmetric PCR (aPCR). When aPCR amplification is used, oligonucleotide primers can be designed to generate many different scaffold lengths. Therefore, in some embodiments, the scaffold having a desired length is produced using one or more custom oligonucleotides. When the template scaffold nucleic acid is known, a set of known oligonucleotides can be used. For example, when the scaffold nucleic acid is known, the primers can be used to design scaffolds of desired lengths.

In some embodiments modified dNTPs (examples of modified dNTPs include, but are not limited to dUTP, Cy5-dNTP, biotin-dNTPs, alpha-phosphate-dNTPs) are used for amplification of the ssDNA scaffold. In other embodiments the template use is the Lambda phage that can be purchased from different commercial sources, including New England Biolabs (Cat #N3011S). In other embodiments, the nucleic acid nanostructures are produced using digestion of the template DNA to form a scaffold nucleic acid of the desired length. In certain embodiments, a combination of PCR and digestion methods is used to produce scaffold single-stranded nucleic acid of the desired length.

In some embodiments, the single-stranded nucleic acid target sequence is designed to include a nucleic acid scaffold sequence that can fold into a nucleic acid nanoparticle in the absence of staple sequences.

B. Constructing Phagemids

The methods can include assembling nucleic acid "target" sequences into a phagemid. Typically, the phagemid includes the f1-origin of replication, the target scaffold nucleic acid sequence, and optionally one or more selection markers. Phagemids can be produced using any techniques known in the art. Preferably, phagemid assembly is accomplished by a technique that ensures high yield circular phagemid genomes for successful transformation. Such techniques include, for example, Gibson assembly, standard restriction cloning, BioBrick, BglBrick, or other idempotent cloning techniques, or Type IIS cloning such as GoldenGate, or GoldenBraid cloning, or restriction free cloning.

In a particular embodiment, the phagemid is produced using asymmetric polymerase chain reaction (aPCR).

In an exemplary method, single stranded DNA can be generated by first amplifying the desired f1 sequence with polymerase (e.g., Phusion™), followed by gel purification and silica column cleanup. Asymmetric polymerase chain reaction can be subsequently applied using, for example, 200 ng of purified dsDNA and 1 uM of the 5'-phosphorylated 3' reverse primer with QuantaBio Accustart HiFi polymerase.

The beta-lactamase (bla) ampicillin resistance gene (ApR) (also referred to herein as AmpR) and its promoter and terminator sequences can be amplified from, for example, the widely available pUC19 plasmid using Phusion™ polymerase using a 3' reverse primer and a 5' primer that is additionally extended on the 5' side by the reverse complement of the reverse primer of the f1 fragment. The amplicon can be gel- and column-purified.

Asymmetric PCR can be used to amplify single-stranded DNA using, for example, 200 ng of purified amplicon as a template with QuantaBio AccuS tart HiFi buffer and enzyme and 1 uM 5'-phosphorylated reverse primer. The two single-stranded DNA products can then be mixed. For example, in an exemplary embodiment two single-stranded DNA products can be mixed in, for example, a 1:1 molar ratio and the ssDNA converted to dsDNA using Phusion polymerase. Amplification can be carried out using flanking forward and reverse phosphorylated primers, and subsequently purified. Blunt-end ligation can be used to close the plasmid. For example, in some embodiments, blunt-end ligation is carried out using T4 DNA ligase (NEB) in 1×T4 DNA ligation buffer with, for example, 30 ng of amplified DNA incubated at room temperature overnight.

*E. coli* cells, for example, strain DH5a FIQ, can be made competent by washing log-phase grown cells in ice cold 100 mM $CaCl_2$. Competent cells can be transformed with plasmids, for example 1 ng of helper plasmid DNA and 2 μL of plasmid DNA ligation mix were added to 20 μL of cells. Cells can be subjected to a series of heating and cooling steps and ultimately plated on media plates. For example, in some embodiments, cell are incubated on ice for 30 minutes, heat shocked at 42° C. for 45 seconds, put back on ice before adding pre-warmed SOB media and shaken at 37° C. for 1 hour. 100 μL can be plated evenly across a Luria Agar (LA) media plate made with 100 μg/mL ampicillin and 15 μg/mL chloramphenicol.

Next, colonies can be selected and cultured. For example, in some embodiments, single, individual colonies are selected and grown in 5 mL of Terrific Broth (TB) supplemented with 1% glycerol for 36 hours at 37° C. 1 mL of the growth is then removed to a 1.5 mL spin column and spun in a centrifuge at 4,000 rpm for 5 minutes. Supernatant is removed and placed in a new 1.5 mL spin column and spun at 4,000 rpm for an additional 10 minutes. 1 μL of the supernatant is added to 20 uL of nuclease-free water and heated to 95 C for 5 minutes. 1 μL of the heated solution is added to a Phusion PCR mix containing enzyme, buffer, nucleotides, and forward and reverse primers used to generate the plasmid. Positive colonies are determined by the presence of the amplicon from the media as determined by agarose gel. Positive colonies can be sequenced.

In some embodiments, single-stranded nucleic acid can be used to further miniaturize the phagemid genome to only contain the phage origin of replication (e.g., f1) and target nucleic acid sequence without a selection marker.

An exemplary target sequence is a nucleic acid strand encoding the bitstream data. In an illustrative proof-of-principle, the bitstream data corresponds to a section of text from the literary work "The Crucible." In an exemplary method, a forward primer from the 5' of the Crucible extends 5' to include 20 nucleotides at the 3' end of the f1 and a reverse primer is generated on the next 20 nucleotides 5'. These primers are used in an aPCR reaction to amplify ssDNA encoding one strand of the phagemid. In a separate reaction, the reverse complement of the bridging primer is in 5-fold excess while the reverse primer was forward primer 3' of the bridging primer and again amplified by asymmetric PCR. The purified ssDNA can be annealed in, for example, equimolar amounts, ligated, and transformed into the helper strain. The transformation can be streaked to single colonies. Colonies can be tested for the new sPhage production that is minimized to include just the f1 and the bitsteam data (e.g., the Crucible line).

C. Production of Phage (sPhage)

Recombinant phage (also referred to as "synthetic phage" and "sPhage") producing colonies, as judged by positive PCR, gel visualization, and sequencing, can be grown in, for example, 5 mL TB supplemented with glycerol, as recommended by the manufacturer (Sigma-Aldrich, Inc.), inoculated by a single colony from an Luria-Agar plate. The colony can be grown in, or example, a 15 mL culture tube shaken at 200 RPMs at 37° C. for 36-48 hours. The culture can then be spun down in, for example, 2 mL centrifuge tubes at 4,000 RPMs for 5 minutes. The supernatant can be removed to a fresh tube and spun at 4,000 RPMs for an additional 10 minutes. The supernatant (approximately 5 mL) can be refrigerated until ready for DNA preparation.

SPhage particles containing the f1-origin can be precipitated, for example, by adding 10% acetate pH 5.2 and 2.5 volumes of 100% ethanol and freezing at −20 C for at least 1 hour, or, alternatively, by adding 6% polyethylene glycol 8000 (PEG 8000) final concentration and shaking at 37 C for 30 minutes. Precipitated sPhage can be pelleted, for example, by centrifugation at 13,000 RPMs for 10 minutes in PEG 8000 or at 4 C at 13,000 RPMs for 30 minutes in ethanol. Supernatant can be removed from the pellet. The sPhage pellet can be brought up in Tris-buffered 2% sodium dodecyl sulfate (SDS) and heated to 70 C for 30 minutes.

The lysed sPhage can be run through a silica-based column (Qiagen EndoFree MaxiPrep, ThermoFisher HiPure) to purify the DNA following the manufacturers' protocols. DNA can be eluted in 10 mM Tris-HCl elution buffer.

1. Direct Extrusion of the ssDNA into the Media without a Phage Intermediate

In some embodiments, the M13 system is engineered to facilitate for direct extrusion of the target scaffold ssDNA into the growth media without a phage intermediate. For these systems, high-throughput testing of media-exported ssDNA can be carried using qPCR, or by capillary electrophoresis. For example, in some embodiments, G8P is targeted for mutation on the helper strain plasmid to disrupt the coat protein packaging of the ssDNA genome, allowing for the release of the ssDNA into the media. In some embodiments, the ssDNA accumulates in the cell by only expressing G2P, G5P, and G10P on the helper strain plasmid and no other M13 proteins.

a. High-Throughput Testing of Media-Exported ssDNA Using qPCR

In some embodiments, high-throughput testing of media-exported ssDNA is carried out using qPCR, or by capillary electrophoresis.

Colonies can be selected and grown in media. In an exemplary embodiment, colonies, for example, 88 or 376 colonies, are individually selected and placed in media, for example a 96-well or 384-well plate containing 50 μL of media, and grown for, for example, 8 hours at 37 C while shaking. After, for example, 5 to 8 hours, the plate is centrifuged for 10 minutes at 4000 RPMs. The media supernatant can transferred, e.g. pipetted to a different 96- or 384-well plate compatible with the qPCR machine (Roche Lightcycler or ThermoFisher QuantStudio 6 or 7). 1-20 uL of the cleared media can be added with 1× to 2× final concentration of SybrGreen I, SybrGreen II, SybrGold, SybrSafe or similar DNA or RNA fluorescent stain. In some cases, such as with SybrSafe, the emission wavelength is different for dsDNA than for ssDNA, and thus production of ssDNA can be monitored while simultaneously monitoring dsDNA contamination from *E. coli* cell lysis. The remaining 8 wells of the plate can be used as a ssDNA standard curve in the same media but without bacterial culture. The plate is heated to release the ssDNA from the sPhage, and the fluorescence measurement identifies colonies with high DNA concentrations in the clear media. Those colonies with high fluorescence are tested for satisfying the other conditions (agarose gel visualization, sequencing).

Some embodiments additionally or alternatively include sequence analysis. For example, 1 μL of the cleared media can be put in 19 μL of nuclease-free water and boiled at 95 C for 5 minutes. 1 μL of the boiled solution can be placed in each well of a TaqMan® or similar assay for quantitative measurement of the ssDNA amounts per colony for a specific sequence. Positive colonies can be selected from the plate and grown up for large-scale production.

b. High-Throughput Testing of Media-Exported s ssDNA Using Capillary Electrophoresis In some embodiments, high-throughput testing of media-exported ssDNA is carried out using qPCR, or by capillary electrophoresis. In an exemplary embodiment, machines, such as a Fragment Analyzer which relies on capillary electrophoresis, are used to quantitatively determine DNA amounts and sizes in 12 and 96 sample formats. DNA from the cleared media can be loaded to the Fragment Analyzer and visualized to determine colonies that are producing ssDNA of the expected size.

2. Mutagenesis of f1-Origin and M13 Helper Strain Plasmid to Increase ssDNA Production.

In some embodiments, mutagenesis of f1-origin and M13 helper strain plasmid is carried out to increase ssDNA production. In an exemplary embodiment, clones containing the f1-origin are mutagenized by, for example, incubation with caffeine or subjecting the clone to UV light. Alternatively, mutagenic clones are generated by using mutagenic PCR with Manganese replacing some of the Magnesium in the PCR reaction. For example, aPCR can be carried out with 1.8 mM MgSO4 and 200 μM MnSO$_4$, or some variation of Mg and Mn concentration to allow for high yield ssDNA but with lower or higher mutation numbers per amplicon, or by production in *E. coli* XL-1 red or other mutagenic strains. Assembly of the phagemid and helper strain plasmid can otherwise be as described above. Mutagenized M13 helper strain and f1-origin phagemid can be tested in high-throughput using the techniques of purification of functionalized ssDNA and ssDNA production with removal of partial components towards two goals: (1) increasing sPhage production by testing for higher concentrations of DNA in the media, and (2) the direct export of the phagemid DNA into the media without the intermediate assembly of phage particles, without the intermediate step of heating.

3. Purification of Functionalized ssDNA

In some embodiments, the methods include purification of functionalized ssDNA. In an exemplary embodiment, cells containing an expression plasmid for a gene editing protein Cas9 or Cpf1 and the transcription unit for the single-guide or crispr RNA (crRNA) containing a 3' extension overhang from the crRNA that is complementary to the ssDNA of the phagemid. By producing these in a cell that also contains the helper strain plasmid and the phagemid with only the f1-origin and an additional sequence that contains the sequence complementary to the overhang of the crRNA, the gene editing protein is loaded directly to the sPhage. This strategy enables both purification of the CRISPR particle, or in vivo delivery of gene editing ribonucleoprotein complex.

4. ssDNA Production with Removal of Partial Components

In some embodiments, ssDNA is produced with removal of partial components. In an exemplary embodiment, LoxP forward and reverse sites are introduced into the sequence of the phage-produced ssDNA surround sites targeted for removal. Cre recombinase enzyme is then introduced in vitro to induce recombination and splitting of the ssDNA into two circular separate strands. The methods facilitate sequence removal, and nanoparticle partitioning.

D. Isolation of Single Stranded Nucleic Acid Scaffolds and Nanostructures ssDNA produced by the bacteria can be isolated from phage particles or from the bacteria, or from the growth media.

Typically, the single stranded nucleic acid scaffold sequences are produced within phage particles in quantities far greater than can be achieved in the absence of a phage or helper microorganism. In some embodiments, the single stranded nucleic acid scaffold sequences are isolated from phage particles in a two-step process, including buffer-exchanging the media and lysing the phage, for example, by exposure to heat. In some embodiments, the single stranded nucleic acid scaffold sequences are concentrated and immediately folded into nanoparticles. Typically, the isolated nucleic acid is sufficiently free of contaminants, such as bacterial dsDNA, that folding can be achieved without the need for any purification of the nucleic acid.

In an exemplary method, phage particles are collected from the media by first purifying away from bacteria, for example, by 2 rounds of centrifugation at 4,000 RPMs for 30 minutes. The supernatant can be concentrated, for example, on a 100 kDa MWCO spin concentrator (Amicon) and brought to equivalent volumes with 1×TAE buffer with 12 mM MgCl$_2$ 3 times. Phage material can be combined with staples if needed. For example, in an exemplary embodiment, 20 nM phage material is combined with 400 nM staples in 1×TAE buffer with 12 mM MgCl$_2$ and 0.2% sodium dodecyl sulfate (SDS) in 50 μL total volume. The solution can be annealed, for example, over 13 hours from 95° C. to 24° C. and the folded particle can be run on an agarose gel with the ssDNA scaffold for reference.

The nucleic acid nanostructure typically has a defined shape and size. Typically, one or more dimensions of the nanostructure are determined by the target sequence. The methods include designing nanostructures including the target nucleic acid sequence.

The foregoing methods are exemplary and illustrative. The disclosed methods and systems can be scaled up or down depending on the application and desired volume or amount of material needed. For example, large volumes of *E. coli* producing phage can be grown in a large-scale reactor for the achieving very large quantities of the selected DNA or phage can be continuously produced in a bioreactor system.

III. Compositions

The compositions described below include materials, compounds, and components that can be used for the disclosed methods. Various exemplary combinations, subsets, interactions, groups, etc. of these materials are described in more detail above. However, it will be appreciated that each of the other various individual and collective combinations and permutations of these compounds that are not described in detail are nonetheless specifically contemplated and disclosed herein. For example, if one or more nucleic acid nanostructures are described and discussed and a number of substitutions of one or more of the structural or sequence parameters are discussed, each and every combination and permutation of the structural or sequence parameters possible are specifically contemplated unless specifically indicated to the contrary.

These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Disclosed are isolated nucleic acids comprising or encoding (i) a bacteriophage origin of replication, (ii) a bacteriophage packaging signal, and (iii) a heterologous target single-strand DNA (ssDNA) sequence of interest, where the isolated nucleic acid does not comprise or encode a plasmid origin of replication. In some forms, the isolated nucleic acid further comprises or encodes a selectable marker. In some forms, the isolated nucleic acid is single stranded. In some forms, the isolated nucleic acid is double stranded. In some forms, the isolated nucleic acid is circular. In some forms, the isolated nucleic acid is linear. In some forms, the isolated nucleic acid is circular and double stranded. In some forms, the target ssDNA sequence of interest is a scaffold sequence. In some forms, the scaffold sequence can form a 2D or 3D DNA origami structure. In some forms, the target ssDNA sequence of interest encodes bitstream data.

In some forms, the isolated nucleic acid comprises a bacteriophage origin of replication, a bacteriophage packaging signal, and a heterologous target ssDNA sequence of interest. In some forms, the isolated nucleic acid comprises a bacteriophage origin of replication and a bacteriophage packaging signal and encodes a heterologous target ssDNA sequence of interest. In some forms, the isolated nucleic acid comprises a bacteriophage origin of replication and a heterologous target ssDNA sequence of interest and encodes a bacteriophage packaging signal. In some forms, the isolated nucleic acid comprises a bacteriophage packaging signal and a heterologous target ssDNA sequence of interest and encodes a bacteriophage origin of replication. In some forms, the isolated nucleic acid encodes a bacteriophage origin of replication, a bacteriophage packaging signal, and a heterologous target ssDNA sequence of interest. In some forms, the isolated nucleic acid encodes a bacteriophage origin of replication and a bacteriophage packaging signal and comprises a heterologous target ssDNA sequence of interest. In some forms, the isolated nucleic acid encodes a bacteriophage origin of replication and a heterologous target ssDNA sequence of interest and comprises a bacteriophage packaging signal. In some forms, the isolated nucleic acid encodes a bacteriophage packaging signal and a heterologous target ssDNA sequence of interest and comprises a bacteriophage origin of replication.

Generally, the term "comprising or encoding" is used to denote both nucleic acids that may embody nucleic acid product (e.g., comprise the nucleic acid product) or serve as the, or a, template for producing a nucleic acid or protein product (e.g., encode the nucleic acid product). Thus, for example, some forms of the disclosed nucleic acids can encode (or both encode and embody) a target ssDNA. Such a nucleic acid embodying (e.g., comprising) a target ssDNA would generally be single stranded nucleic acid. Such a nucleic acid encoding a target ssDNA generally could be a single stranded nucleic acid or a double stranded nucleic acid (generally depending on the form needed or preferred for replication form the bacteriophage origin of replication).

A. Nucleic Acid Scaffold Sequences

Nucleic acids for use in the described methods can be synthesized or natural nucleic acids.

In some embodiments, the nucleic acid sequences including the format of information are not naturally occurring nucleic acid sequences. In some embodiments, the nucleic acid sequences including the format of information are artificial or otherwise user defined nucleic acid sequences. Nucleic acid sequences that are artificial or otherwise user defined are typically non-naturally occurring nucleic acid sequences and can also be referred to as synthetic nucleic acid sequences.

In some embodiments, the nucleic acid nanostructures are not the genomic nucleic acid of a virus. In some embodiments, the nucleic acid nanostructures are virus-like particles.

In some embodiments, bit-stream data is encoded within a nucleic acid scaffold sequence, for example a synthesized nucleic acid sequence. The bit stream data can be retrievably encoded on a single-stranded long DNA scaffold. Typically, bit-stream data is "broken-up" into any size, for example, up to 1,000,000 nucleotides, or more than 1,000,000 nucleotides, for example, fragments can range from 500-50,000 bases, or more, per scaffold (in the digital storage field this is conceptually synonymous with "page" or "block"). The bit stream-encoded nucleic acid sequence is synthesized by any known strategy, and is amplified or purified using a variety of known techniques (i.e., asymmetric PCR, bead-based purification and separation). Although only a single nucleic acid strand is typically used as a scaffold sequence for folding the objects, the reverse complement of the nucleic acid strand is used as an alternative for all applications. Scaffolds are discussed in more detail below.

As introduced above, the system allows for facile production of any desired ssDNA sequence. Thus, in some embodiments, the desired target DNA sequence is not bit-stream data or a scaffold for a nanostructure. The some embodiments, the sequence is for building DNA, RNA, or protein libraries, single-cell barcoding, RNA sequence complementarity, gene circuit switches, and as a bait for nucleic acid binding proteins and binding to complementary DNA or RNA designed sequences.

In some embodiments, the ssDNA sequences is designed to facilitate homology directed repair (e.g., an homology directed repair template), for rolling circle amplification to generate multiple copies of the encoded sequence in a very long linear ssDNA strand, and for immune stimulation to sequences of interest.

Numerous other sources of nucleic acid samples are known or can be developed and any can be used with the described method. In some embodiments, nucleic acids used in the described methods are naturally occurring nucleic acids. Examples of suitable nucleic acid samples for use with in the described methods include genomic samples, RNA samples, cDNA samples, nucleic acid libraries (including cDNA and genomic libraries), whole cell samples, environmental samples, culture samples, tissue samples, bodily fluids, and biopsy samples.

Nucleic acid fragments are segments of larger nucleic molecules. Nucleic acid fragments, as used in the described method, generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample.

In certain embodiments, the nucleic acid sample is a fragment or part of genomic DNA, such as human genomic DNA. Human genomic DNA is available from multiple commercial sources (e.g., Coriell #NA23248). Therefore, nucleic acid samples can be genomic DNA, such as human genomic DNA, or any digested or cleaved sample thereof. Generally, an amount of nucleic acids between 375 bp and 1,000,000 bp is used per nucleic acid nanostructure.

1. Phagemids

In certain embodiments, the nucleic acid sequences are in the form of a phagemid. A phagemid is a plasmid that contains a replication origin usually from a single stranded phage such as f1, fd or M13 which allows the plasmid to enter a single strand replication mode in which only one of the Watson/Crick strands is packaged into the virus particle when helper phage e.g. M13K07 is added to the cell carrying the phagemid. Conventional phagemids thus combine features of plasmids (i.e., carry antibiotic resistance and enable replication of double stranded DNA) with features of phage vectors (i.e., allow for production and packing single stranded DNA into virions.

Figure 2:
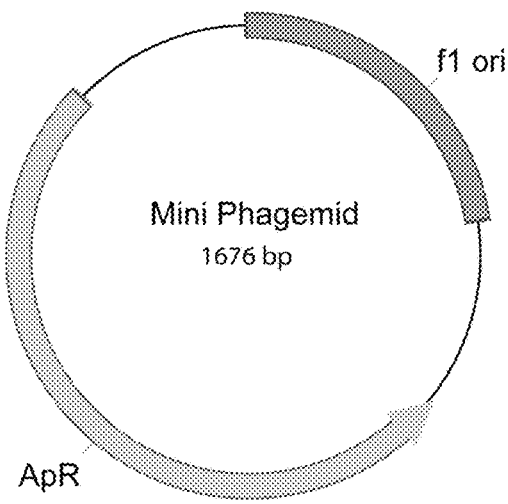
FIG. 2 is a schematic representation of the plasmid map of a miniature f1-origin containing phagemid with a single ampicillin beta-lactamase resistance gene. The f1-origin is labeled by a box and the ampicillin resistance gene (ApR) is labeled by an arrow.

The disclosed phagemids for production of long ssDNA typically contain origin of replication of bacteriophage. An exemplary origin of replication is the f1-origin of replication (FIG. 2).

The phagemids can, but need not, and preferably do not, contain a plasmid origin of replication for replication of the plasmid in the host organism (e.g., bacteria). Exemplary origins of replication of plasmids include ColE1, pMB1, pUC, pBR322, R6K, pl5A, and pSC101.

The disclosed phagemids can, but need not, contain one or more antibiotic resistance genes as selection markers. Exemplary antibiotic resistance genes include kanamycin, spectinomycin, streptomycin, ampicillin, carbenicillin, bleomycin, erythromycin, polymyxin b, tetracycline, and chloramphenicol. A preferred selection marker is an ampicillin resistance gene.

Thus, an exemplary phagemid of the present disclosure includes a single bacteriophage origin of replication, a user-defined naturally occurring or non-naturally occurring single-stranded scaffold nucleic acid sequence, and optionally a selection marker. The origin of replication is typically a single-stranded origin of replication.

For example, in some embodiments, the bacteriophage system utilized for the disclosed compositions and methods is ΦX174. ΦX174 also has a single-stranded origin of replication.

Phagemids including the single-stranded nucleic acid sequences according to the described methods are also provided.

All of the disclosed nucleic acids are provided as single stranded nucleic acids and double stranded nucleic acids; as circular nucleic acids and as linear nucleic acids; as sense and antisense sequences; and as coding and non-coding sequences. Thus, for each nucleic acid sequence provided, its reverse complement is also expressly disclosed.

B. Bacteriophage

In certain embodiments, the nucleic acid nucleic acid sequences in the form of a phagemid is packaged into a bacteriophage. Exemplary bacteriophage are filamentous bacteriophage, such as the Bacteriophage f1. Bacteriophage f1 is structurally classified as a class I filamentous phage, and is closely related to the other Ff phages, such as M13 and phage fd. The origin of replication of closely related phage can be interchanged for other origins in the same group, and thus the f1-origin can be used to signal for synthesis and packaging of the ssDNA into the M13 phage. Likewise, a helper strain plasmid could be generated with the f1 genome and an M13 origin of replication can be used for synthesis and production of ssDNA to be packaged into the f1 phage.

Bacteriophage that include single-stranded nucleic acid scaffold sequences, according to the described systems and methods are described. Typically, the bacteriophage include the capsid proteins of the M13 bacteriophage, and one or more single-stranded nucleic acid scaffold sequences that can be folded into a nucleic acid nanostructure. Preferably, the bacteriophage include a minimal amount of contaminating nucleic acids, such as bacterial dsDNA, or nucleic acids from the media. In some embodiments, the phage particles contain sufficiently pure single-stranded scaffold nucleic acid to enable immediate folding of the scaffold into a nucleic acid nanostructure without the need for subsequent purification of the nucleic acid.

Typically, the total amount of nucleic acid within the bacteriophage includes less than 30%, less than 20%, for example, 10%, 9%, 8%, 7%, 6%, 5%, 4%, 3%, 2%, or 1%, or less than 1% by weight of double-stranded DNA. Typically, the total amount of nucleic acid within the bacteriophage includes more than 70%, more than 80%, for example, at least 90%, 99%, 98%, 97%, 96%, 95%, 94%, 93%, 92%, or 91%, or 100% by weight of single-stranded nucleic acid.

In some embodiments, the bacteriophage includes the coat proteins of the M13 bacteriophage, or a mutant or variant of the M13 bacteriophage. An exemplary mutant or variant of the M13 bacteriophage is mutated to disrupt the capsid package, for example, such that the phage directly exports the single-stranded nucleic acid scaffold into the bacterial cell, or excretes the single-stranded nucleic acid scaffold into the growth media.

Clarified growth media, including the bacteriophage and the single-stranded nucleic acid scaffold sequences produced according to the described methods, is also described.

C. Microorganisms

In certain embodiments, the nucleic acid nucleic acid sequences in the form of a phagemid is packaged into a bacteriophage within a microorganism containing a 'helper' phage, which provides the necessary viral components to enable single stranded DNA replication and packaging of the phagemid DNA into phage particles. The 'helper' phage infects the bacterial host by first attaching to the host cell's pilus and then, after attachment, transporting the phage genome into the cytoplasm of the host cell. Inside the cell, the phage genome triggers production of single stranded phagemid DNA in the cytoplasm. This phagemid DNA is then packaged into phage particles. Exemplary "helper"

phages are VCSM13, M13K07, R408, M13cp, hyperphage, R408d3, and KM13 (an exemplary helper phage plasmid map is depicted in FIG. 1).

Exemplary bacterial hosts include *Escherichia coli* strains such as ER2738, TG1, SS320 (or MC1061 F' cells). An exemplary bacterial strain is an *Escherichia coli* bacterial "helper strain," such as the strain M13cp.

In a helper plasmid system, the M13 genes are moved to a double-stranded, low-copy number helper plasmid that is be paired with a second plasmid that contains a single-stranded origin of replication (e.g., an f1-origin, called a phagemid), that allows for synthesis and packaging of ssDNA with utility in phage display (Pasqualini, et al. Nature, 380, 364-366 (1996); Winter, et al., Annu Rev Immunol, 12, 433-455 (1994)). A helper/phagemid system has previously been used in scaffolded DNA origami for production of a phagemid that encodes a 2,404-nt sequence containing an f1-origin, a pUC origin, and an ampicillin selection marker ((Brown, et al., Nanoscale, 7, 16621-16624 (2015)). Nickels, et al., *Small*, 10, 1765-1769 (2014) describes direct use of intact bacteriophage particles as a scaffold source for DNA.

Historically, phagemids could accommodate custom inserts several kb in size, but include a 2-3 kb fixed region that limited their usefulness in producing custom origami scaffolds. Dotto et al. *Proc. Natl. Acad. Sci. U.S.A.*, 79, 7122-7126 (1982) used phagemids with modified origins to show that f1-ori ssDNA synthesis initiation and termination functions overlap, but can be inactivated separately by modifying distinct sequences. Specthrie et al. *Mol. Biol.*, 228, 720-724 (1992) packaged ssDNA as short as 292 bases into phage-like particles they called microphages. They were able to build small ssDNA strands using a phagemid that included an f1-ori, a packaging sequence (PS) and a truncated f1-ori that acts as a terminator (f1-oriA29). The terminator interrupts ssDNA synthesis of the full phagemid sequence, leading to packaging and export of only the region flanked by the ori and terminator. To increase scaffold sequence customizability, Nafisi, et al., *Synthetic Biology*, 3(1), ysy015 (8 pages) (2018) created a new phagemid, pScaf. After optimizing the pScaf ssDNA synthesis terminator, an iterative restriction-enzyme digestion and ligation scheme to clone several sequence inserts to produce scaffolds ranging from 1512 to 10080 bases in total length, each including an identical 393-base fixed region. Several DNA origami shapes were designed and folded using the custom scaffolds, including a one-pot assembly of three scaffolds into a six-helix-bundle trimer.

Praetorius, et al., *Nature*, 552:84-87 2017 describes using bacteriophages to generate single-stranded precursor DNA that contains target strand sequences interleaved with self-excising 'cassettes', with each cassette including two Zn2+-dependent DNA-cleaving DNA enzymes. All of the necessary single strands of DNA for several DNA origami were produced using shaker-flask cultures, and end-to-end production of macroscopic amounts of a DNA origami nanorod was demonstrated in a litre-scale stirred-tank bioreactor. The method is compatible with existing DNA origami design frameworks and retains the modularity and addressability of DNA origami objects that are important for implementing custom modifications using functional groups.

In some embodiments, strategies, methods and/or parts of the phagemids and/or bacteriophage described in Dotto, Specthrie, Nafisi, Praetorius, Nickels, or other references described herein or otherwise known in the art are adapted for use in the disclosed compositions and methods by, for example, recreating the phagemid providing a target ssDNA sequence without the plasmid origin of replication.

In preferred embodiments, the helper plasmid system is improved by entirely removing the f1-origin and packaging signal from a helper plasmid under a chloramphenicol selection marker (*E. coli* strain M13cp) (Chasteen, L., et al. Nucleic Acids Res, 34, e145 (2006)). This strain produces all 10 M13 phage proteins, but the plasmid does not get packaged into the phage particle because the helper plasmid sequence does not contain the packaging signal and is not single-stranded. Cloning into this strain thus allows for the production of pure ssDNA without the requirement of a dsDNA origin, and removes the dsDNA impurities from the produced phage.

Microorganisms that produce pure single stranded nucleic acid of a user-defined length and sequence are described. The microorganisms typically include an recombinant phagemid; and a double stranded nucleic acid helper plasmid. The phagemid includes an origin of replication; a single stranded nucleic acid scaffold of a user-defined length and sequence; and optionally a selection marker. The helper plasmid typically includes the genes of the corresponding phage. In some embodiments, the helper plasmid lacks the phage packaging gene and/or packaging signal. An exemplary origin of replication is the f1-origin of replication. In some embodiments, the microorganism includes the genome of the M13 bacteriophage, or a mutant or variant of the genome of the M13 bacteriophage. An exemplary mutant or variant genome of the M13 bacteriophage is mutated to disrupt the capsid package, for example, such that the microorganism directly exports the single-stranded nucleic acid scaffold into the cell, or excretes the single-stranded nucleic acid scaffold into the growth media. Clarified growth media, including the single-stranded nucleic acid scaffold sequences produced according to the described methods, is also described.

The host microorganism can also encode additional elements that form part of a nanostructure formed from the ssDNA. The constructs encoding the additional elements can be incorporated into the genome of the host cell or expressed by an extrachromosomal plasmid. In some embodiments, the additional functional elements are encoded on the same or a separate plasmid encoding the bacteriophage elements needed to package the phagemid into a bacteriophage particle. Additional functional elements or moieties that can be expressed by the host cell are discussed in more detail below and include, but are not limited to, single-guide- or crispr-RNAs (crRNA), anti-sense DNA, anti-sense RNA as well as DNA coding for therapeutic or non-therapeutic proteins, mRNA, miRNA, piRNA and siRNA, DNA-interacting proteins such as CRISPR, TAL effector proteins, or zinc-finger proteins, lipids, carbohydrates, etc.

The host cell can include a lipopolysaccharide pathway. In some embodiments, the lipopolysaccharide pathway is disrupted. An example of such a host cell is ClearColi by Lucigen.

In some embodiments, the host cell lacks a functional RNase H gene (rnh), which can to increase yield of RNA functional elements and moieties. For example, increased RNA staple yield and increase in vivo nanoparticle folding yield.

Thus, systems that encodes both the ssDNA (e.g., for scaffolded DNA origami) as well as functional elements and moieties such as therapeutic/CRISPR RNAs/proteins and methods for full production and packaging thereof is also provided.

The plasmid(s) and phagemid(s) are expressed in a host cells, typically a microorganism such as a bacteria. Nanoparticles fold with the additional element(s) (e.g., siRNAs/Cas9/zinc fingers/aptamers) and can be purified according to the methods described herein.

Vector backbones, and cassettes thereof including promoters, terminators, plasmid (e.g., bacterial) origins of replication that can be utilized to facilitate expression of functional elements and moieties in host cells including bacteria are well known in the art. For example, "expression vectors" typically include one or more expression control sequences that controls and regulates the transcription and/or translation of DNA sequence of interest.

Nucleic acids in vectors can be operably linked to one or more expression control sequences. Operably linked means the disclosed sequences are incorporated into a genetic construct so that expression control sequences effectively control expression of a sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II).

A promotor is a DNA regulatory region capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoters are well known to those of skill in the art.

To bring a coding sequence under the control of a promoter the translation initiation site of the translational reading frame of the polypeptide or other expression construct interest is placed between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into RNA, which for protein-coding sequences can then be translated into the protein encoded by the coding sequence.

Likewise, although functional nucleic acid sequences (e.g., siRNA, RNAi, etc.), stables, and CRISPR RNAs do not encode a protein, control sequences can be operably linked to the functional nucleic acid sequences, to control their expression in a host cell.

Examples of expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

In some embodiments, the system including a phagemid and an expression vector for a therapeutic agent produces a therapeutic nanoparticle.

For example, it is possible to combine the several or all units of a nanoparticle that can be used for therapeutic delivery into a helper plasmid construct and a phagemid scaffold construct. In this case, a helper plasmid may be maintained under a low copy origin of replication (BAC or p15 origin) RNA sequences transcribed such as sgRNA with staple sequence incorporated, staple sequences with aptamers, staple sequences with siRNAs, or each of these with overhang (nonfunctional) sequences that base pair with ssRNA or ssDNA sequences from staples, transcribed by an inducible or non-inducible promoter and separated by cleavable ribozymes. On the same plasmid all genes or a subset of genes such as just G2P, G5P, and G10P of M13 expressed from the helper plasmid and therapeutic protein-coding genes such as genes that code for CRISPR proteins or zinc finger nucleases. A second phagemid is maintained in the cell that is complementary to the staples produced by the helper plasmid that can then fold into a nanoparticle.

This type of nanoparticle can be used for the delivery of gene editing or gene therapeutic purposes. The system may be transferable to other bacteria that reside in the gut, and may thus be used to export the therapeutic to the patient by normal bacterial cell lysis or by export from the bacteria though the microbiome-human symbiosis.

Figure 10A:
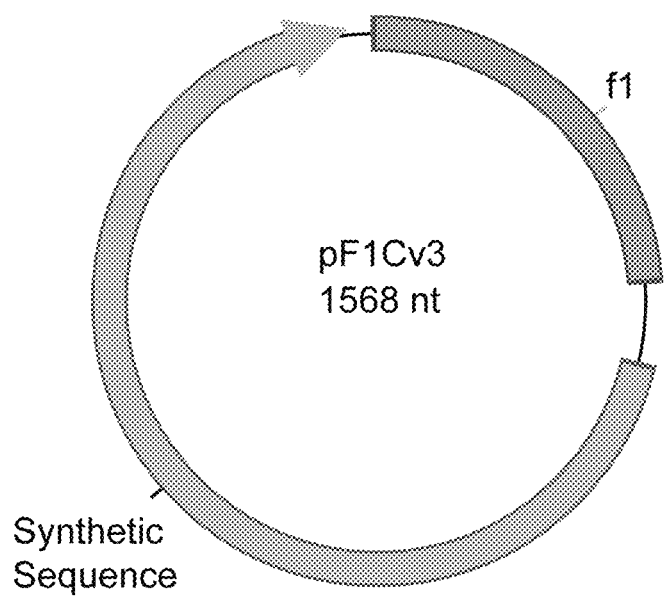
FIGS. 10A and 10B are schematic representations of plasmid maps of phagemids (pF1Cv3) (10A) and (pF1A-Cv3) (10B)) containing an f1-origin of replication ligated to a non-naturally occurring (artificial) sequence encoding the digital information equivalent of an encrypted line of text from The Crucible. The f1-origin is labeled as a box and the artificial sequence is labeled as an arrow. The artificial sequence shown here can be of any naturally occurring or non-naturally occurring sequence, including those encoding PX or DX structures, or genes that can be folded to nanoparticles or further allow selection. pF1A-Cv3 (10B) also includes an ampicillin resistance gene (AmpR) and its promotor labeled by an arrows.
Figure 10B:
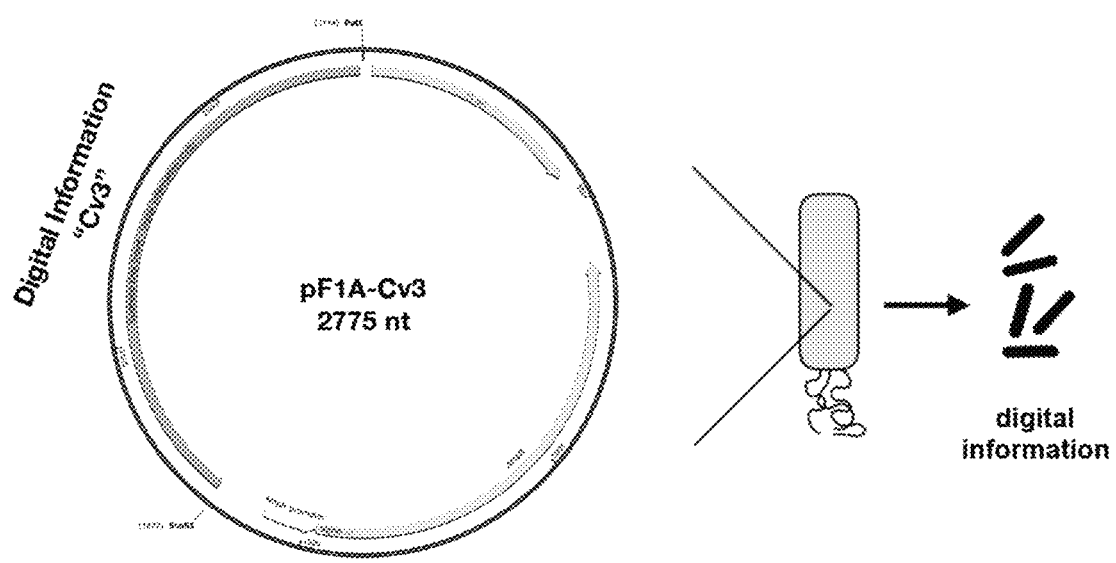
Figure 10C:
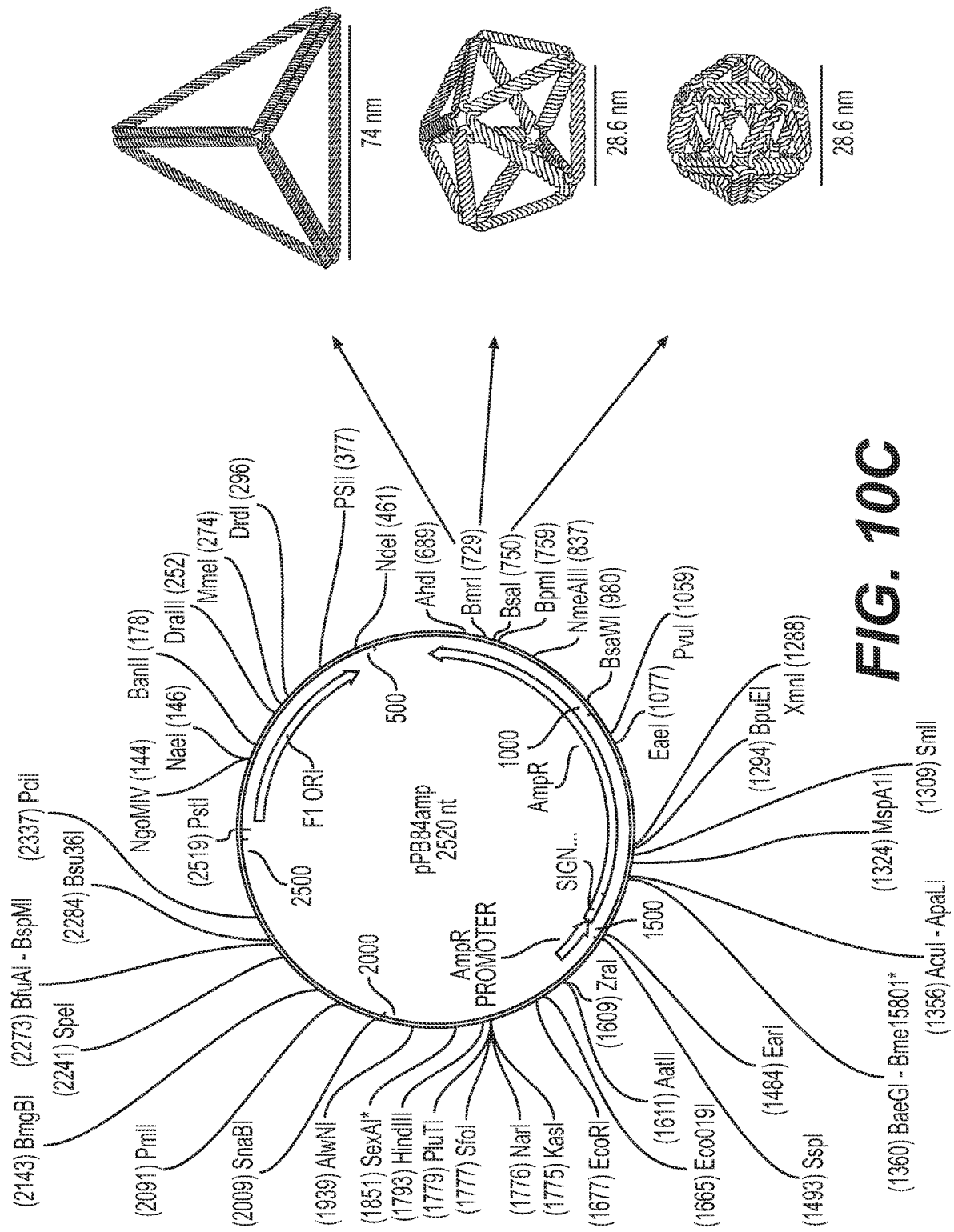
FIG. 10C is a schematic representation of a plasmid map of a phagemid (pPB84amp) having an f1-origin of replication ligated to a sequence encoding sequence capable of assembling into multiple DNA nanostructures where each nanostructure has the entire scaffold strand as base-paired with staples, and including an ampicillin resistance gene (AmpR) and its promotor labeled by an arrows. Such as a strategy is based on the notion of an exact sized scaffold for the origami. It is also the case that in some origami the scaffold would not be exact size and would instead have some region or regions not base paired and would thus form a ssDNA loop region for capture of eg. siRNAs, sgRNAs, CRISPR RNPs
Figure 10D:
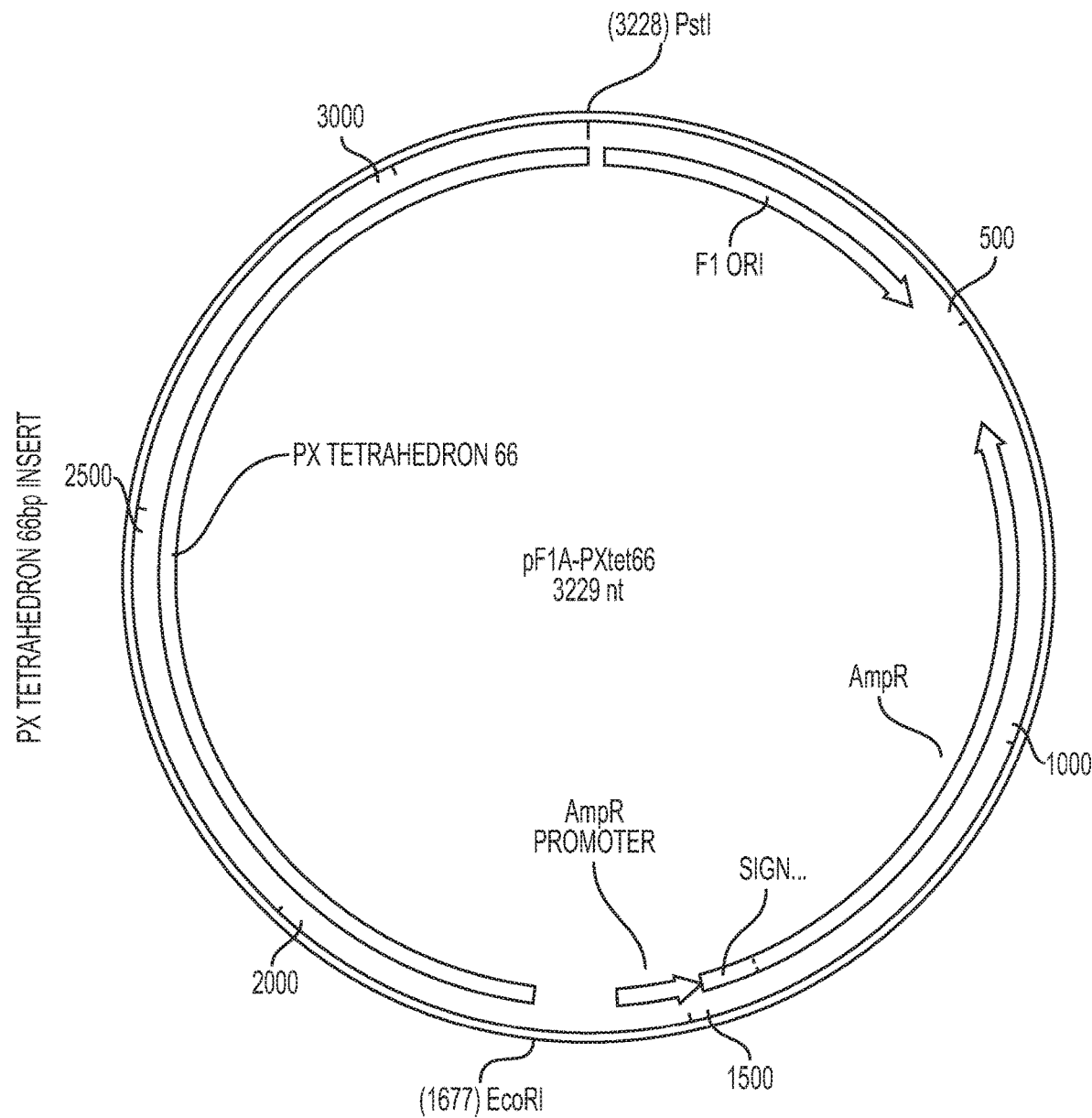
FIG. 10D is a schematic representation of a plasmid map of a phagemid (pF1A-PXtet66) having an f1-origin of replication ligated to a sequence encoding a sequence capable of assembling into a tetrahedron-66 PX structure without staples and including an ampicillin resistance gene (AmpR) and its promotor labeled by an arrows.
Figure 10E:
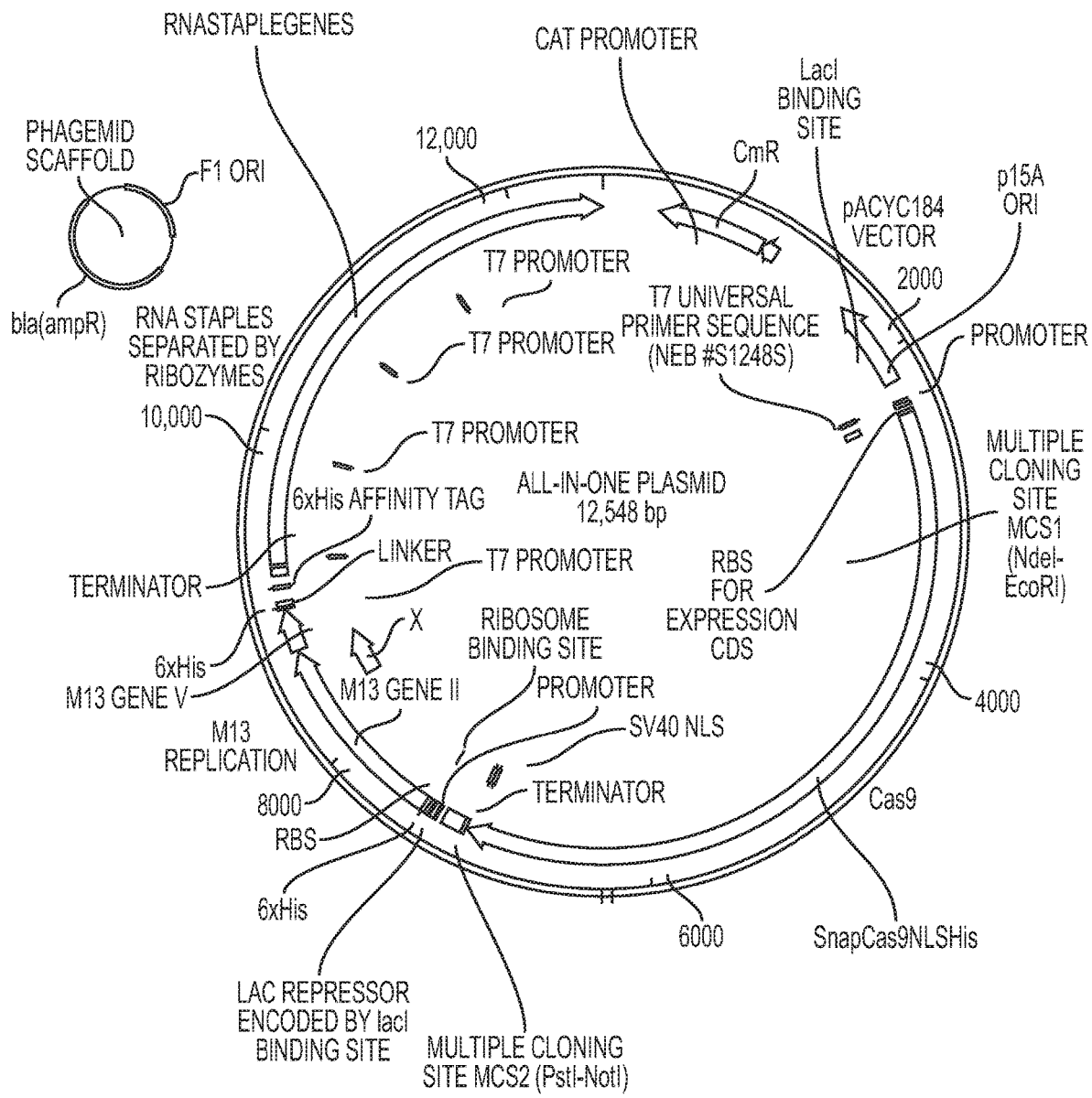
FIG. 10E is a schematic representation of plasmid maps of a phagemid (left) and "all-in-one" helper plasmid (right). The phagemid scaffold encodes a f1-origin of replication, a bla(ampR) gene, and particle scaffold that can into fold a tetrahedron, octahedron, or any arbitrary geometry. The "all-in-one" helper plasmid can encode one or more genes responsible for ssDNA synthesis (gene 2, gene 5, gene 10) with Tphi and VSV transcription terminators and T7 promoters; "genes" (e.g., cassettes) encoding, e.g., RNA staples, siRNA or crRNA with T7 promoters and a Tphi and VSV terminators with individual RNA staples separated by Twister-Pistol ribozyme pairs that cleave the RNA staples once synthesized; gene encoding Cas9 (or other protein), etc. The helper plasmid is typically a single copy or low-copy plasmid (e.g., pBeloBAC or pACYC184 vectors).
Figure 11A:
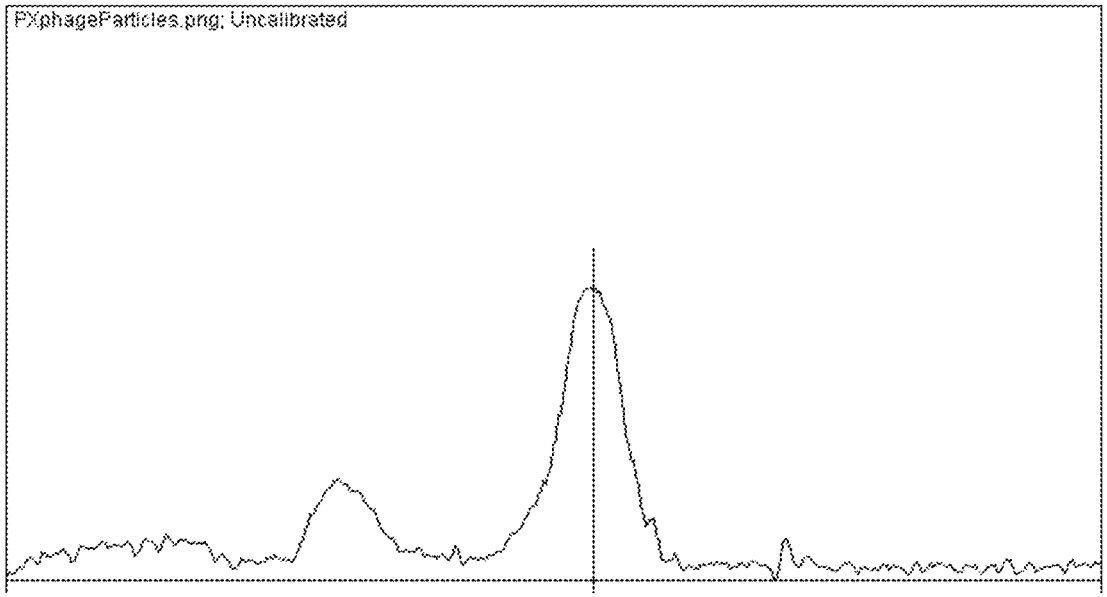
FIGS. 11A-11D are line graphs showing chromatograms corresponding to gel densiometry of ssDNA purified from phage (FIG. 11A); PX folded tetrahedron from ssDNA (FIG. 11B); PX folded tetrahedron and DX-folded pentagonal bipyramid from the same ssDNA (FIG. 11C); and F1-amp ssDNA showing folding of a PX, staple-less tetrahedron folding and nanoparticle for the sequence (FIG. 11D), respectively.
Figure 11B:
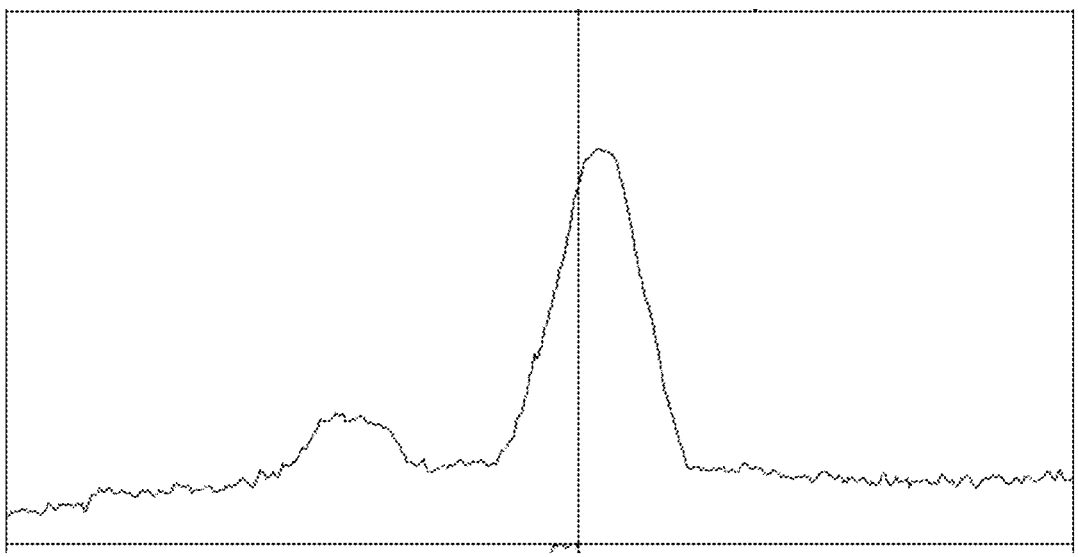
Figure 11C:
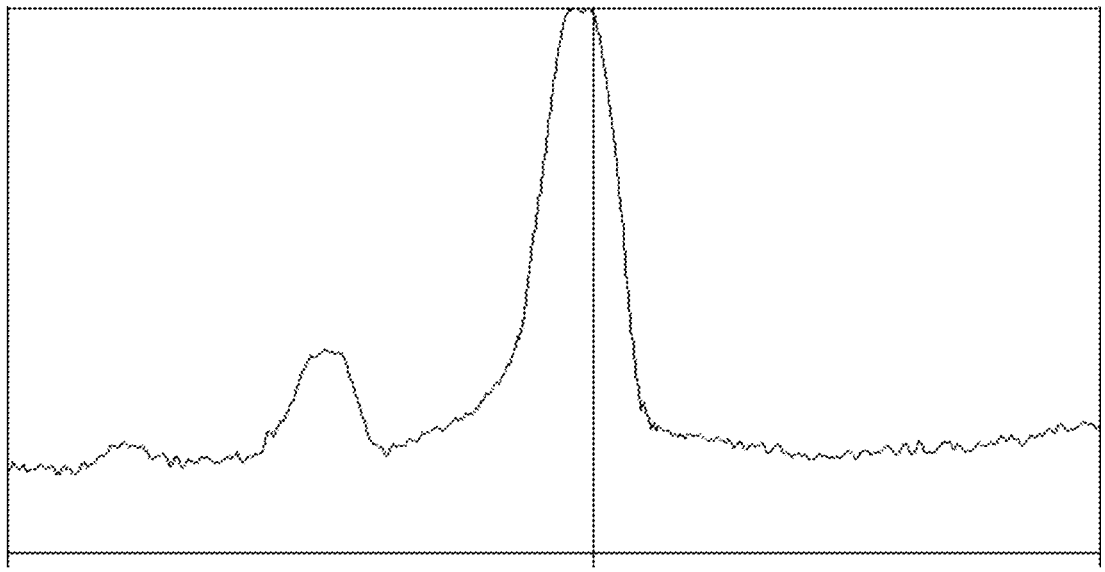
Figure 11D:
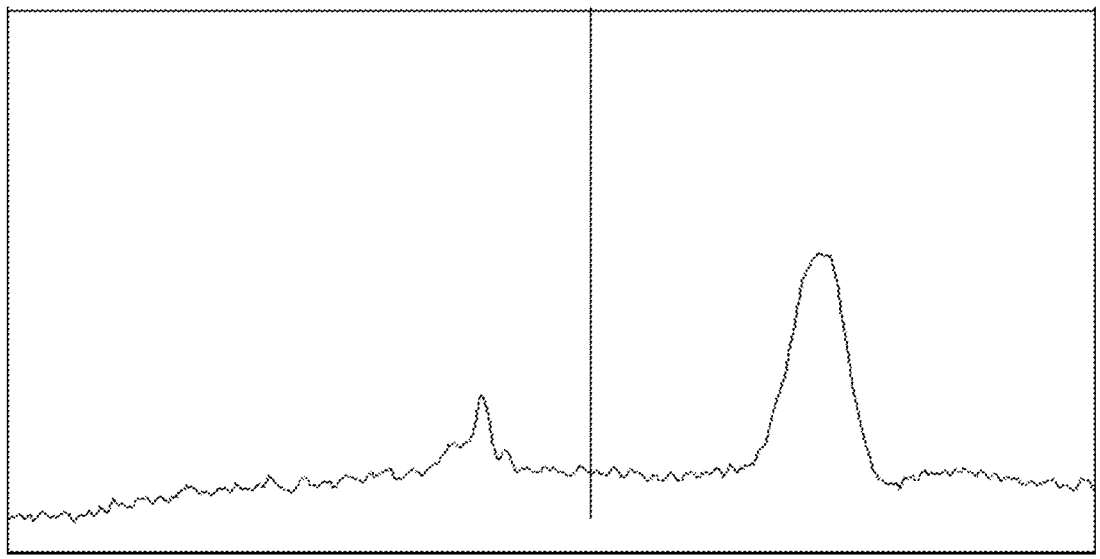
Figure 12A:
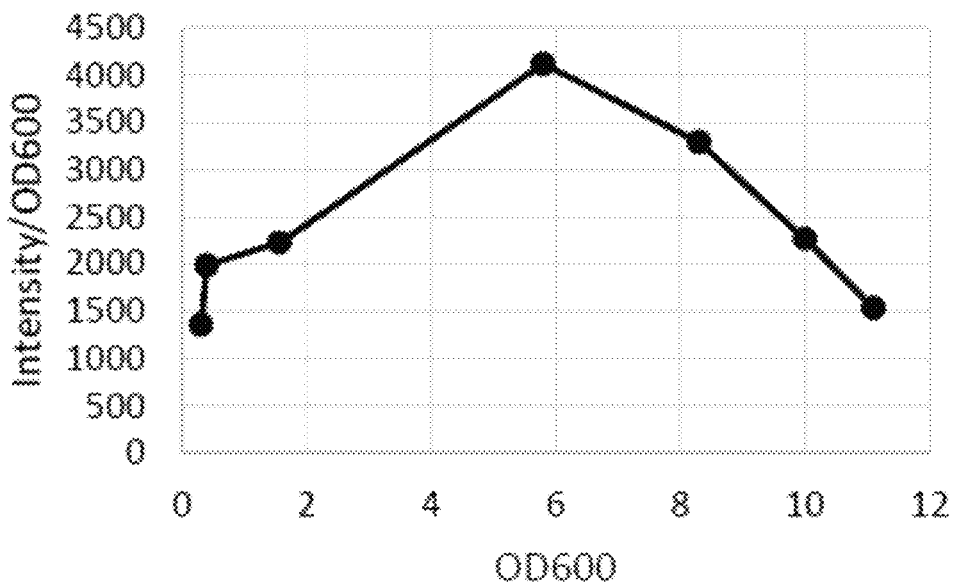
FIGS. 12A-12D are line graphs (Intensity/OD600 over 8 hours of time) showing 8 hours production in shaking flasks, followed by ssDNA purification (TB, filtered only (12A); TB filtered+RNase A/T1+Proteinase K (12B); 2×YT, filtered only (12C); and 2×YT, filtered+RNase A/T1+Proteinase K (12D).
Figure 12B:
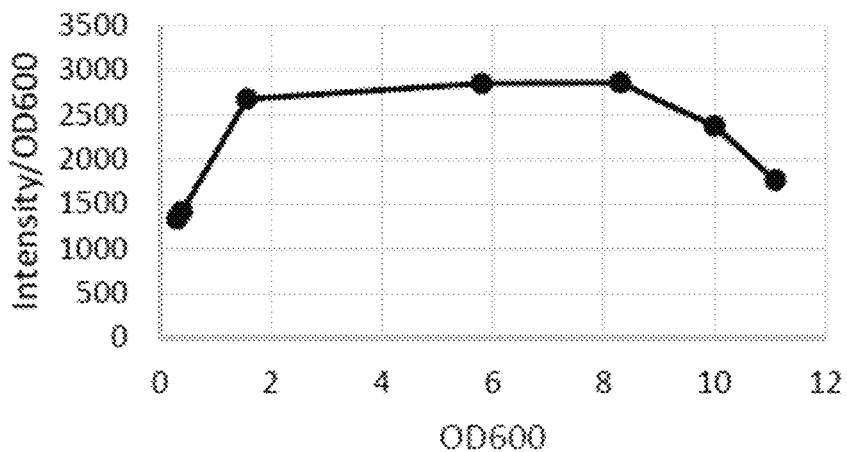
Figure 12C:
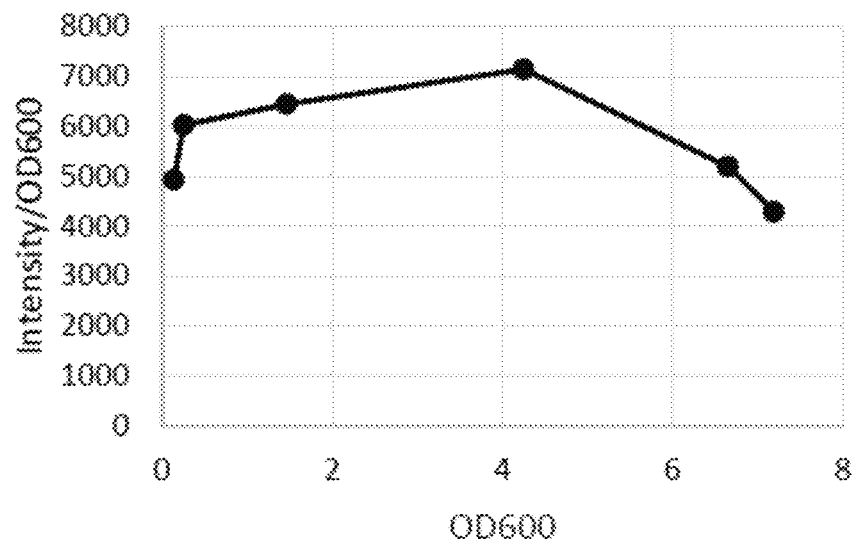
Figure 12D:
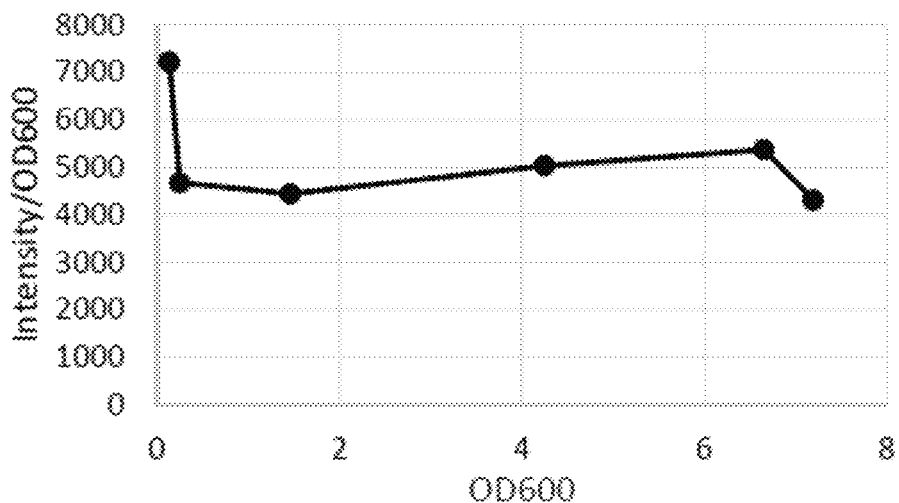
Figure 12E:
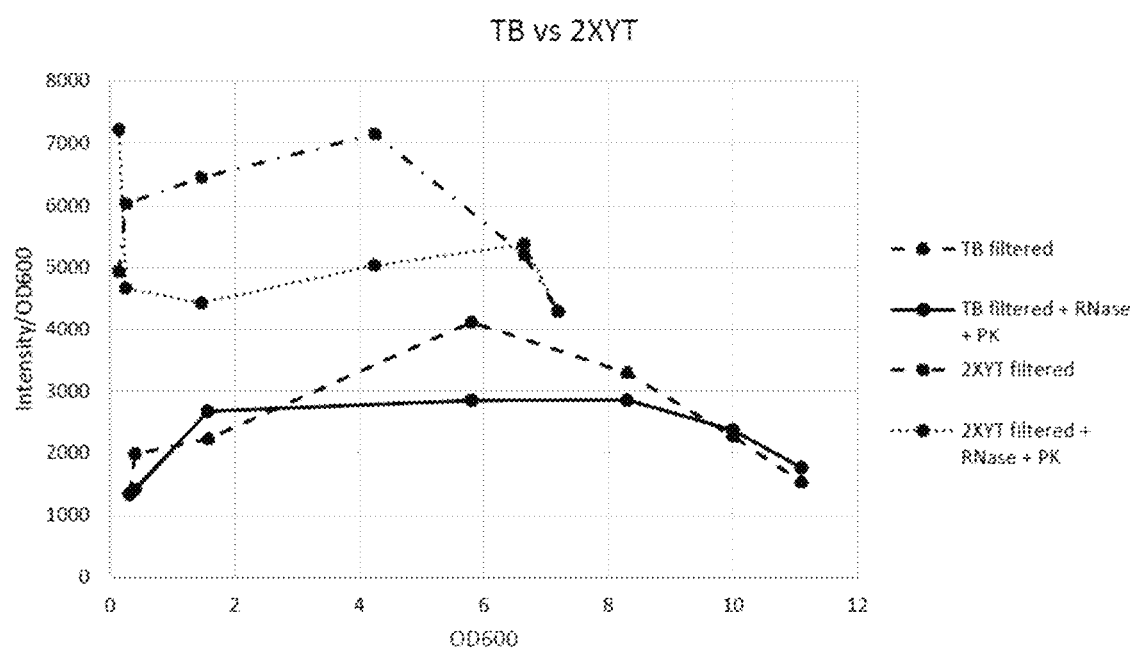
FIG. 12E is a single line graph showing all of the data points of FIGS. 12A-12D.

An exemplary plasmid design strategy is illustrated in FIG. 10E. A plasmid encodes genes responsible for ssDNA synthesis (e.g., gene 2, gene 5, gene 10) with Tphi and VSV transcription terminators and T7 promoters; construct(s) (e.g., "genes") encoding additional functional elements such as one or more of RNA staples, siRNA, crRNA, sequence encoding Cas9, etc. or a combination thereof operably linked to a promoter, e.g., T7 promoter and a terminator(s), e.g., Tphi and VSV terminators.

Additionally or alternatively, RNA staples or other functional elements can be separated by ribozymes (e.g. Twister-Pistol ribozyme pairs) that cleave the elements once synthesized. The plasmid backbone is typically a single copy or low-copy plasmid (pBeloBAC or pACYC184 vectors).

A phagemid encodes a nanoparticle scaffold to fold a tetrahedron, octahedron, or any arbitrary geometry as described in more detail elsewhere herein. The scaffold can be produced by the mechanism of M13 production of ssDNA. The additional elements are transcribed by activating the plasmid promoter. For example, T7 RNA polymerase can drive expression of RNA stables in blocks of 1, 2, 3, 4, 5, or more (e.g., 5 staples in one "cistron") which are ultimately separated by Twister-Pistol ribozymes between each staple. Staples may include sequences encoding siRNAs and crRNAs and aptamer. Proteins (zinc fingers, Cas9, etc.) can be expressed simultaneously with staples.

D. Nucleic Acid Nanostructures

The basic technique for creating nucleic acid (e.g., DNA) origami of various shapes ("nucleic acid nanostructure") involves folding a long single stranded polynucleotide, referred to as a "scaffold strand," into a desired shape or structure using a number of small "staple strands" as glue to hold the scaffold in place. Several variants of geometries can be used for construction of nucleic acid nanostructures. For example, in some embodiments, nucleic acid nanostructure from purely shorter single stranded staples can be assembled, or nucleic acid nanostructure including purely a single stranded scaffold folded onto itself, any of which can take on diverse geometries/architectures including wireframe or bricklike objects.

Nucleic acid nanostructures are nucleic acid assemblies of any arbitrary geometric shapes. Nucleic acid nanostructures can be of two-dimensional shapes, for example plates, or any other 2-D shape of arbitrary sizes and shapes. In some embodiments, the Nucleic acid nanostructures are simple DX-tiles, with two DNA duplexes connected by staples. DNA double crossover (DX) motifs are examples of small tiles (~4 nm×~16 nm) that have been programmed to produce 2D crystals (Winfree E et al., *Nature*. 394:539-544 (1998)); often these tiles contain pattern-forming features when more than a single tile constitutes the crystallographic repeat. In some embodiments, nucleic acid nanostructures are 2-D crystalline arrays by parallel double helical domains with sticky ends on each connection site (Winfree E et al., *Nature*. 6; 394(6693):539-44 (1998)). In other embodiments, nucleic acid nanostructures are 2-D crystalline arrays by parallel double helical domains, held together by crossovers (Rothemund P W K et al., *PLoS Biol*. 2:2041-2053 (2004)). In some embodiments, nucleic acid nanostructures are 2-D crystalline arrays by an origami tile whose helix axes propagate in orthogonal directions (Yan H et al., *Science*. 301:1882-1884 (2003)).

In some embodiments, nucleic acid nanostructures are three-dimensional wireframe nucleic acid (e.g., DNA) assemblies of a uniform polyhedron that has regular polygons as faces and is isogonal. In some embodiments, nucleic acid nanostructures are wireframe nucleic acid (e.g., DNA) assemblies of an irregular polyhedron that has unequal polygons as faces. In some embodiments, nucleic acid nanostructures are wireframe nucleic acid assemblies of a convex polyhedron. In some further embodiments, nucleic acid nanostructures are wireframe nucleic acid assemblies of a concave polyhedron. In some further embodiments, nucleic acid nanostructures are brick-like square or honeycomb lattices of nucleic acid duplexes in cubes, rods, ribbons or other rectilinear geometries. The corrugated ends of these structures are used to form complementary shapes that can self-assemble via non-specific base-stacking. Some exemplary superstructures of nucleic acid nanostructures include Platonic, Archimedean, Johnson, Catalan, and other polyhedral. In some embodiments, Platonic polyhedron are with multiple faces, for example, 4 face (tetrahedron), 6 faces (cube or hexahedron), 8 face (octahedron), 12 faces (dodecahedron), 20 faces (icosahedron). In some embodiments, nucleic acid nanostructures are toroidal polyhedra and other geometries with holes. In some embodiments, nucleic acid nanostructures are wireframe nucleic acid assemblies of any arbitrary geometric shapes. In some embodiments, nucleic acid nanostructures are wireframe nucleic acid assemblies of non-spherical topologies. Some exemplary topologies include nested cube, nested octahedron, torus, and double torus. In some embodiments, a set of tags to be associated with the data encoded on a nucleic acid nanostructures are selected and then encoded into a nucleic acid (DNA or locked nucleic acids or RNA, etc.) sequence using a conversion method of the user's choice. In some embodiments, it also includes a mechanism of direct conversion from, including but not limited to strings, integers, dates, events, genres, metadata, participants, or authors. In further embodiments, this additionally includes direct sequence selection, with the user keeping an external library of addresses. Nucleic acid nanostructures folded from the single-stranded scaffold sequences. Optionally including one or more staple strands, produced according to the described methods are provided.

1. Staple Strands

The number of staple strands will depend upon the size of the scaffold strand and the complexity of the shape or structure. For example, for relatively short scaffold strands (e.g., about 50 to 1,500 base in length) and/or simple structures the number of staple strands are small (e.g., about 5, 10, 50 or more). For longer scaffold strands (e.g., greater than 1,500 bases) and/or more complex structures, the number of staple strands are several hundred to thousands (e.g., 50, 100, 300, 600, 1,000 or more helper strands).

Typically, Staple strands include between 10 and 600 nucleotides, for example, 14-600 nucleotides.

In scaffolded DNA origami, a long single-stranded DNA is associated with complementary short single-stranded oligonucleotides that bring two distant sequence-space parts of the long strand together to fold into a defined shape. Historically, folding of DNA nanostructures has relied on tedious per-object design without generalized scaffold sequence choice.

A robust computational-experimental approach is used to generate DNA-based wireframe polyhedral structures of arbitrary scaffold sequence, symmetry and size. Staple strands are typically provided in a folding buffer. The staple strands are typically added to the single-stranded scaffold sequence in molar excess, in combination with appropriate salts and detergents.

2. Purification Tags

In addition to nucleic acid overhangs, other purification tags can be incorporated into the overhang nucleic acid sequence in any nucleic acid nanostructures for purification. In some forms, the overhang contains one or more purification tags. In some forms, the overhang contains purification tags for affinity purification. In some forms, the overhang contains one or more sites for conjugation to a nucleic acid, no non-nucleic acid molecule. For example, the overhang tag can be conjugated to a protein, or non-protein molecule, for example, to enable affinity-binding of the nucleic acid nanostructures. Exemplary proteins for conjugating to overhang tags include biotin and antibodies, or antigen-binding fragments of antibodies. Purification of antibody-tagged nucleic acid nanostructures can be achieved, for example, via interactions with antigens, and or protein A, G, A/G or L.

Further exemplary affinity tags are peptides, nucleic acids, lipids, saccharides, or polysaccharides. For example, overhang contains saccharides such as mannose molecules, then mannose-binding lectin can be used for selectively retrieve mannose-containing nucleic acid nanostructures, and vice versa. Other overhang tags allow further interaction with other affinity tags, for example, any specific interaction with magnetic particles allows purification by magnetic interactions.

3. Nucleic Acid Overhang Tag

In some embodiments, the overhang sequences are between 4 and 60 nucleotides, depending on user preference and downstream purification techniques. In preferred embodiments, the overhang sequences are between 4 and 25 nucleotides. In some embodiments, the overhang sequences contain 4, 5, 6, 7, 8, 9, 10, 11, 12, 13, 14, 15, 16, 17, 18, 19, 20, 21, 22, 23, 24, 25, 30, 35, 40, 45, 50 nucleotides in length.

In some embodiments, these overhang tag sequences are placed on the 5' end of any of the staples used to generate a wireframe nucleic acid. In other embodiments, these overhang tag sequences are placed on the 3' end of any of the staples used to generate a wireframe nucleic acid.

In some embodiments, overhang tag sequences contain metadata for the scaffolded nucleic acid, or the encapsulated nucleic acid that carries the encoded message. For example, overhang tag sequences have address(es) for locating a particular block of data. In some further embodiments, each overhang tag contains a plurality of functional elements such as addresses, as well as region(s) for hybridizing to other overhang tag sequences, or to bridging strands. These tag sequences added to the staple sequences at user-defined locations, with the untagged staple strands are then synthesized individually or as a pool directly using any known methods.

4. Other Functional Elements

Nucleic acid nanostructures optionally including nucleic acid overhang sequences can capture one or more functional moieties, including but not limited to single-guide- or crispr-RNAs (crRNA), anti-sense DNA, anti-sense RNA as well as DNA coding for therapeutic or non-therapeutic proteins, mRNA, miRNA, piRNA and siRNA, DNA-interacting proteins such as CRISPR, TAL effector proteins, or zinc-finger proteins, lipids, carbohydrates, etc. Exemplary functional groups include targeting elements, immunomodulatory elements, chemical groups, biological macromolecules, and combinations thereof.

In some embodiments, functionalized nucleic acid nanostructures include one or more single-strand overhang or scaffold DNA sequences that are complementary to the loop region of an RNA, such as an mRNA. Nucleic acid nanoparticles functionalized with mRNAs encoding one or more proteins are described. In one exemplary case, a tetrahedron (but could be any other object that can be designed from the procedure) can be functionalized with 3 (or 1 or 2 or more than 3) single-strand overhang DNA sequences that are complementary to the loop region of an RNA, for example an mRNA, for example an mRNA expressing a protein.

a. Targeting Elements

Targeting elements can be added to the staple strands of the DNA nanostructures, to enhance targeting of the nanostructures to one or more cells, tissues or to mediate specific binding to a protein, lipid, polysaccharide, nucleic acid, etc. For example, for use as biosensors, additional nucleotide sequences are included as overhang sequences on the staple strands.

Exemplary targeting elements include proteins, peptides, nucleic acids, lipids, saccharides, or polysaccharides that bind to one or more targets associated with an organ, tissue, cell, or extracellular matrix, or specific type of tumor or infected cell. The degree of specificity with which the nucleic acid nanostructures are targeted can be modulated through the selection of a targeting molecule with the appropriate affinity and specificity. For example, antibodies, or antigen-binding fragments thereof are very specific.

Additional functional groups can be introduced on the staple strand for example by incorporating biotinylated nucleotide into the staple strand. Any streptavidin-coated targeting molecules are therefore introduced via biotin-streptavidin interaction. In other embodiments, non-naturally occurring nucleotides are included for desired functional groups for further modification. Exemplary functional groups include targeting elements, immunomodulatory elements, chemical groups, biological macromolecules, and combinations thereof.

Typically, the targeting moieties exploit the surface-markers specific to a group of cells to be targeted. Exemplary targeting elements include proteins, peptides, nucleic acids, lipids, saccharides, or polysaccharides that bind to one or more targets associated with cell, or extracellular matrix, or specific type of tumor or infected cell. The degree of specificity with which the delivery vehicles are targeted can be modulated through the selection of a targeting molecule with the appropriate affinity and specificity. For example, antibodies, or antigen-binding fragments thereof are very specific.

In some embodiments, nanostructures include one or more sequences of nucleic acids that act as capture tags, or "Bait" sequences to specifically bind one or more targeted molecules.

b. Functional Nucleic Acids

In some embodiments, the nucleic acid nanostructures includes one or more functional nucleic acids. Functional nucleic acids that inhibit the transcription, translation or function of a target gene are described.

Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the target polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore the compositions can include one or more functional nucleic acids designed to reduce expression or function of a target protein.

Methods of making and using vectors for in vivo expression of the described functional nucleic acids such as antisense oligonucleotides, siRNA, shRNA, miRNA, EGSs, ribozymes, and aptamers are known in the art.

c. Gene Editing Molecules

In certain embodiments, the nucleic acid nanostructures are functionalized to include gene editing moieties, or to include components capable of binding to gene editing moieties. Exemplary gene-editing moieties that can be included within or bound to nucleic acid nanoparticles are CRISPR RNAs, for the gene editing through the CRISPR/Cas system.

CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/

176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a stem loop to mimic the natural crRNA:tracrRNA duplex as described in Cong, Science, 15:339(6121):819-823 (2013) and Jinek, et al., Science, 337(6096):816-21 (2012)). A single fused crRNA-tracrRNA construct can also be referred to as a guide RNA or gRNA (or single-guide RNA (sgRNA)). Within an a guide RNA or sgRNA, the crRNA portion can be identified as the "gRNA or sgRNA target sequence" and the tracrRNA is often referred to as the "gRNA or sgRNA scaffold."

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as CTPS1) can insert a short DNA fragment containing the target sequence into a guide RNA expression plasmid. The sgRNA expression plasmid contains the target sequence (about 20 nucleotides), a form of the tracrRNA sequence (the gRNA or sgRNA scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

In an exemplary embodiment, crRNA can be extended 3' and CRISPR-Cpf1 loaded with this crRNA can be used to capture this protein/RNA complex, as assayed by gel mobility shift and dual staining with a DNA-specific stain and a protein-specific stain.

In another embodiment, CRISPR-Cpf1 can be complexed with crRNA targeting a sequence in the EGFP gene. The cross-beam can be made to be a duplex that contains this specific sequence, but could be homologous to the target sequence with 10, 12, 13, 14, 15, 16, 17, 18, 19, 20, 21, 22, 23 nucleotides.

d. Zinc Finger Nucleases

In some embodiments, the nucleic acid nanostructures include a nucleic acid construct or constructs encoding a zinc finger nuclease (ZFN). ZFNs are typically fusion proteins that include a DNA-binding domain derived from a zinc-finger protein linked to a cleavage domain.

The most common cleavage domain is the Type IIS enzyme FokI. FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA*, 90:2764-2768 (1993); Kim et al. *Proc. Natl. Acad. Sci. USA*. 91:883-887 (1994a); Kim et al. *J. Biol. Chem.* 269:31,978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe(sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

e. mRNA

In some embodiments, nucleic acid nanostructures are modified by covalent or non-covalent association with an RNA that encodes one or more polypeptides, such as a protein. Therefore, in some embodiments, nucleic acid nanostructures are modified to include one or more messenger RNA molecules (mRNA). The messenger RNA can encode any protein or polypeptide. For example, in some embodiments, nucleic acid nanostructures are modified to include one or more mRNAs, each encoding one or more proteins. In an exemplary embodiment, the mRNA encodes a fluorescent protein or fluorophore. Exemplary fluorescent proteins include mCherry, mPlum, mRaspberry, mStrawberry, tdTomato, GFP, EBFP, Azurite, T-Sapphire, Emerald, Topaz, Venus, mOrange, AsRed2, and J-Red. In some embodiments, nucleic acid nanostructures are modified to include one or more messenger RNA molecules an RNA that encodes one or more polypeptides, such as a protein that is an antigen.

f. Antigens

In some embodiments, nucleic acid nanostructures are modified by covalent or non-covalent association with an antigen. Exemplary antigens include B cell antigens and T cell antigens. B cell antigens can be peptides, proteins, polysaccharides, saccharides, lipids, nucleic acids, small molecules (alone or with a hapten) or combinations thereof. T cell antigens are proteins or peptides. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof. Suitable antigens are known in the art and are available from commercial government and scientific sources. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. Antigens may be provided as single antigens or may be provided in combination. Antigens may also be provided as complex mixtures of polypeptides or nucleic acids. In some embodiments the antigen is a viral antigen. A viral antigen can be isolated from any virus. In some embodiments the antigen is a bacterial antigen. Bacterial antigens can originate from any bacteria. In some embodiments the antigen is a parasite antigen. In some embodiments the antigen is an allergen or environmental antigen. Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. In some embodiments the antigen is a tumor antigen. Exemplary tumor antigens include a tumor-associated or tumor-specific antigen.

g. Therapeutic or Prophylactic Agents

In some embodiments, nucleic acid nanostructures are modified by covalent or non-covalent association with a therapeutic agent, or a prophylactic agent, or a diagnostic agent, particularly protein- or nucleic acid-based therapeutic, prophylactic, or diagnostic agents. For example, one or more therapeutic, prophylactic, or diagnostic agents can be associated with the exterior of the nucleic acid nanoparticle, or packaged within the interior space of the nucleic acid nanoparticle, according to the design of the particle and location of the capture tag or site of interaction with the therapeutic or prophylactic or diagnostic agent.

5. Modifications to Nucleotides

In some embodiments, the nucleotides of the scaffolded nucleic acid and/or additional functional element sequences are modified. In some embodiments, the nucleotides of the encapsulated nucleic acid sequences are modified. In some embodiments, the nucleotides of the DNA staple sequences are modified. In some embodiments, the nucleotides of the DNA tag sequences are modified for further diversification of addresses associated with nucleic acid nanostructures. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and (acp3)w, 2,6-diaminopurine. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexylacrylamide-dCTP (aha-dCTP) to allow covalent attachment of amine reactive moieties, such as N-hydroxy succinimide esters (NHS).

Locked nucleic acid (LNA) is a family of conformationally locked nucleotide analogues which, amongst other benefits, imposes truly unprecedented affinity and very high nuclease resistance to DNA and RNA oligonucleotides (Wahlestedt C, et al., *Proc. Natl Acad. Sci. USA*, 975633-5638 (2000); Braasch, D A, et al., *Chem. Biol.* 81-7 (2001); Kurreck J, et al., *Nucleic Acids Res.* 301911-1918 (2002)). In some embodiments, the scaffolded DNAs are synthetic RNA-like high affinity nucleotide analogue, locked nucleic acids. In some embodiments, the staple strands are synthetic locked nucleic acids.

Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen P E et al., *Science* 254, 1497-1500 (1991)). It is chemically stable and resistant to hydrolytic (enzymatic) cleavage. In some embodiments, the scaffolded DNAs are PNAs. In some embodiments, the staple strands are PNAs.

In some embodiments, a combination of PNAs, DNAs, and/or LNAs is used for the nucleic acids encoding the format of information. In other embodiments, a combination of PNAs, DNAs, and/or LNAs is used for the staple strands, overhang sequences, or any nucleic acid component of the disclosed compositions.

In some embodiments, PEG modifications to the 3'end, 5' end, or both the 3' and 5' ends of staples for stability against exonucleases, and also ligation of staples for the same. The bioconjugated PEG group provides stability to the polynucleotides, preferably with affecting its function and can even be designed to be cleavable (see, e.g., Govan, et al., Bioconjug Chem., 22(10): 2136-2142 (2011)).

IV. Exemplary Phagemid and Plasmid Sequences

The annotated sequences of exemplary phagemids, cloning constructs, plasmids, and cassettes thereof, are provided below as SEQ ID NOS:1-17 and 62-64.

Also provided are phagemids, cloning constructs, plasmids, and cassettes thereof, having at least 50%, 60%, 70%, 75%, 80%, 85%, 90%, 95%, 96%, 97%, 98%, or 99% sequence identity to any one of SEQ ID NOS:1-17 and 62-64.

The provided exemplary sequences are annotated by reference to the nucleotide bases that corresponded with the origins of replication, cassettes (e.g., genes, expression constructions, etc.), regulatory elements, and other features, including those labeled in the maps of FIGS. 2, 7, and 10A-10E. As discussed herein, the phagemids and plasmids are modular. The sequences can be modified as disclosed herein to insert, substitute, delete, or mutate any of the features illustrated or otherwise disclosed herein including, but not limited to, selection/selectable markers, origins of replication, user defined naturally occurring or non-naturally occurring sequences (e.g., DNA origami and other nucleic acid scaffolds or ssDNA sequences of interest), and promoters, terminators, and other regulator elements. For example, any of the phagemids and plasmids can be used as a phagemid or plasmid backbone, wherein one or more additional cassettes or other features is added and/or substituted using the molecular biological tools and techniques described herein and otherwise known in the art. Thus, phagemids and plasmids with added and/or substituted elements are expressly disclosed, particularly with reference to SEQ ID NOS:1-8.

An annotated sequence for pF1A (illustrated in FIG. 2) is

```
1676 bp ds-DNA; circular DNA construct

FEATURES     Location/Qualifiers source       1..1676
             /organism="DNA construct"
             /mol_type="other DNA"

rep origin   19..447
             /direction=RIGHT
             /label=f1 on
             /note="f1 bacteriophage
             origin of replication; arrow indicates
             direction of (+) strand synthesis"

CDS          complement(616..1476)
             /codon_start=1
             /gene="bla"
             /product="beta-lactamase"
             /label=AmpR
             /note="confers resistance to
             ampicillin, carbenicillin, and related
             antibiotics"
             /translation="MSIQHFRVALIPFFAAFCL
             PVFAHPETLVKVKDAEDQLGARVGYIELDLNSGKILES
             FRPEERFPMMSTFKVLLCGAVLSRIDAGQEQLGRRIHY
             SQNDLVEYSPVTEKHLTDGMTVRELCSAAITMSDNTAA
             NLLLITIGGPKELTAFLHNMGDHVIRLDRWEPELNEAI
             PNDERDTIMPVAMATTLRKLLTGELLTLASRQQLIDWM
             EADKVAGPLLRSALPAGWFIADKSGAGERGSRGIIAAL
```

```
1676 bp ds-DNA; circular DNA construct

FEATURES     Location/Qualifiers

GPDGKPSRIVVIYTTGSQATMDERNRQIAEIGASLIKH
             W"(SEQ ID NO: 9)

promoter     complement(1477..1581)
             /gene="bla"
             /label=AmpR promoter ORIGIN
gagcgcaacg caattaatgt gcgccctgta gcggcgcatt
aagcgcggcg ggtgtggtgg ttacgcgcag cgtgaccgct
acacttgcca gcgccctagc gcccgctcct ttcgctttct
tcccttcctt tctcgccacg ttcgccggct ttccccgtca
agctctaaat cggggggctcc ctttagggtt ccgatttagt
gctttacggc acctcgaccc caaaaaactt gattagggtg
atggttcacg tagtgggcca tcgccctgat agacggtttt
tcgccctttg acgttggagt ccacgttctt taatagtgga
ctcttgttcc aaactggaac aacactcaac cctatctcgg
tctattcttt tgatttataa gggattttgc cgatttcggc
ctattggtta aaaaatgagc tgatttaaca aaaatttaac
gcgaattaca accggggtac atatgattgg ggtctgacgc
tcagtggaac gaaaactcac gttaagggat tttggtcatg
agattatcaa aaaggatctt cacctagatc cttttaaatt
aaaaatgaag ttttaaatca atctaaagta tatatgagta
aacttggtct gacagttacc aatgcttaat cagtgaggca
cctatctcag cgatctgtct atttcgttca tccatagttg
cctgactccc cgtcgtgtag ataactacga tacgggaggg
cttaccatct ggccccagtg ctgcaatgat accgcgagac
ccacgctcac cggctccaga tttatcagca ataaaccagc
cagccggaag ggccgagcgc agaagtggtc ctgcaacttt
atccgcctcc atccagtcta ttaattgttg ccgggaagct
agagtaagta gttcgccagt taatagtttg cgcaacgttg
ttgccattgc tacaggcatc gtggtgtcac gctcgtcgtt
tggtatggct tcattcagct ccggttccca acgatcaagg
cgagttacat gatcccccat gttgtgcaaa aaagcggtta
gctccttcgg tcctccgatc gttgtcagaa gtaagttggc
cgcagtgtta tcactcatgg ttatggcagc actgcataat
tctcttactg tcatgccatc cgtaagatgc ttttctgtga
ctggtgagta ctcaaccaag tcattctgag aatagtgtat
gcggcgaccg agttgctctt gcccggcgtc aatacgggat
aataccgcgc cacatagcag aactttaaaa gtgctcatca
ttggaaaacg ttcttcgggg cgaaaactct caaggatctt
accgctgttg agatccagtt cgatgtaacc cactcgtgca
cccaactgat cttcagcatc ttttactttc accagcgttt
ctgggtgagc aaaaacagga aggcaaaatg ccgcaaaaaa
gggaataagg gcgacacgga aatgttgaat actcatactc
ttcctttttc aatattattg aagcatttat cagggttatt
gtctcatgag cggatacata tttgaatgta tttagaaaaa
taaacaaata gggggttccgc gcacatttcc ccgaaaagtg
ccacctgacg tctaagaaac cattattatc atgacattaa
cctataaaaa taggcgtatc acgaggccct ttcgtc
// (SEQ ID NO: 1)
```

An annotated sequence for blaAmpR Complementary Sequence (illustrated in FIG. 7) is

```
1152 bp ds-DNA; natural linear DNA sequence

FEATURES     Location/Qualifiers source       1..1152
             /organism="unspecified"
             /mol_type="genomic DNA"

misc_feature 1..21
             /label=Complementary
             Sequence 3

CDS          complement(169..1029)
             /codon_start=1
             /gene="bla"
             /product="beta-lactamase"
             /label=AmpR
             /note="confers resistance to
```

| 1152 bp ds-DNA; natural linear DNA sequence |
| --- |

| FEATURES | Location/Qualifiers |
| --- | --- |
| | ampicillin, carbenicillin, and related antibiotics"<br>/translation="MSIQHFRVALIPFFAAFCLPVFAH<br>PETLVKVKDAEDQLGARVGYIELDLNSGKILESFRPEERFPMM<br>STFKVLLCGAVLSRIDAGQEQLGRRIHYSQNDLVEYSPVTEKH<br>LTDGMTVRELCSAAITMSDNTAANLLLTTIGGPKELTAFLHNM<br>GDHVTRLDRWEPELNEAIPNDERDTTMPVAMATTLRKLLTGEL<br>LTLASRQQLIDWMEADKVAGPLLRSALPAGWFIADKSGAGERG<br>SRGIIAALGPDGKPSRIVVIYTTGSQATMDERNRQIAEIGASL<br>IKHW" (SEQ ID NO: 9) |
| promoter | complement(1030..1134)<br>/gene="bla"<br>/label=AmpR promoter |
| misc_feature | 1135..1152<br>/label=Complementary Sequence 5 |

ORIGIN
```
acaaccgggg tacatatgat tggggtctga cgctcagtgg
aacgaaaact cacgttaagg gattttggtc atgagattat
caaaaaggat cttcacctag atccttttaa attaaaaatg
aagttttaaa tcaatctaaa gtatatatga gtaaacttgg
tctgacagtt accaatgctt aatcagtgag gcacctatct
cagcgatctg tctatttcgt tcatccatag ttgcctgact
ccccgtcgtg tagataacta cgatacggga gggcttacca
tctggcccca gtgctgcaat gataccgcga gacccacgct
caccggctcc agatttatca gcaataaacc agccagccgg
aagggccgag cgcagaagtg gtcctgcaac tttatccgcc
tccatccagt ctattaattg ttgccgggaa gctagagtaa
gtagttcgcc agttaatagt ttgcgcaacg ttgttgccat
tgctacaggc atcgtggtgt cacgctcgtc gtttggtatg
gcttcattca gctccggttc ccaacgatca aggcgagtta
catgatcccc catgttgtgc aaaaaagcgg ttagctcctt
cggtcctccg atcgttgtca gaagtaagtt ggccgcagtg
ttatcactca tggttatggc agcactgcat aattctctta
ctgtcatgcc atccgtaaga tgcttttctg tgactggtga
gtactcaacc aagtcattct gagaatagtg tatgcggcga
ccgagttgct cttgcccggc gtcaatacgg gataataccg
cgccacatag cagaacttta aaagtgctca tcattggaaa
acgttcttcg gggcgaaaac tctcaaggat cttaccgctg
ttgagatcca gttcgatgta acccactcgt gcacccaact
gatcttcagc atcttttact ttcaccagcg tttctgggtg
agcaaaaaca ggaaggcaaa atgccgcaaa aaagggaata
agggcgacac ggaaatgttg aatactcata ctcttccttt
ttcaatatta ttgaagcatt tatcagggtt attgtctcat
gagcggatac atatttgaat gtatttagaa aaataaacaa
ataggggttc cgcggagcgc aacgcaatta at
// (SEQ ID NO: 2)
```

An annotated sequence for F1 ori GBlock (illustrated in FIG. 7) is

| 468 bp ds-DNA; natural linear DNA |
| --- |

| FEATURES | Location/Qualifiers |
| --- | --- |
| source | 1..468<br>/organism="unspecified"<br>/mol_type="genomic DNA" |
| misc_feature | 1..18<br>/label=Complementary Sequence 5 |
| rep_origin | 19..447<br>/direction=RIGHT<br>/label=f1 on<br>/note="f1 bacteriophage origin of replication; arrow indicates direction of (+) strand synthesis" |
| misc_feature | 448..468<br>/label=Complementary Sequence 3 |

ORIGIN
```
gagcgcaacg caattaatgt gcgccctgta gcggcgcatt
aagcgcggcg ggtgtggtgg ttacgcgcag cgtgaccgct
acacttgcca gcgccctagc gcccgctcct ttcgctttct
tcccttcctt tctcgccacg ttcgccggct ttccccgtca
agctctaaat cgggggctcc ctttagggtt ccgatttagt
gctttacggc acctcgaccc caaaaaactt gattagggtg
atggttcacg tagtgggcca tcgccctgat agacgggttt
tcgccctttg acgttggagt ccacgttctt taatagtgga
ctcttgttcc aaactggaac aacactcaac cctatctcgg
tctattcttt tgatttataa gggattttgc cgatttcggc
```

468 bp ds-DNA; natural linear DNA

| FEATURES | Location/Qualifiers |
|---|---|

```
ctattggtta aaaaatgagc tgatttaaca aaaatttaac
gcgaattaca accggggtac atatgatt
// (SEQ ID NO: 3)
```

An annotated sequence for pF1Cv3 (illustrated in FIG. 10A) is

1555 bp ds-DNA; circular DNA construct

| FEATURES | Location/Qualifiers |
|---|---|
| source | 1..1555<br>/organism=" DNA construct"<br>/mol_type="other DNA" |
| misc_feature | 1..18<br>/label=Complementary<br>Sequence 5 |
| rep_origin | 19..447<br>/direction=RIGHT<br>/label=f1 on<br>/note="f1 bacteriophage origin of replication; Arrow indicates direction of (+) strand synthesis" |
| misc_feature | 448..468<br>/label=Complementary<br>Sequence 3 |
| misc_feature | 469..1555<br>/label=Cv3 |

```
ORIGIN
gagcgcaacg caattaatgt gcgccctgta gcggcgcatt
aagcgcggcg ggtgtggtgg ttacgcgcag cgtgaccgct
acacttgcca gcgccctagc gcccgctcct ttcgctttct
```

1555 bp ds-DNA; circular DNA construct

| FEATURES | Location/Qualifiers |
|---|---|

```
tcccttcctt tctcgccacg ttcgccggct ttccccgtca
agctctaaat cggggggctcc ctttagggtt ccgatttagt
gctttacggc acctcgaccc caaaaaactt gattagggtg
atggttcacg tagtgggcca tcgccctgat agacggtttt
tcgccctttg acgttggagt ccacgttctt taatagtgga
ctcttgttcc aaactggaac aacactcaac cctatctcgg
tctattcttt tgatttataa gggattttgc cgatttcggc
ctattggtta aaaaatgagc tgatttaaca aaatttaac
gcgaattaca accggggtac atatgattgt cgtcgtcccc
tcaaactctt gggtggagag gctattcgtt taaggtcaca
tcgcatgtaa tttacttatt ctctgttgtt gagccacccg
ggcgccagat tttgtttaaa gctttgtctc ttagtttgta
tagacagatt cagagtgcaa ggtttcgttc gctcgtacct
ggttttccct ggttcttcac agataggatt tgactttcta
caacacttat gcggcttcct acccgtttga aggccgatac
aggtgctgcg caaaatgcgg gcgaacatag agtatcaaaa
caacgccttc taatctagga atataggaa gatacgtatt
tgctaccatg ctttctgggg tcattaacga ccaacctctt
ttctttttaa gtaggattgc acaatgaatg aatacacgtg
gtccgataac tgaccaagta acatggttat cactcgatgt
ccgccagacg tgtgcaaacc aacccgggag ttacgtcact
aatccttcgc tacgtcgtga agatatttac ttgtgaatat
cgagggtaat aagataatag actgtgacta gtattgccag
actgtcgcta cctgcaacac ataactatcc tgaggttact
gcatagtact gattacaccc gagtcaaaat ttctaacttc
taacatgtac ctagtaacca gctcaataat tatgtcagaa
tatagctctg ggaaccctcg gacaattatg atacacggta
ttaatatctt gcttgcgtta gccacttctc atctttggat
accgattcta ttttgcatag cagttccttt tacacatata
agaatttcgc cataggtatg acctacccca gatcgtcgat
tatctgctgg aaaatttatt taacactatg tttctctcca
gatgtgagta tacacgataa ataatacctg ggtaccggtt
ggtgttatta ccttgtttct aagtgcttaa tcggcgctta
gtgataaggt tgtactagtc gacgcgtggc cgccaattat
tcttgtcata atttgacttt gttctatatg actatgatct
cctgtcatct cacctattga tgccacctttt tcagc
// (SEQ ID NO: 4)
```

An annotated sequence for pFA-1Cv3 (illustrated in FIG. 10B) is

2775 bp ds-DNA; circular DNA construct

| FEATURES | Location/Qualifiers |
|---|---|
| source | 1..2775<br>/organism="DNA construct"<br>/mol_type="other DNA" |
| rep_origin | 19..447<br>/direction=RIGHT<br>/label=f1 on<br>/note="f1 bacteriophage origin of replication; arrow indicates direction of (+) strand synthesis" |
| CDS | complement(616..1476)<br>/codon_start=1<br>/gene="bla"<br>/product="beta-lactamase"<br>/label=AmpR<br>/note="confers resistance to ampicillin, carbenicillin, and related antibiotics"<br>/translation="MSIQHFRVALIPFFAAFCLPVFAH PETLVKVKDAEDQLGARVGYIELDLNSGKILESFRPEERFPMM STFKVLLCGAVLSRIDAGQEQLGRRIHYSQNDLVEYSPVTEKH LTDGMTVRELCSAAITMSDNTAANLLLTTIGGPKELTAFLHNM GDHVTRLDRWEPELNEAIPNDERDTTMPVAMATTLRKLLTGEL LTLASRQQLIDWMEADKVAGPLLRSALPAGWFIADKSGAGERG SRGIIAALGPDGKPSRIVVIYTTGSQATMDERNRQIAEIGASL IKHW" (SEQ ID NO: 9) |

-continued

| 2775 bp ds-DNA; circular DNA construct |
| --- |

| FEATURES | Location/Qualifiers |
| --- | --- |
| promoter | complement(1477..1581)<br>/gene="bla"<br>/label=AmpR promoter |
| misc_feature | 1683..2769<br>/label=Cv3 |

```
ORIGIN
gagcgcaacg caattaatgt gcgccctgta gcggcgcatt
aagcgcggcg ggtgtggtgg ttacgcgcag cgtgaccgct
acacttgcca gcgccctagc gcccgctcct ttcgctttct
tcccttcctt tctcgccacg ttcgccggct ttccccgtca
agctctaaat cgggggctcc ctttagggtt ccgatttagt
gctttacggc acctcgaccc caaaaaactt gattagggtg
atggttcacg tagtgggcca tcgccctgat agacggtttt
tcgccctttg acgttggagt ccacgttctt aatagtggga
ctcttgttcc aaactggaac aacactcaac cctatctcgg
tctattcttt tgatttataa gggattttgc cgatttcggc
ctattggtta aaaaatgagc tgatttaaca aaaatttaac
gcgaattaca accggggtac atatgattgg ggtctgacgc
tcagtggaac gaaaactcac gttaagggat tttggtcatg
agattatcaa aaaggatctt cacctagatc cttttaaatt
aaaaatgaag ttttaaatca atctaaagta tatatgagta
aacttggtct gacagttacc aatgcttaat cagtgaggca
cctatctcag cgatctgtct atttcgttca tccatagttg
cctgactccc cgtcgtgtag ataactacga tacgggaggg
cttaccatct ggccccagtg ctgcaatgat accgcgagac
ccacgctcac cggctccaga tttatcagca ataaaccagc
cagccggaag ggccgagcgc agaagtggtc ctgcaacttt
atccgcctcc atccagtcta ttaattgttg ccgggaagct
agagtaagta gttcgccagt taatagtttg cgcaacgttg
ttgccattgc tacaggcatc gtggtgtcac gctcgtcgtt
tggtatggct tcattcagct ccggttccca acgatcaagg
cgagttacat gatccccccat gttgtgcaaa aaagcggtta
gctccttcgg tcctccgatc gttgtcagaa gtaagttggc
cgcagtgtta tcactcatgg ttatggcagc actgcataat
tctcttactg tcatgccatc cgtaagatgc ttttctgtga
ctggtgagta ctcaaccaag tcattctgag aatagtgtat
gcggcgaccg agttgctctt gcccggcgtc aatacgggat
aataccgcgc cacatagcag aactttaaaa gtgctcatca
ttggaaaacg ttcttcgggg cgaaaactct caaggatctt
accgctgttg agatccagtt cgatgtaacc cactcgtgca
cccaactgat cttcagcatc ttttactttc accagcgttt
ctgggtgagc aaaaacagga aggcaaaatg ccgcaaaaaa
gggaataagg cgacacgga aatgttgaat actcatactc
ttccttttc aatattattg aagcatttat cagggttatt
gtctcatgag cggatacata tttgaatgta tttagaaaaa
taaacaaata ggggttccgc gcacatttcc ccgaaaagtg
ccacctgacg tctaagaaac cattattatc atgacattaa
cctataaaaa taggcgtatc acgaggccct ttcgtcgaat
tcgtcgtcgt cccctcaaac tctttgggtgg agaggctatt
cgtttaaggt cacatcgcat gtaatttact tattctctgt
tgttgagcca cccgggcgcc agattttgtt taaagctttg
tctcttagtt tgtatagaca gattcagagt gcaaggtttc
gttcgctcgt acctggtttt ccctggttct tcacagatag
gatttgactt tctacaacac ttatgcggct tcctacccgt
ttgaaggccg atacaggtgc tgcgcaaaat gcgggcgaac
atagagtatc aaaacaacgc cttctaatct aggaatatag
ggaagatacg tatttgctac catgctttct ggggtcatta
acgaccaacc tcttttcttt taaagtagga ttgcacaatg
aatgaataca cgtggtccga taactgacca agtaacatgg
ttatcactcg atgtccgcca gacgtgtgca aaccaacccg
ggagttacgt cactaatcct tcgctacgtc gtgaagatat
ttacttgtga atatcgaggg taataagata atagactgtg
actagtattg ccagactgtc gctacctgca acacataact
atcctgaggt tactgcatag tactgattac acccgagtca
aaatttctaa cttctaacat gtacctagta accagctcaa
taattatgtc agaatatagc tctgggaacc ctcggacaat
tatgatacac ggtattaata tcttgcttgc gttagccact
tctcatcttt ggataccgat tctattttgc atagcagttc
cttttacaca tataagaatt tcgccatagg tatgacctac
cccagatcgt cgattatctg ctggaaaatt tatttaacac
tatgtttctc tccagatgtg agtatacacg ataaataata
cctgggtacc ggttggtgtt attaccttgt ttctaagtgc
ttaatcggcg cttagtgata aggttgtact agtcgacgcg
```

| 2775 bp ds-DNA; circular DNA construct |
| --- |
| FEATURES     Location/Qualifiers |

```
tggccgccaa ttattcttgt cataatttga ctttgttcta
tatgactatg atctcctgtc atctcaccta ttgatgccac
cttttcagcc tgcag
// (SEQ ID NO: 5)
```

An annotated sequence for pPB84amp (illustrated in FIG. 10C) is

| 2520 bp ds-DNA; circular DNA construct |
| --- |
| FEATURES     Location/Qualifiers |

```
source          1..2520
                /organism="DNA construct"
                /mol_type="other DNA"

rep_origin      19..447
                /direction=RIGHT
                /label=f1 on
                /note="f1 bacteriophage origin
                of replication; arrow indicates
                direction of (+) strand synthesis"

CDS             complement(616..1476)
                /codon start=1
                /gene="bla"
                /product="beta-lactamase"
                /label=AmpR
                /note="confers resistance to
                ampicillin,carbenicillin, and related
                antibiotics"
                /translation="MSIQHFRVALIPFFAAFCLPVFAH
                PETLVKVKDAEDQLGARVGYIELDLNSGKILESFRPEERFPMM
                STFKVLLCGAVLSRIDAGQEQLGRRIHYSQNDLVEYSPVTEKH
                LIDGMTVRELCSAAITMSDNTAANLLLITIGGPKELTAFLHNM
                GDHVIRLDRWEPELNEAIPNDERDTIMPVAMATTLRKLLTGEL
                LTLASRQQLIDWMEADKVAGPLMRSALPAGWFIADKSGAGERG
                SRGIIAALGPDGKPSRIVVIYTTGSQATMDERNRQIAEIGASL
                IKHW" (SEQ ID NO: 10)

promoter        complement(1477..1581)
                /gene="bla"
                /label=AmpR promoter misc_feature    1683..2514
                /label= insert ORIGIN
gagcgcaacg caattaatgt gcgccctgta gcggcgcatt
aagcgcggcg ggtgtggtgg ttacgcgcag cgtgaccgct
acacttgcca gcgccctagc gcccgctcct tcgctttct
tcccttcctt tctcgccacg ttcgccggct ttccccgtca
agctctaaat cgggggctcc ctttagggtt ccgatttagt
gctttacggc acctcgaccc caaaaaactt gattagggtg
atggttcacg tagtgggcca tcgccctgat agacggtttt
tcgccctttg acgttggagt ccacgttctt taatagtgga
ctcttgttcc aaactggaac aacactcaac cctatctcgg
tctattcttt tgatttataa gggattttgc cgatttcggc
ctattggtta aaaaatgagc tgatttaaca aaaatttaac
gcgaattaca accggggtac atatgattgg ggtctgacgc
tcagtggaac gaaaactcac gttaagggat tttggtcatg
agattatcaa aaggatctt cacctagatc cttttaaatt
aaaaatgaag ttttaaatca atctaaagta tatatgagta
aacttggtct gacagttacc aatgcttaat cagtgaggca
cctatctcag cgatctgtct atttcgttca tccatagttg
cctgactccc cgtcgtgtag ataactacga tacgggaggg
cttaccatct ggccccagtg ctgcaatgat accgcgagac
ccacgctcac cggctccaga tttatcagca ataaaccagc
cagccggaag ggccgagcgc ataagtggtc ctgcaacttt
atccgcctcc atccagtcta ttaattgttg ccgggaagct
agagtaagta gttcgccagt taatagtttg cgcaacgttg
ttgccattgc tacaggcatc gtggtgtcac gctcgtcgtt
```

-continued

| 2520 bp ds-DNA; circular DNA construct |
| --- |
| FEATURES   Location/Qualifiers |

```
tggtatggct tcattcagct ccggttccca acgatcaagg
cgagttacat gatcccccat gttgtgcaaa aaagcggtta
gctccttcgg tcctccgatc gttgtcagaa gtaagttggc
cgcagtgtta tcactcatgg ttatggcagc actgcataat
tctcttactg tcatgccatc cgtaagatgc ttttctgtga
ctggtgagta ctcaaccaag tcattctgag aatagtgtat
gcggcgaccg agttgctctt gcccggcgtc aatacgggat
aataccgcgc cacatagcag aactttaaaa gtgctcatca
ttggaaaacg ttcttcgggg cgaaaactct caaggatctt
accgctgttg agatccagtt cgatgtaacc cactcgtgca
cccaactgat cttcagcatc ttttactttc accagcgttt
ctgggtgagc aaaaacagga aggcaaaatg ccgcaaaaaa
gggaataagg gcgacacgga aatgttgaat actcatactc
ttcctttttc aatattattg aagcatttat cagggttatt
gtctcatgag cggatacata tttgaatgta tttagaaaaa
taaacaaata ggggttccgc gcacatttcc ccgaaaagtg
ccacctgacg tctaagaaac cattattatc atgacattaa
cctataaaaa taggcgtatc acgaggccct ttcgtcgaat
tcgtcgtcgt cccctcaaac tcttgggtgg agaggctatt
cgtttaaggt cacatcgcat gtaatttact tattctctgt
tgttgagcca cccgggcgcc agattttgtt taaagctttg
tctcttagtt tgtatagaca gattcagagt gcaaggtttc
gttcgctcgt acctggtttt ccctggttct tcacagatag
gatttgactt tctacaacac ttatgcggct tcctacccgt
ttgaaggccg atacaggtgc tgcgcaaaat gcgggcgaac
atagagtatc aaaacaacgc cttctaatct aggaatatag
ggaagatacg tatttgctac catgctttct tgggtcatta
acgaccaacc tcttttcttt taaagtagga ttgcacaatg
aatgaataca cgtggtccga taactgacca agtaacatgg
ttatcactag atgtccgcca gacgtgtgca aaccaacccg
ggagttacgt cactaatcct tcgctacgtc gtgaagatat
ttacttgtga atatcgaggg taataagata atagactgtg
actagtattg ccagactgtc gctacctgca acacataact
atcctgaggt tactgcatag tactgattac acccgagtca
aaatttctaa cttctaacat gtacctagta accagctcaa
taattatgtc agaatatagc tctgggaacc ctcggacaat
tatgatacac ggtattaata tcttgcttgc gttagccact
tctcatcttt ggataccgat tctattttgc atagcagttc
cttttacaca tataagaatt tcgccatagg tatgctgcag
// (SEQ ID NO: 6)
```

An annotated sequence for pF1A-PXtet (illustrated in FIG. 10D) is

| 3229 bp ds-DNA; circular DNA construct |
| --- |
| FEATURES   Location/Qualifiers |

| source | 1..3229<br>/organism="DNA construct"<br>/mol_type="other DNA" |
|---|---|
| rep_origin | 19..447<br>/direction=RIGHT<br>/label=f1 on<br>/note="f1 bacteriophage origin of replication; arrow indicates direction of (+) strand synthesis" |
| CDS | complement(616..1476)<br>/codon_start=1<br>/gene="bla"<br>/product="beta-lactamase"<br>/label=AmpR<br>/note="confers resistance to ampicillin, carbenicillin, and related antibiotics"<br>/translation="MSIQHFRVALIPFFAAFCLPVFAH PETLVKVKDAEDQLGARVGYIELDLNSGKILESFRPEERFPMM STFKVLLCGAVLSRIDAGQEQLGRRIHYSQNDLVEYSPVTEKH LTDGMTVRELCSAAITMSDNTAANLLLTTIGGPKELTAFLHNM GDHVTRLDRWEPELNEAIPNDERDTTMPVAMATTLRKLLTGEL |

| 3229 bp ds-DNA; circular DNA construct |
| --- |

| FEATURES | Location/Qualifiers |
| --- | --- |
| | LTLASRQQLIDWMEADKVAGPLMRSALPAGWFIADKSGAGERG<br>SRGIIAALGPDGKPSRIVVIYTTGSQATMDERNRQIAEIGASL<br>IKHW" (SEQ ID NO :10) |
| promoter | complement(1477..1581)<br>/gene="bla"<br>/label=AmpR promoter |
| misc_feature | 1683..3229<br>/label=PX tetrahedron 66 |

```
ORIGIN
gagcgcaacg caattaatgt gcgccctgta gcggcgcatt
aagcgcggcg ggtgtggtgg ttacgcgcag cgtgaccgct
acacttgcca gcgccctagc gcccgctcct ttcgctttct
tcccttcctt tctcgccacg ttcgccggct ttccccgtca
agctctaaat cggggctcc ctttagggtt ccgatttagt
gctttacggc acctcgaccc caaaaaactt gattagggtg
atggttcacg tagtgggcca tcgccctgat agacggtttt
tcgccctttg acgttggagt ccacgttctt aatagtgga
ctcttgttcc aaactggaac aacactcaac cctatctcgg
tctattcttt tgatttataa gggattttgc cgatttcggc
ctattggtta aaaatgagc tgatttaaca aaaatttaac
gcgaattaca accggggtac atatgattgg ggtctgacgc
tcagtggaac gaaaactcac gttaagggat tttggtcatg
agattatcaa aaaggatctt cacctagatc cttttaaatt
aaaaatgaag ttttaaatca atctaaagta tatatgagta
aacttggtct gacagttacc aatgcttaat cagtgaggca
cctatctcag cgatctgtct atttcgttca tccatagttg
cctgactccc cgtcgtgtag ataactacga tacgggaggg
cttaccatct ggccccagtg ctgcaatgat accgcgagac
ccacgctcac cggctccaga tttatcagca ataaaccagc
cagccggaag ggccgagcgc ataagtggtc ctgcaacttt
atccgcctcc atccagtcta ttaattgttg ccgggaagct
agagtaagta gttcgccagt taatagtttg cgcaacgttg
ttgccattgc tacaggcatc gtggtgtcac gctcgtcgtt
tggtatggct tcattcagct ccggttccca acgatcaagg
cgagttacat gatcccccat gttgtgcaaa aaagcggtta
gctccttcgg tcctccgatc gttgtcagaa gtaagttggc
cgcagtgtta tcactcatgg ttatggcagc actgcataat
tctcttactg tcatgccatc cgtaagatgc ttttctgtga
ctggtgagta ctcaaccaag tcattctgag aatagtgtat
gcggcgaccg agttgctctt gcccggcgtc aatacgggat
aataccgcgc cacatagcag aactttaaaa gtgctcatca
ttggaaaacg ttcttcgggg cgaaaactct caaggatctt
accgctgttg agatccagtt cgatgtaacc cactcgtgca
cccaactgat cttcagcatc ttttactttc accagcgttt
ctgggtgagc aaaaacagga aggcaaaatg ccgcaaaaaa
gggaataagg gcgacacgga aatgttgaat actcatactc
ttccttttc aatattattg aagcatttat cagggttatt
gtctcatgag cggatacata tttgaatgta tttagaaaaa
taaacaaata ggggttccgc gcacatttcc ccgaaaagtg
ccacctgacg tctaagaaac cattattatc atgacattaa
cctataaaaa taggcgtatc acgaggccct ttcgtcgaat
tcggtctcgc tggtgaaaag aaaggcgcgc cacagggcaa
tatcttacaa ttcaatcgag ccattaccac gagggggtcag
ttttctgacc cccacttgta atgtacacgt tgaagctact
gatatcttaa agtggctcgc tcgtcgaacg agcgtgctgc
gtcttgattt tgcgaataac ccgcaaataa accgtaaata
tagtgtaaga gcccttggcg tatgtgtggc tcgaggaagc
tcaacccgga tgcgaaactc aggaagaagg cttttgccca
gagcctgagt ccatcatccg tccttagctt cggcccgcca
cagctgcgcc aagggttcac aagtagcgta ttgtacggtg
tcatacctca ccttagggg tgcggtcctt cctgcttttg
catctacgac cgctgggata aaggtgtcgt atgacattat
acaatattgt ccttgtgaac tcttacacta taatattcgt
ttacggctcg gttagtgaca aaatccgggt gcagcatgtt
tttacaaact gcaccgcca tttgtcactc ctagagccgt
acgggaatat ttcccgtctt ttgacgggaa tttcgccgt
atttgcgtag gattcgcaaa tggaagacgc agttcgctcg
ttcgatcttt cggggggtatc tccgtacact ctcaccaggt
ccctagctga atgggtcatg gcgcatccga tcctgagagg
aaggttaaga ccccacccggg tgaggcacgt aaccgttgca
atcgctatga ttttttcagac aaattgcaat aattacgtgc
gacacccggt tcccacttaa cgtagatctc aggatgttta
```

3229 bp ds-DNA; circular DNA construct

FEATURES        Location/Qualifiers

```
aaattaccgc ccgtgataga cagagccaaa tttctgacac
gggcctcccc gtcagttttt acttcactgg aggcataggt
cagaagtgcc gctctggtct tcacgggcgt aaattttaaa
ccggatgcgc catgccgctt tcagcagaag tcctggtaaa
cttgtacctc ctcacccct cttttgagac gaggaggagt
atagagttta gcggcacttc taatacaagc ggttcggccc
ttttgggccg aaacccatgt atttaggag ccgctgagag
ctataggaga tctcgtcgaa agatcgacga gcgagcgcgt
ttaaggcccc agtagcattt gcgtgtaaag ctcaagtgaa
aggagaggat agctttccgg acggcaggct ccgtgggagg
gatttgtagt gctctattct gttcggtacc ttttttaggtt
acgaacagaa agacgcacta ggcacccctc ccctatagcc
tgagtgacgg aaagctacta ggcttttctta gcatgtttcg
aagcacggtt gccccgactc gaacggtcca tactaatttt
ttagcagcga ccgtgggcct cggggaagga gtgcttatgg
acatgctctc tgagcctagt atatcctctc cttttcgtgg
agcttgctcg acaaatttgt aagggctgc cctcgcgcgc
gccctaccct ctccggcatt aatctgcag
// (SEQ ID NO: 7)
```

An annotated sequence for All-in-one Plasmid (illustrated in FIG. 10E) is 12548 bp ds-DNA; circular DNA construct

| FEATURES | Location/Qualifiers |
|---|---|
| source | 1..12548<br>/organism="DNA construct"<br>/mol_type="other DNA" |
| source | 2276..7296<br>/organism="Cloning vector pSNAP-tag(T7)2"<br>/mol_type="other DNA" |
| source | 7297..9214<br>/organism="recombinant plasmid"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |

-continued

| 12548 bp ds-DNA; circular DNA construct | |
|---|---|
| FEATURES | Location/Qualifiers |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| source | join(7836..12548,1..7835)<br>/organism="Cloning vector M13mp18"<br>/mol_type="other DNA" |
| CDS | complement(348..1007)<br>/codon_start=1<br>/gene="cat"<br>/product=" chloramphenicol acetyltransferase"<br>/label=CmR<br>/note="confers resistance to chloramphenicol"<br>/translation="MEKKITGYTTVDISQWHRKEHFEA FQSVAQCTYNQTVQLDITAFLKTVKKNKHKFYPAFIHILARLM NAHPEFRMAMKDGELVIWDSVHPCYTVFHEQTETFSSLWSEYH DDFRQFLHIYSQDVACYGENLAYFPKGFIENMFFVSANPWVSF TSFDLNVANMDNFFAPVFTMGKYYTQGDKVLMPLAIQVHHAVC DGFHVGRMLNELQQYCDEWQGGA" (SEQ ID NO: 11) |
| promoter | complement(1008..1110)<br>/label=cat promoter<br>/note="promoter of the E. coli cat gene encoding chloramphenicol acetyltransferase" |
| rep origin | complement(1636..2181)<br>/direction=LEFT<br>/label=p15A on |

-continued

| 12548 bp ds-DNA; circular DNA construct | |
|---|---|
| FEATURES | Location/Qualifiers |
| | /note="Plasmids containing the medium-copy-number p15A origin of replication can be propagated in *E. coli* cells that contain a second plasmid with the ColE1 origin." |
| primer_bind | 2298..2317<br>/label=17 universal primer sequence (NEB #S1248S)<br>/note="17 universal primer sequence (NEB #S1248S)" |
| promoter | 2298..2315<br>/note="17 promoter (transcript start 5654 clockwise)" |
| protein_bind | 2317..2341<br>/label=LacI binding site<br>/bound moiety="LacI"<br>/note="lac operator" |
| RBS | 2371..2377<br>/label=RBS for expression CDS<br>/note="RBS for expression CDS" |
| misc_feature | 2383..2424<br>/label=multiple cloning site |
| MCS1 (NdeI-EcoRI) | /note="multiple cloning site MCS1 (NdeI-EcoRI)" |
| CDS | 2386..7134<br>/codon_start=1<br>/label=SnapCas9NLSHis<br>/translation="MASTMDIKLTGEFAMDKDCEMKRT TLDSPLGKLELSGCEQGLHEIKLLGKGTSAADAVEVPAPAAVL GGPEPLMQATAWLNAYFHQPEAIEEFPVPALHHPVFQQESFTR QVLWKLLKVVKFGEVISYQQLAALAGNPAATAAVKTALSGNPV PILIPCHRVVSSSGAVGGYEGGLAVKEWLLAHEGHRLGKPGLG PAVDKKYSIGLDIGTNSVGWAVITDEYKVPSKKFKVLGNTDRH SIKKNLIGALLFDSGETAEATRLKRTARRRYTRRKNRICYLQE IFSNEMAKVDDSFFHRLEESFLVEEDKKHERHPIFGNIVDEVA YHEKYPTIYHLRKKLVDSTDKADLRLIYLALAHMIKFRGHFLI EGDLNPDNSDVDKLFIQLVQTYNQLFEENPINASGVDAKAILS ARLSKSRRLENLIAQLPGEKKNGLFGNLIALSLGLTPNFKSNF DLAEDAKLQLSKDTYDDDLDNLLAQIGDQYADLFLAAKNLSDA ILLSDILRVNTEITKAPLSASMIKRYDEHHQDLTLLKALVRQQ LPEKYKEIFFDQSKNGYAGYIDGGASQEEFYKFIKPILEKMDG TEELLVKLNREDLLRKQRTFDNGSIPHQIHLGELHAILRRQED FYPFLKDNREKIEKILTFRIPYYVGPLARGNSRFAWMTRKSEE TITPWNFEEVVDKGASAQSFIERMTNFDKNLPNEKVLPKHSLL YEYFTVYNELTKVKYVTEGMRKPAFLSGEQKKAIVDLLFKTNR KVTVKQLKEDYFKKIECFDSVEISGVEDRFNASLGTYHDLLKI IKDKDFLDNEENEDILEDIVLTLTLFEDREMIEERLKTYAHLF DDKVMKQLKRRRYTGWGRLSRKLINGIRDKQSGKTILDFLKSD GFANRNFMQLIHDDSLTFKEDIQKAQVSGQGDSLHEHIANLAG SPAIKKGILQTVKVVDELVKVMGRHKPENIVIEMARENQTTQK GQKNSRERMKRIEEGIKELGSQILKEHPVENTQLQNEKLYLYY LQNGRDMYVDQELDINRLSDYDVDHIVPQSFLKDDSIDNKVLT RSDKNRGKSDNVPSEEVVKKMKNYWRQLLNAKLITQRKFDNLT KAERGGLSELDKAGFIKRQLVETRQITKHVAQILDSRMNTKYD ENDKLIREVKVITLKSKLVSDFRKDFQFYKVREINNYHHAHDA YLNAVVGTALIKKYPKLESEFVYGDYKVYDVRKMIAKSEQEIG KATAKYFFYSNIMNFFKTEITLANGEIRKRPLIETNGETGEIV WDKGRDFATVRKVLSMPQVNIVKKTEVQTGGFSKESILPKRNS DKLIARKKDWDPKKYGGFDSPTVAYSVLVVAKVEKGKSKKLKS VKELLGITIMERSSFEKNPIDFLEAKGYKEVKKDLIIKLPKYS LFELENGRKRMLASAGELQKGNELALPSKYVNFLYLASHYEKL KGSPEDNEQKQLFVEQHKHYLDEIIEQISEFSKRVILADANLD KVLSAYNKHRDKPIREQAENIIHLFTLTNLGAPAAFKYFDTTI DRKRYTSTKEVLDATLIHQSITGLYETRIDLSQLGGDPKKKRK VMDKHHHHHH" (SEQ ID NO: 12) |

-continued

| | 12548 bp ds-DNA; circular DNA construct |
|---|---|
| FEATURES | Location/Qualifiers |
| gene | 2428..7149<br>/gene="SNAP26b"<br>/label=SNAP26b |
| CDS | 7084..7104<br>/codon_start=1<br>/product="nuclear localization signal of SV40 (simian virus 40) large T antigen"<br>/label=SV40 NLS<br>/translation="PKKKRKV"<br>(SEQ ID NO: 13) |
| CDS | 7114..7131<br>/codon_start=1<br>/product="6xHis affinity tag"<br>/label=6xHis<br>/translation="HHHHHH"<br>(SEQ ID NO: 14) |
| misc_feature | 7141..7157<br>/label=multiple cloning site |
| MCS2 (PstI-NotI) | /note="multiple cloning site MCS2 (PstI-NotI)" |
| terminator | 7168..7290<br>/note="T7 Tphi transcription terminator" |
| promoter | 7328..7346<br>/note="T7 promoter"<br>/note="promoter for bacteriophage T7 RNA polymerase" |
| protein_bind | 7347..7371<br>/label=lac repressor encoded by lacI binding site<br>/bound moiety="lac repressor encoded by lacI"<br>/note="lac operator"<br>/note="The lac repressor binds to the lac operator to inhibit transcription in *E. coli*. This inhibition can be relieved by adding lactose or isopropyl-beta-D-thiogalactopyranoside (IPTG)." |
| RBS | 7386..7408<br>/note="efficient ribosome binding site from bacteriophage T7 gene 10 (Olins and Rangwala, 1989)" |
| RBS | 7402..7407<br>/note="ribosome binding site" |
| CDS | 7419..7436<br>/codon_start=1<br>/product="6xHis affinity tag"<br>/label=6xHis<br>/translation="HHHHHH"<br>(SEQ ID NO: 14) |
| CDS | 7437..8666<br>/codon_ start=1<br>/gene=" II"<br>/product="pII"<br>/label=M13 gene II<br>/note="replication"<br>/translation="IDMLVLRLPFIDSLVCSRLSGNDL<br>IAFVDLSKIATLSGINLSARTVEYHIDGDLTVSGLSHPFESLP<br>THYSGIAFKIYEGSKNFYPCVEIKASPAKVLQGHNVFGTTDLA<br>LCSEALLLNFANSLPCLYDLLDVNATTISRIDATFSARAPNEN<br>IAKQVIDHLRNVSNGQIKSTRSQNWESTVIWNETSRHRTLVAY" |

-continued

| | 12548 bp ds-DNA; circular DNA construct |
|---|---|
| FEATURES | Location/Qualifiers |
| | LKHVELQHYIQQLSSKPSAKMTSYQKEQLKVLSNPDLLEFASG<br>LVRFEARIKTRYLKSFGLPLNLFDAIRFASDYNSQGKDLIFDL<br>WSFSFSELFKAFEGDSMNIYDDSAVLDAIQSKHFTITPSGKTS<br>FAKASRYFGFYRRLVNEGYDSVALTMPRNSFWRYVSALVECGI<br>PKSQLMNLSTCNNVVPLVRFINVDFSSQRPDWYNEPVLKIA"<br>(SEQ ID NO: 15) |
| gene | 7464..8666<br>/gene=" II"<br>/label=II |
| gene | 8331..8666<br>/gene= "X"<br>/label=X |
| CDS | 8331..8666<br>/codon_start=1<br>/gene= "X"<br>/product="pX"<br>/label=X<br>/note=" replication"<br>/translation="MNIYDDSAVLDAIQSKHFTITPSG<br>KTSFAKASRYFGFYRRLVNEGYDSVALTMPRNSFWRYVSALVE<br>CGIPKSQLMNLSTCNNVVPLVRFINVDFSSQRPDWYNEPVLKI<br>A" (SEQ ID NO: 16) |
| CDS | 8678..8938<br>/codon_start=1<br>/gene="V"<br>/product="pV"<br>/label=M13 gene V<br>/note=" replication"<br>/translation="MIKVEIKPSQAQFTTRSGVSRQGK<br>PYSLNEQLCYVDLGNEYPVLVKITLDEGQPAYAPGLYTVHLSS<br>FKVGQFGSLMIDRLRLVPAK" (SEQ ID NO: 17) |
| gene | 8678..8921<br>/gene="V"<br>/label=V |
| CDS | 8939..8956<br>/codon_start=1<br>/product="6xHis affinity tag"<br>/label=6xHis<br>/translation="HHHHHH"<br>(SEQ ID NO: 14) |
| misc_feature | 8967..8978<br>/label=Linker<br>/note="Linker" |
| CDS | 9063..9080<br>/codon_start=1<br>/product="6xHis affinity tag"<br>/label=6xHis affinity tag<br>/note="6xHis"<br>/note="/dnas title=6xHis<br>affinity tag"<br>/translation="HHHHHH"<br>(SEQ ID NO: 14) |
| terminator | 9147..9194<br>/note=" T7 terminator"<br>/note="transcription<br>terminator for bacteriophage T7 RNA<br>polymerase" |
| misc_feature | 9215..12548<br>/label=RNAstapleGenes |
| promoter | 9215..9233<br>/label=T7 promoter<br>/note="promoter for<br>bacteriophage T7 RNA polymerase" |

-continued

| 12548 bp ds-DNA; circular DNA construct |
|---|

| FEATURES | Location/Qualifiers |
|---|---|
| promoter | 9897..9915<br>/label=T7 promoter<br>/note="promoter for bacteriophage T7 RNA polymerase" |
| promoter | 10698..10716<br>/label=T7 promoter<br>/note="promoter for bacteriophage T7 RNA polymerase" |
| promoter | 11451..11469<br>/label=T7 promoter<br>/note="promoter for bacteriophage T7 RNA polymerase" |

ORIGIN
```
cacattctta agcctgtgga acacctacat ctgtattaac
gaagcgctaa ccgtttttat caggctctgg gaggcagaat
aaatgatcat atcgtcaatt attacctcca cggggagagc
ctgagcaaac tggcctcagg catttgagaa gcacacggtc
acactgcttc cggtagtcaa taaaccggta aaccagcaat
agacataagc ggctatttaa cgaccctgcc ctgaaccgac
gaccgggtcg aatttgcttt cgaatttctg ccattcatcc
gcttattatc acttattcag gcgtagcaac caggcgttta
agggcaccaa taactgcctt aaaaaaatta cgccccgccc
tgccactcat cgcagtactg ttgtaattca ttaagcattc
tgccgacatg gaagccatca caaacggcat gatgaacctg
aatcgccagc ggcatcagca ccttgtcgcc ttgcgtataa
tatttgccca tggtgaaaac gggggcgaag aagttgtcca
tattggccac gtttaaatca aaactggtga aactcaccca
gggattggct gagacgaaaa acatattctc aataaaccct
ttagggaaat aggccaggtt ttcaccgtaa cacgccacat
cttgcgaata tatgtgtaga aactgccgga aatcgtcgtg
gtattcactc cagagcgatg aaaacgtttc agtttgctca
tggaaaacgg tgtaacaagg gtgaacacta tcccatatca
ccagctcacc gtctttcatt gccatacgga attccggatg
agcattcatc aggcgggcaa gaatgtgaat aaaggccgga
taaaacttgt gcttattttt ctttacggtc tttaaaaagg
ccgtaatatc cagctgaacg gtctggttat aggtacattg
agcaactgac tgaaatgcct caaaatgttc tttacgatgc
cattgggata tatcaacggt ggtatatcca gtgatttttt
tctccatttt agcttcctta gctcctgaaa atctcgataa
ctcaaaaaat acgcccggta gtgatcttat ttcattatgg
tgaaagttgg aacctcttac gtgccgatca acgtctcatt
ttcgccaaaa gttggcccag gcttcccgg tatcaacagg
gacaccagga tttatttatt ctgcgaagtg atcttccgtc
acaggtattt attcggcgca aagtgcgtcg ggtgatgctg
ccaacttact gatttagtgt atgatggtgt ttttgaggtg
ctccagtggc ttctgtttct atcagctgtc cctcctgttc
agctactgac ggggtggtgc gtaacggcaa aagcaccgcc
ggacatcagc gctagcggag tgtatactgg cttactatgt
tggcactgat gagggtgtca gtgaagtgct tcatgtggca
ggagaaaaaa ggctgcaccg gtgcgtcagc agaatatgtg
atacaggata tattccgctt cctcgctcac tgactcgcta
cgctcggtcg ttcgactgcg gcgagcggaa atggcttacg
aacggggcgg agatttcctg gaagatgcca ggaagatact
taacagggaa gtgagagggc gcggcaaag ccgttttttcc
ataggctccg ccccctgac aagcatcacg aaatctgacg
ctcaaatcag tggtggcgaa acccgacagg actataaaga
taccaggcgt ttccccctgg cggctccctc gtgcgctctc
ctgttcctgc ctttcggttt accggtgtca ttccgctgtt
atggccgcgt ttgtctcatt ccacgcctga cactcagttc
cgggtaggca gttcgctcca agctggactg tatgcacgaa
cccccccgttc agtccgaccg ctgcgcctta tccggtaact
atcgtcttga gtccaacccg gaaagacatg caaaagcacc
actggcagca gccactggta attgatttag aggagttagt
cttgaagtca tgcgccggtt aaggctaaac tgaaaggaca
agttttggtg actgcgctcc tccaagccag ttacctcggt
tcaaagagtt ggtagctcag agaaccttcg aaaaaccgcc
ctgcaaggcg gttttttcgt tttcagagca agagattacg
cgcagaccaa aacgatctca agaagatcat cttattaatc
agataaaata tttctagatt tcagtgcaat ttatctcttc
aaatgtagca cctgaagtca gccactagtc atatcgggga
tctcgatccc gcgaaattaa tacgactcac tatagggga
ttgtgagcgg ataacaattc ccctctagaa ataattttgt
```

-continued

| 12548 bp ds-DNA; circular DNA construct |
|---|
| FEATURES         Location/Qualifiers |

```
ttaactttaa gaaggagata tacatatggc tagcaccatg
gatatcaagc ttaccggtga attcgctatg gacaaagatt
gcgaaatgaa acgtaccacc ctggatagcc cgctgggcaa
actggaactg agcggctgcg aacagggcct gcatgaaatt
aaactgctgg gtaaaggcac cagcgcggcc gatgcggttg
aagttccggc cccggccgcc gtgctgggtg tccggaacc
gctgatgcag gcgaccgcgt ggctgaacgc gtattttcat
cagccggaag cgattgaaga atttccggtt ccggcgctgc
atcatccggt gtttcagcag gagagcttta cccgtcaggt
gctgtggaaa ctgctgaaag tggttaaatt tggcgaagtg
attagctatc agcagctggc ggccctggcg ggtaatccgg
cggccaccgc cgccgttaaa accgcgctga gcggtaaccc
ggtgccgatt ctgattccgt gccatcgtgt ggttagctct
agcggtgcgg ttggcggtta tgaaggtggt ctggcggtga
aagagtggct gctggcccat gaaggtcatc gtctgggtaa
accgggtctg ggacctgcag tggataagaa atactcaata
ggcttagata tcgcacaaa tagcgtcgga tgggcggtga
tcactgatga ataaaggtt ccgtctaaaa agttcaaggt
tctgggaaat acagaccgcc acagtatcaa aaaaaatctt
ataggggctc ttttatttga cagtggagag acagcggaag
cgactcgtct caaacggaca gctcgtagaa ggtatacacg
tcggaagaat cgtatttgtt atctacagga gattttttca
aatgagatgg cgaaagtaga tgatagtttc tttcatcgac
ttgaagagtc ttttttggtg gaagaagaca agaagcatga
acgtcatcct attttggaa atatagtaga tgaagttgct
tatcatgaga aatatccaac tatctatcat ctgcgaaaaa
aattggtaga ttctactgat aaagcggatt gcgcttaat
ctatttggcc ttagcgcata tgattaagtt tcgtggtcat
tttttgattg agggagattt aaatcctgat aatagtgatg
tggacaaact atttatccag ttggtacaaa cctacaatca
attatttgaa gaaaaccta ttaacgcaag tggagtagat
gctaaagcga ttctttctgc acgattgagt aaatcaagac
gattagaaaa tctcattgct cagctccccg gtgagaagaa
aaatggctta tttgggaatc tcattgcttt gtcattgggt
ttgaccccta attttaaatc aaattttgat ttggcagaag
atgctaaatt acagctttca aaagatactt acgatgatga
tttagataat ttattggcgc aaattggaga tcaatatgct
gatttgtttt tggcagctaa gaatttatca gatgctattt
tactttcaga tatcctaaga gtaaatactg aaataactaa
ggctcccta tcagcttcaa tgattaaacg ctacgatgaa
catcatcaag acttgactct ttaaaagct ttagttcgac
aacaacttcc agaaaagtat aaagaaatct tttttgatca
atcaaaaaac ggatatgcag gttatattga tgggggagct
agccaagaag aattttataa atttatcaaa ccaattttag
aaaaaatgga tggtactgag gaattattgg tgaaactaaa
tcgtgaagat ttgctgcgca agcaacggac ctttgacaac
ggctctattc cccatcaaat tcacttgggt gagctgcatg
ctattttgag aagacaagaa gactttatc cattttaaa
agacaatcgt gagaagattg aaaaaatctt gacttttcga
attccttatt atgttggtcc attggcgcgt ggcaatagtc
gttttgcatg gatgactcgg aagtctgaag aaacaattac
cccatggaat tttgaagaag ttgtcgataa aggtgcttca
gctcaatcat ttattgaacg catgacaaac tttgataaaa
atcttccaaa tgaaaagta ctaccaaaac atagtttgct
ttatgagtat tttacggttt ataacgaatt gacaaaggtc
aaatatgtta ctgaaggaat gcgaaaacca gcatttcttt
caggtgaaca gaagaaagcc attgttgatt tactcttcaa
aacaaatcga aaagtaaccg ttaagcaatt aaaagaagat
tatttcaaaa aaatagaatg ttttgatagt gttgaaattt
caggagttga agatagattt aatgcttcat taggtaccta
ccatgatttg ctaaaaatta ttaaagataa agattttttg
gataatgaag aaaatgaaga tatcttagag gatattgttt
taacattgac cttatttgaa gatagggaga tgattgagga
aagacttaaa acatatgctc acctctttga tgataaggtg
atgaaacagc ttaaacgtcg ccgttatact ggttgggac
gtttgtctcg aaaattgatt aatggtatta gggataagca
atctggcaaa acaatattag atttttgaa atcagatggt
tttgccaatc gcaattttat gcagctgatc catgatgata
gtttgacatt taaagaagac attcaaaag cacagtgtc
tggacaaggc gatagtttac atgaacatat tgcaaattta
gctggtagcc ctgctattaa aaaaggtatt ttacagactg
taaaagttgt tgatgaattg gtcaaagtaa tggggcggca
taagccagaa aatatcgtta ttgaaatggc acgtgaaaat
cagcaactc aaaagggcca gaaaaattcg cgagagcgta
tgaaacgaat cgaagaaggt atcaaagaat taggaagtca
```

-continued

| 12548 bp ds-DNA; circular DNA construct |
|---|
| FEATURES        Location/Qualifiers |

```
gattcttaaa gagcatcctg ttgaaaatac tcaattgcaa
aatgaaaagc tctatctcta ttatctccaa aatggaagag
acatgtatgt ggaccaagaa ttagatatta atcgtttaag
tgattatgat gtcgatcaca ttgttccaca aagtttcctt
aaagacgatt caatagacaa taaggtctta acgcgttctg
ataaaaatcg tggtaaatcg gataacgttc caagtgaaga
agtagtcaaa aagatgaaaa actattggag acaacttcta
aacgccaagt taatcactca acgtaagttt gataatttaa
cgaaagctga acgtggaggt ttgagtgaac ttgataaagc
tggttttatc aaacgccaat tggttgaaac tcgccaaatc
actaagcatg tggcacaaat tttggatagt cgcatgaata
ctaaatacga tgaaaatgat aaacttattc gagaggttaa
agtgattacc ttaaaatcta aattagtttc tgacttccga
aaagatttcc aattctataa agtacgtgag attaacaatt
accatcatgc ccatgatgcg tatctaaatg ccgtcgttgg
aactgctttg attaagaaat atccaaaact tgaatcggag
tttgtctatg gtgattataa agtttatgat gttcgtaaaa
tgattgctaa gtctgagcaa gaaataggca aagcaaccgc
aaaatatttc ttttactcta atatcatgaa cttcttcaaa
acagaaatta cacttgcaaa tggagagatt cgcaaacgcc
ctctaatcga aactaatggg gaaactggag aaattgtctg
ggataaaggg cgagattttg ccacagtgcg caaagtattg
tccatgcccc aagtcaatat tgtcaagaaa acagaagtac
agacaggcgg attctccaag gagtcaattt taccaaaaag
aaattcggac aagcttattg ctcgtaaaaa agactgggat
ccaaaaaaat atggtggttt tgatagtcca acggtagctt
attcagtcct agtggttgct aaggtggaaa aagggaaatc
gaagaagtta aaatccgtta aagagttact agggatcaca
attatggaaa gaagttcctt tgaaaaaaat ccgattgact
ttttagaagc taaaggatat aaggaagtta aaaaagactt
aatcattaaa ctacctaaat atagtctttt tgagttagaa
aacggtcgta aacggatgct ggctagtgcc ggagaattac
aaaaaggaaa tgagctggct ctgccaagca aatatgtgaa
tttttttatat ttagctagtc attatgaaaa gttgaagggt
agtccagaag ataacgaaca aaaacaattg tttgtggagc
agcataagca ttatttagat gagattattg agcaaatcag
tgaattttct aagcgtgtta ttttagcaga tgccaattta
gataaagttc ttagtgcata taacaaacat agagacaaac
caatacgtga acaagcagaa aatattattc atttatttac
gttgacgaat cttggagctc ccgctgcttt taaatatttt
gatacaacaa ttgatcgtaa acgatatacg tctacaaaag
aagttttaga tgccactctt atccatcaat ccatcactgg
tctttatgaa acacgcattg atttgagtca gctaggaggt
gaccccaaga agaagaggaa ggtgatggat aagcatcacc
accaccatca ctaactcgag gttaattaag cggccgcatt
gatccggctg ctaacaaagc ccgaaaggaa gctgagttgg
ctgctgccac cgctgagcaa taactagcat aaccccttgg
ggcctctaaa cgggtcttga gggtttttt gctgaaagga
ggaactatat ccggatgtag aggatcgaga tctcgatccc
gcgaaattaa tacgactcac tatagggaa ttgtgagcgg
ataacaattc ccctctagaa ataattttgt ttaactttaa
gaaggagata tacatatgca tcatcatcat catcatattg
acatgctagt tttacgatta ccgttcatcg attctcttgt
ttgctccaga ctctcaggca atgacctgat agcctttgta
gatctctcaa aaatagctac cctctccggc attaatttat
cagctagaac ggttgaatat catattgta gtgatttgac
tgtctccggc cttcctcacc cttttgaatc tttacctaca
cattactcag gcattgcatt taaaatatat gagggttcta
aaaattttta tccttgcgtt gaaataaagg cttctcccgc
aaaagtatta cagggtcata atgttttttgg tacaaccgat
ttagctttat gctctgaggc tttattgctt aattttgcta
attctttgcc ttgcctgtat gatttattgg atgttaatgc
tactactatt agtagaattg atgccacctt ttcagctcgc
gccccaaatg aaaatatagc taaacaggtt attgaccatt
tgcgaaatgt atctaatggt caaactaaat ctactcgttc
gcagaattgg gaatcaactg ttatatggaa tgaaacttcc
agacaccgta cttagttgc atatttaaaa catgttgagc
tacagcatta tattcagcaa ttaagctcta agccatccgc
aaaaatgacc tcttatcaaa aggagcaatt aaaggtactc
tctaatcctg acctgttgga gtttgcttcc ggtctggttc
gctttgaagc tcgaattaaa acgcgatatt tgaagtcttt
cgggcttcct cttaatcttt ttgatgcaat ccgctttgct
tctgactata atagtcaggg taagacctga ttttttgatt
tatggtcatt ctcgttttct gaactgttta aagcatttga
gggggattca atgaatattt atgacgattc cgcagtattg
```

-continued

| 12548 bp ds-DNA; circular DNA construct |
|---|
| FEATURES　　　　Location/Qualifiers |

```
gacgctatcc agtctaaaca ttttactatt accccctctg
gcaaaacttc ttttgcaaaa gcctctcgct attttggttt
ttatcgtcgt ctggtaaacg agggttatga tagtgttgct
cttactatgc ctcgtaattc cttttggcgt tatgtatctg
cattagttga atgtggtatt cctaaatctc aactgatgaa
tctttctacc tgtaataatg ttgttccgtt agttcgtttt
attaacgtag atttttcttc ccaacgtcct gactggtata
atgagccagt tcttaaaatc gcataaggta attcacaatg
attaaagttg aaattaaacc atctcaagcc caatttacta
ctcgttctgg tgtttctcgt cagggcaagc cttattcact
gaatgagcag ctttgttacg ttgatttggg taatgaatat
ccggttcttg tcaagattac tcttgatgaa ggtcagccag
cctatgcgcc tggtctgtac accgttcatc tgtcctcttt
caaagttggt cagttcggtt cccttatgat tgaccgtctg
cgcctcgttc cggctaagca ccaccaccac caccactaat
ctcgagggtg gtggtagcga ttataaagat gatgatgata
aaggcctgaa cgatatcttt gaagcccaga aaattgaatg
gcacgagtaa aagcttgtcg agcaccacca ccaccaccac
tgagatccgg ctgctaacaa agcccgaaag gaagctgagt
tggctgctgc caccgctgag caataactag cataacccct
tggggcctct aaacgggtct tgaggggttt tttgctgaaa
ggaggaacta tatctaatac gactcactat agctggagaa
ctgtaatgaa ccgtgagagg ctgagtgccg tgggcgccgc
ctaacactgc caatgccggt cccaagcccg gataaaagtg
gaggggggcgg ggagccgttc gggcggctat aaacagacct
caggcccgaa gcgtggcggc ttcggccgcc ggtggtacga
tgcgttgagc taaccggtac aggggggctg ctcctagtac
gagaggaccg gaggtaagcg cagccgccta acactgccaa
tgccggtccc aagcccggat aaaagtggag ggggcgggga
gccgttcggg cggctataaa cagacctcag gcccgaagcg
tggcggcttc ggccgccggt ggtaacgacg ttgattttt
aggccgggtg ttgacgcat cattttctg tgtgttcggaa
gcatctaagt ttttcacgaa acttgccgcc taacactgcc
aatgccggtc ccaagcccgg ataaaagtgg aggggcggg
gagccgttcg ggcggctata aacagacctc aggcccgaag
cgtggcggct tcggccgccg gtggtaaacg ttgaagacgc
cccgagatga gttctccctg acctttaac ttgagagaac
tcgggtgaag gaacacaggt ggtcaggtag agaataccaa
ggcggggtcc tgaaggtaat acgactcact atagactgcc
cggtagctgg cacctcgatg tcggctcatc accgcccaag
agttcatatc gacggcggtg tttaaatgcg gaagagataa
gtgctgagtt gtcatgccaa tggcccgcct aacactgcca
atgccggtcc caagcccgga taaaagtgga ggggcgggga
gccgttcggg cggctataaa cagacctcag gcccgaagcg
agccgttcgg gcggctataa acagacctca ggcccgaagc
gtggcggctt cggccgccgg tggtacggcg gccgtaaaaa
aactataacg gttaatccgg gttaaaagga gacaagaata
aacgctcaat gattttgcag cacttcttgt tatcttaacg
aactgttgat gattcgacag gaggctcaca acaggcaaaa
gcggacagtg tgtgagacag ttaaaaacgg tccctatcgc
gtgatgacga aaaaaggcac tacggccgcc taacactgcc
aatgccggtc ccaagcccgg ataaaagtgg aggggcggg
gagccgttcg ggcggctata aacagacctc aggcccgaag
cgtggcggct tcggccgccg gtggtatttg actgggcgc
gagctgggtt tagaacgtcc tggtgggtag ccgcctaaca
ctgccaatgc cggtcccaag cccggataaa agtggagggg
gcggggagcc gttcgggcgg ctataaacag acctcaggcc
cgaagcgtgg cggcttcggc cgccggtggt ataagagta
acggaggagc acgcaagggt atggctgttc gccatttaaa
gtggtacggt ctcctcctaa tacgactcac tatagcgagc
aggtgctttt tgaaagcagg tctccgggga taatttttca
ggctgataca tcctgggct ttttgaagt aggtccaagg
ttggctattt ttatcctggt cggccgccta acactgccaa
tgccggtccc aagcccggat aaaagtggag ggggcgggga
gccgttcggg cggctataaa cagacctcag gcccgaagcg
tggcggcttc ggccgccggt ggtatcgcgg atggagctga
aattcgggag aaggcacgct gatatgtagg tgaccatcgc
tcaacggata aaaggtacat agtgatccgg tggttctgaa
tggaagggg tccccccgcct aacactgcca atgccggtcc
caagcccgga taaaagtgga ggggcgggg agccgttcgg
gcggctataa acagacctca ggcccgaagc gtggcggctt
cggccgccgg tggtacgagc gtgacggcga catcaggagg
ttagtgcaat ggcataagca tgtgtaggat aggtgggagg
ctttctatag cttgacactg aacattgagc cttgcagctt
gactgccgcc taacactgcc aatgccggtc ccaagcccgg
ataaaagtgg aggggcggg gagccgttcg ggcggctata
```

12548 bp ds-DNA; circular DNA construct

| FEATURES | Location/Qualifiers |
|---|---|

```
aacagacctc aggcccgaag cgtggcggct tcggccgccg
gtggtagaaa ttccttgttg atgttctaac gttgacccgc
ctaaggtagc taatacgact cactatagtc cgacctgcac
gaatggcgta atggagccga ccttgaaata ccacccttta
atgttcgggt aagtccgcct aacactgcca atgccggtcc
caagcccgga taaaagtgga gggggcgggg agccgttcgg
gcggctataa acagacctca ggcccgaagc gtggcggctt
cggccgccgg tggtaggaaa gaccccttt tgtgaacctt
tagaagtgtg gacttttttgc cagtctgcat gatggccagg
tttttctgtc tccaccccgc ctaacactgc caatgccggt
cccaagcccg gataaaagtg gagggggcgg ggagccgttc
gggcggctat aaacagacct caggcccgaa gcgtggcggc
ttcggccgcc ggtggtaagt gtaccgcgg caagaccgag
actcagtgaa attgaactcg ctgtgacaaa cacgaaagtg
gacgtatacg ggcaactgtt tattaaaaac acagcactgt
gagatgcccg cctaacactg ccaatgccgg tcccaagccc
ggataaaagt ggagggggcg gggagccgtt cgggcggcta
taaacagacc tcaggcccga agcgtggcgg cttcggccgc
cggtggtaca aatgccctgt cttgatcgaa gccccggtaa
atgctgaagc aaccgcctaa cactgccaat gccggtccca
agcccggata aaagtggagg gggcggggag ccgttcgggc
ggctataaac agacctcagg cccgaagcgt ggcggcttcg
gccgccggtg gtaagcctct aagcatcagg taacaaaggt
taattgatgg ggttagcgca agcgaagcct tccaggaaac
cgcctaacac tgccaatgcc ggtcccaagc ccggataaaa
gtggaggggg cggggagccg ttcgggcggc tataaacaga
cctcaggccc gaagcgtggc ggcttcggcc gccggtggta
tcaaatcgta cttttttccca aaccgactag gcaaaatgtt
tttgtgccgt aactcagtcg aagatttttt accagctggc
ttgtgacgcc tgttttttccc ggtgccgg
// (SEQ ID NO: 8)
```

Exemplary staple sequences optionally separated by a twister-pistol ribozyme, optional drive by a T7 promotor, and optionally including terminator sequences are also provided. See, e.g., the annotated sequences of Staples1and2, Staples3and4, and Staples1234 below. Staples 1234 is the combination of Staples1and2 and Staples3and4 with the additional terminator sequences as disclosed herein and illustrated in the All-in-one plasmid. The terminator sequence is published in Du, et al., *Biotechnol Bioeng.*, 109(4):1043-50 (2012) and Shepherd, et al., *Nucleic Acids Res.*, 45(18): 10895-10905.

An annotated sequence for "Staples1and2" is

499 bp ds-DNA; natural linear DNA sequence

| FEATURES | Location/Qualifiers |
|---|---|
| source | 1 . . . 499<br>/organism = "unspecified"<br>/mol_type = "genomic DNA" |
| promoter | 2 . . . 20<br>/label = T7 promoter<br>/note = "promoter for bacteriophage T7 RNA polymerase" |
| misc_feature | 19 . . . 185<br>/label = Staple1 |
| misc_feature | 19 . . . 39<br>/label = FAH2_target |
| misc_RNA | 40 . . . 115<br>/label = gRNA scaffold<br>/note = "guide RNA scaffold for the *Streptococcus pyogenes* CRISPR/Cas9 system" |

499 bp ds-DNA; natural linear DNA sequence

| FEATURES | Location/Qualifiers |
|---|---|
| misc_feature | 181 . . . 234<br>/label = TwisterRibozyme |
| misc_feature | 235 . . . 304<br>/label = PistolRibozyme |
| misc_feature | 300 . . . 499<br>/label = Staple2 |
| misc_feature | 342 . . . 430<br>/label = InsulinReceptorAptamer |

```
ORIGIN
ctaatacgac tcactataga cgactggagc agtaatgccg
ttttagagct agaaatagca agttaaaata aggctagtcc
gttatcaact tgaaaagtg gcaccgagtc ggtgcaaaaa
tccgacctgc acgaatgcg taatggagcc gaccttgaaa
taccacccct taatgttcgg gtaagtaaca ctgccaatgc
cggtcccaag cccggataaa agtggagggc ttacactcgt
ttgagcgagt ataaacagcg ccgtaggctc aaagcggaga
gcagattcgt ctgctctcgc ggcggccgta aaaaaactat
aacggttaat ccgggttaaa aggagacaag aataaacgct
caatgatttt gcagcacttc ttgttatctt aacgaactgt
tgatgattcg acaggaggct cacaacaggc aaaagcggac
agtgtgtgag acagttaaaa acggtcccta tcgcgtgatg
acgaaaaaag gcactacgg
// (SEQ ID NO: 62)
```

An annotated sequence for "Staples3and4" is

| 257 bp ds-DNA; natural linear DNA sequence | |
|---|---|
| FEATURES | Location/Qualifiers |
| source | 1 . . . 257<br>/organism = "unspecified"<br>/mol_type = "genomic DNA" |
| promoter | 2 . . . 20<br>/label = T7 promoter<br>/note = "promoter for bacteriophage T7 RNA polymerase" |
| misc_feature | 20 . . . 99<br>/label = Staple3 |
| misc_feature | 95 . . . 148<br>/label = TwisterRibozyme |
| misc_feature | 149 . . . 218<br>/label = PistolRibozyme |
| misc_feature | 214 . . . 257<br>/label = Staple4 |
| ORIGIN | | ctaatacgac tcactatagg aaagacccct ttttgtgaac
ctttagaagt gtggactttt tgccagtctg catgatggcc
aggtttttct gtctccacct aacactgcca atgccggtcc
caagcccgga taaaagtgga ggggtggac tcgtttgagc
gagtataaac agatttctag gctcaaagcg gagagcagat
tcgtctgctc tcggaaattc cttgttgatg ttctaacgtt
gacccgccta aggtagc
// (SEQ ID NO: 63)

An annotated sequence for "Staples1234" is

| 1185 bp ds-DNA; natural linear DNA sequence | |
|---|---|
| FEATURES | Location/Qualifiers |
| source | 1 . . . 1185<br>/organism = "unspecified"<br>/mol_type = "genomic DNA" |
| misc_feature | 1 . . . 22<br>/label = BioBrick prefix<br>/note = "BioBrick prefix for parts that do not start With "ATG"" |
| promoter | 24 . . . 42<br>/label = T7 promoter<br>/note = "promoter for bacteriophage T7 RNA polymerase" |
| misc_feature | 41 . . . 207<br>/label = Staple 1 |
| misc_feature | 41 . . . 61<br>/label = FAH target |
| misc_RNA | 62 . . . 137<br>/label = gRNA scaffold<br>/note = "guide RNA scaffold for the *Streptococcus Pyogenes* CRISPR/Cas9 system" |
| misc_feature | 138 . . . 207<br>/label = Complementary to Scaffold |
| misc_feature | 203 . . . 256<br>/label = Twister Ribozyme |

-continued

| 1185 bp ds-DNA; natural linear DNA sequence | |
|---|---|
| FEATURES | Location/Qualifiers |
| misc_feature | 207 . . . 208<br>/label = Twister Cut |
| misc_feature | 257 . . . 326<br>/label = Pistol Ribozyme |
| misc_feature | 321 . . . 322<br>/label = Pistol Cut |
| misc_feature | 322 . . . 521<br>/label = Staple 2 |
| misc_feature | 322 . . . 363<br>/label = Complementary to Scaffold |
| misc_feature | 364 . . . 452<br>/label = Insulin receptor RNA aptamer |
| misc_feature | 453 . . . 521<br>/label = Complementary to Scaffold |
| misc_feature | 517 . . . 570<br>/label = Twister Ribozyme |
| misc_feature | 521 . . . 522<br>/label = Twister Cut |
| terminator | 571 . . . 588<br>/label = VSV terminator |
| terminator | 596 . . . 714<br>/label = Tphi Terminator |
| promoter | 716 . . . 734<br>/label = T7 promoter<br>/note = "promoter for bacteriophage T7 RNA polymerase" |
| misc_feature | 734 . . . 813<br>/label = Complementary to Scaffold |
| misc_feature | 734 . . . 813<br>/label = Staple 3 |
| misc_feature | 809 . . . 862<br>/label = Twister Ribozyme |
| misc_feature | 813 . . . 814<br>/label = Twister Cut |
| misc_feature | 863 . . . 932<br>/label = Pistol Ribozyme |
| misc_feature | 927 . . . 928<br>/label = Pistol Cut |
| misc_feature | 928 . . . 971<br>/label = Complementary to Scaffold |
| misc_feature | 928 . . . 971<br>/label = Staple 4 |
| misc_feature | 967 . . . 1020<br>/label = Twister Ribozyme |
| misc_feature | 971 . . . 972<br>/label = Twister Cut |
| terminator | 1021 . . . 1038<br>/label = VSV Terminator |

-continued

| 1185 bp ds-DNA; natural linear DNA sequence | |
|---|---|
| FEATURES | Location/Qualifiers |
| terminator | 1046 . . . 1164<br>/label = Tphi Terminator |
| misc_feature | 1165 . . . 1185<br>/label = BioBrick suffix<br>/note = "universal suffix for all parts" |

```
ORIGIN
gaattcgcgg ccgcttctag agctaatacg actcactata
gacgactgga gcagtaatgc cgttttagag ctagaaatag
caagttaaaa taaggctagt ccgttatcaa cttgaaaaag
tggcaccgag tcggtgcaaa aatccgacct gcacgaatgg
cgtaatggag ccgaccttga aataccaccc tttaatgttc
gggtaagtaa cactgccaat gccggtccca agcccggata
aaagtggagg gcttacactc gtttgagcga gtataaacag
cgccgtaggc tcaaagcgga gagcagattc gtctgctctc
gcggcggccg taaaaaaact ataacggtta atccgggtta
aaaggagaca agaataaacg ctcaatgatt ttgcagcact
tcttgttatc ttaacgaact gttgatgatt cgacaggagg
ctcacaacag gcaaaagcgg acagtgtgtg agacagttaa
aaacggtccc tatcgcgtga tgacgaaaaa aggcactacg
gtaacactgc caatgccggt cccaagcccg gataaaagtg
gagggccgta tatctgttag ttttttttcta ctagactgct
aacaaagccc gaaaggaagc tgagttggct gctgccaccg
ctgagcaata actagcataa ccccttgggg cctctaaacg
ggtcttgagg ggtttttttgc tgaaaggagg aactctaata
cgactcacta taggaaagac cccttttttgt gaacctttag
aagtgtggac tttttgccag tctgcatgat ggccaggttt
ttctgtctcc acctaacact gccaatgccg gtcccaagcc
cggataaaag tggagggggt ggactcgttt gagcgagtat
aaacagattt ctaggctcaa agcggagagc agattcgtct
gctctcggaa attccttgtt gatgttctaa cgttgacccg
cctaaggtag ctaacactgc caatgccggt cccaagcccg
gataaaagtg gaggggctac tatctgttag tttttttcta
ctagactgct aacaaagccc gaaaggaagc tgagttggct
gctgccaccg ctgagcaata actagcataa ccccttgggg
cctctaaacg ggtcttgagg ggtttttttgc tgaaaggagg
aacttactag tagcggccgc tgcag
// (SEQ ID NO: 64)
```

V. Kits

Kits for use with the methods disclosed herein are also disclosed. The kits can include one or more of phagemid(s), plasmid(s) (e.g., helper plasmid(s)), host cells, and reagents for carrying various cloning and expression techniques related thereto including, but not limited to buffers, primers, enzymes, dNTPs, and other active agents and organics that facilitate various steps of the disclosed reactions. The kits can also include instructions for use. The present invention will be further understood by reference to the following non-limiting examples.

The disclosed compositions and methods can be further understood through the following numbered paragraphs.

1. An isolated nucleic acid comprising or encoding
   (i) a bacteriophage origin of replication,
   (ii) a bacteriophage packaging signal, and
   (iii) a heterologous target single-strand DNA (ssDNA) sequence of interest,
   wherein the isolated nucleic acid does not comprise or encode a plasmid origin of replication.
2. The isolated nucleic acid of paragraph 1 further comprising or encoding a selectable marker.
3. The isolated nucleic acid of paragraphs 1 or 2, wherein the isolated nucleic acid is single stranded.
4. The isolated nucleic acid of paragraphs 1 or 2, wherein the isolated nucleic acid is double stranded.
5. The isolated nucleic acid of any one of paragraphs 1-4, wherein the isolated nucleic acid is circular.
6. The isolated nucleic acid of any one of paragraphs 1-4, wherein the isolated nucleic acid is linear.
7. The isolated nucleic acid of any one of paragraphs 1 or 2, wherein the isolated nucleic acid is circular and double stranded.
8. The isolated nucleic acid of any one of paragraphs 1-7, wherein the target ssDNA sequence of interest is a scaffold sequence.
9. The isolated nucleic acid of paragraph 8, wherein the scaffold sequence can form a 2D or 3D DNA origami structure.
10. The isolated nucleic acid of any one of paragraphs 1-9, wherein the target ssDNA sequence of interest encodes bitstream data.
11. A host cell comprising the isolated nucleic acid of any one of paragraphs 1-10.
12. The host cell of paragraph 11, further comprising a double stranded nucleic acid helper plasmid, wherein the helper plasmid encodes one or more bacteriophage factors capable of packaging a single strand of the isolated nucleic acid into a bacteriophage particle, and wherein the helper plasmid lacks a packaging signal.
13. The host cell of paragraphs 11 or 12 wherein the helper plasmid, or a second plasmid, encodes one or more additional functional elements that can be incorporated into or onto the target ssDNA of interest.
14. The host cell of paragraph 13 wherein the one or more functional elements are selected from the group consisting of single-guide- or crispr-RNAs (crRNA), anti-sense DNA, anti-sense RNA, one or more proteins, or a combination thereof.
15. The host cell of paragraph 14, wherein the anti-sense RNA is selected from the group consisting of RNAi, miRNA, piRNA and siRNA.
16. The host cell of paragraph 14, wherein the one or more proteins is a Cas protein, TAL effector protein, or zinc-finger protein.
17. The host cell of any one of paragraphs 13-16, wherein the functional elements comprise single-guide- or crispr-RNAs (crRNA) alone or in combination with a Cas protein.
18. The host cell of any one of paragraphs 11-17 wherein the host cell comprises a lipopolysaccharide pathway, and wherein the lipopolysaccharide pathway is disrupted.
19. The host cell of any one of paragraph 11-18 wherein the host cell lacks a functional RNase H gene (rnh).
20. The host cell of any one of paragraphs 11-20, wherein the host cell expresses one or more stable strand nucleic acids that facilitate folding of the ssDNA into a 2D or 3D DNA origami structure.
21. A phagemid comprising the nucleic acid sequence of any one of SEQ ID NO:1, or 4-7, or a variant thereof with at least 75%, 80%, 85%, 90%, or 95% sequence identity to any one of SEQ ID NO:1, or 4-7.
22. A phagemid comprising the backbone of SEQ ID NO:1 or 4-7, wherein a target single-strand DNA (ssDNA) sequence of interest is inserted into the backbone or substituted for an existing sequence without disrupting the bacteriophage origin of replication or sequence encoding the bacteriophage packaging signal.
23. A variant of the phagemid of any one of SEQ ID NO:1 or 4-7 comprising a nucleic acid sequence encoding a bacteriophage origin of replication, absence of a plasmid origin of replication, and optionally nucleic acid sequences encoding a selectable marker and/or a target single-strand DNA (ssDNA) sequence of interest, wherein the bacteriophage origin of replication is substituted with an alternative origin of replication, any selectable marker is substituted with an alternative selectable marker or deleted, any target single-strand DNA (ssDNA) sequence of interest is substituted with an alternative target single-strand DNA (ssDNA) sequence of interest or deleted, or a combination thereof relative to SEQ ID NO:1 or 4-7.

24. A plasmid comprising the nucleic acid sequence of SEQ ID NO:8, or a variant thereof with at least 75%, 80%, 85%, 90%, or 95% sequence identity to SEQ ID NO:8.

25. A method of assembling two or more nucleic acid sequences to form a long single-stranded nucleic acid scaffold sequence for a nucleic acid nanostructure, comprising the steps of
   (a) mixing two or more nucleic acids to create a reaction mix,
      wherein the two or more nucleic acids comprise
         (i) the nucleic acid sequence corresponding to the origin of replication from a class 1 filamentous bacteriophage; and
         (ii) one or more naturally or non-naturally occurring nucleic acid sequences of between 1 and 1,000,000 nucleotides in length; and
         (iii) optionally a nucleic acid sequence corresponding to one or more selection markers;
   (b) producing a long single-stranded nucleic acid scaffold sequence from the reaction mix using asymmetric Polymerase Chain Reaction (aPCR),
      wherein the long single-stranded nucleic acid scaffold comprises the one or more naturally or non-naturally occurring nucleic acid sequences within the reaction mix.

26. The method of paragraph 25, wherein the step of (b) producing a long single-stranded nucleic acid from the reaction mix using aPCR further comprises mutagenizing the long single-stranded nucleic acid.

27. The method of paragraph 25, wherein mutagenizing the long single-stranded nucleic acid comprises exposure to an agent selected from MnSO₄, caffeine, or Ultra Violet (UV) light.

28. The method of any one of paragraphs 25-27, wherein the single-stranded nucleic acid is complementary by 1, 2, 3, 4, 5, or 6 nucleotides, or greater than 6 nucleotides, to a second single-stranded nucleic acid generated by asymmetric PCR.

29. The method of paragraph of any one of paragraphs 25-28, wherein long single-stranded nucleic acid scaffold sequence is a phagemid of between 400 and 1,000,000 nucleotides in length.

30. The method of any one of paragraphs 25-29, wherein the origin of replication from a class 1 filamentous bacteriophage is the 427 nucleotide f1-origin of replication.

31. The method of any one of paragraphs 25-30, wherein the nucleic acid sequence corresponding to one or more selection markers is the 1,249-nt ampicillin resistance cistron.

32. The method of any one of paragraphs 25-31, further comprising the step of
   (c) producing a double-stranded nucleic acid corresponding to the long single stranded nucleic acid sequence using a polymerase enzyme.

33. The method of paragraph 32, wherein complementarity exists on two regions of the second strand to delete or remove sequences from a plasmid.

34. The method of any one of paragraphs 25-33, further comprising the step of
   (d) encapsulating the long single-stranded nucleic acid scaffold sequence within a bacteriophage particle,
      wherein the nucleic acid within the bacteriophage particle comprises less than 10%, less than 5%, preferably less than 1% weight:weight of double-stranded DNA.

35. A method for the in vivo production of a long single-stranded nucleic acid scaffold sequence of between 1 and 1,000,000 nucleotides in length, comprising the steps of
   (a) producing a long single-stranded nucleic acid sequence that is a scaffold for a nucleic acid nanoparticle formation within an microorganism;
   (b) packaging the long single-stranded nucleic acid scaffold sequence within a bacteriophage particle within the microorganism; and
   (c) isolating the long single-stranded nucleic acid scaffold sequence from the bacteriophage particle.

36. The method of paragraph 35, further comprising the step of
   (d) folding the long single-stranded nucleic acid scaffold sequence into a nucleic acid nanoparticle.

37. The method of paragraphs 35 or 36, wherein the step of (c) isolating the long single-stranded nucleic acid scaffold sequence from the bacteriophage particle comprises harvesting phage particles directly from clarified growth media.

38. The method of paragraph 37, wherein the harvesting comprises or consists of
   (i) buffer-exchanging the clarified growth media; and
   (ii) concentrating the phage particles.

39. The method of any one of paragraphs 36-38, wherein the folding does not require removal of double-stranded DNA.

40. The method of any one of paragraphs 35-39, wherein the microorganism is selected from the group consisting of a bacterium, a protozoan, a fungi, and an algae.

41. The method of any one of paragraphs 35-40, further comprising the step of isolating the single-stranded nucleic acid scaffold sequence from the microorganism.

42. The method of paragraph 41, wherein the step of isolating the single-stranded nucleic acid scaffold sequence from the microorganism comprises
   (i) lysing the organism to create a lysate; and
   (ii) optionally isolating the DNA origami nanoparticle from the lysate.

43. The method of paragraphs 35-42, wherein folding the nanoparticle comprises incubating the organism at a temperature that enables hybridization and folding of the ssDNA scaffold into a nanoparticle.

44. The method of paragraph 43, wherein the temperature that enables hybridization and folding of the DNA scaffold into a nanoparticle is 37 degrees C.

45. The method of paragraph 43, wherein the temperature that enables hybridization and folding of the DNA scaffold into a nanoparticle is room temperature or 21 degrees C.

46. The method of paragraph 43, wherein the temperature that enables hybridization and folding of the DNA scaffold into a nanoparticle is any target temperature based on the hybridization properties of the sequence and staple strands that may be LNA, PNA, RNA, or DNA.

47. The method of any one of paragraphs 35-42, wherein the single-stranded nucleic acid sequence is produced in the organism at a temperature that does not facilitate hybridization or folding of the ssDNA scaffold into a nanoparticle, such that hybridization and folding are initiated by exposure of the organism to the required temperature.

48. The method of any one of paragraphs 35-47, wherein the microorganism is a bacteria.

49. The method of paragraph 48, wherein the bacteria is a strain of *Escherichia coli*.

50. The method of any one of paragraphs 25-49, wherein the nucleic acid nanostructure or nanoparticle includes paranemic crossover motifs.

51. The method of paragraph 50, wherein the crossover motifs are PX-only, DX-only, or some combination of PX- and DX-crossovers.

52. The method of any one of paragraphs 25-50, wherein the single-stranded nucleic acid is directly folded into a nucleic acid nanoparticle or nanostructure without removal of double stranded DNA.

53. The method of any one of paragraphs 25-52, wherein folding the single stranded nucleic acid into a nucleic acid nanostructure or nanoparticle is carried out using a buffer.

54. The method of paragraph 53, wherein the folding buffer comprises 1-, 2-, 21, 22- or more than 22-fold molar excess of one or more staple strands.

55. The method of paragraphs 53 or 54, wherein the folding buffer comprises 2, 3, 4, 5, 6, 7, 8, 9, 10, 11, 12, 13, 14, 15, 16, 17, 18, 19, 20 or greater than 20 mM MgCl2.

56. The method of any one of paragraphs 53-55, wherein the folding buffer further comprises sodium dodecyl sulfate, triton ×100, or other detergents.

57. The method of any one of paragraphs 25-56, wherein the single-stranded nucleic acid sequence comprises digital bitstream data.

58. The method of paragraph 57, wherein the single-stranded nucleic acid sequence comprises a bait or capture sequence that can anneal or bind biological materials including DNA, RNA, or nucleic-acid-binding proteins.

59. The method of paragraph 58, wherein the bait or capture sequence can anneal or bind a gene editing ribonucleoprotein complex.

60. The method of any one of paragraphs 25-59, wherein the single-stranded nucleic acid sequence comprises the scaffold sequence of a nucleic acid nanoparticle that can fold in the absence of one or more staple sequences.

61. A nucleic acid nanoparticle folded from the single single-stranded nucleic acid sequence according to the method of any one of paragraphs 25-60.

62. A single-stranded nucleic acid scaffold sequence produced according to the method of any one of paragraphs 25-34.

63. The single-stranded nucleic acid scaffold sequence of paragraph 62, wherein the nucleic acid sequence encodes digital bitstream data.

64. The single-stranded nucleic acid scaffold sequence of any one of paragraphs 62-63, wherein the nucleic acid scaffold sequence comprises a bait or capture sequence that can anneal or bind biological materials including DNA, RNA, or nucleic-acid-binding proteins.

65. The single-stranded nucleic acid scaffold sequence of paragraph 64, wherein the nucleic-acid-binding protein is specific for a gene editing ribonucleoprotein complex.

66. The single-stranded nucleic acid scaffold sequence of any one of paragraphs 62-65, wherein the scaffold sequence folds into a nucleic acid nanoparticle without staples.

67. The single-stranded nucleic acid scaffold sequence of any one of paragraphs 62-65, wherein the scaffold sequence folds into a nucleic acid nanoparticle with 1, 2, 3, or more than 3 staples.

68. The single-stranded nucleic acid scaffold sequence of paragraph 63-67, wherein the scaffold sequence folds into a nucleic acid nanoparticle with 1, 2, 3, or more than 3 staples using either PX-only, DX-only, or some combination of PX- and DX-crossovers.

69. A microorganism that produces pure single stranded nucleic acid of a user-defined length and sequence, the microorganism comprising
(a) a phagemid,
wherein the phagemid comprises a phage origin of replication and a single stranded nucleic acid scaffold of a user-defined length and sequence and lacks a plasmid origin or replication; and
(b) a double stranded nucleic acid helper plasmid,
wherein the helper plasmid comprises genes of the corresponding phage and optionally lacks the phage packaging signal.

70. The microorganism of paragraph 69, wherein the origin of replication is the f1 or M13 origin of replication.

71. The microorganism of paragraphs 69 or 70, wherein the plasmid lacks the genes encoding the major coat protein.

72. The microorganism of any one of paragraphs 69-71, wherein the only phage genes the plasmid comprises correspond to those required for replication of the phagemid.

73. The microorganism of any one of paragraphs 69-72 wherein the plasmid encodes one or more transcribable RNAs that can serves as one or more staples of the single stranded nucleic acid scaffold.

74. The microorganism of paragraph 73 comprising two or more transcribable RNAs, wherein the transcribable RNAs are separated by transcription terminators and initiated by transcription promoters.

75. The microorganism of paragraphs 73 or 74 wherein the transcribable RNAs comprise a ribozyme or ribozymes that cleaves the RNA into two or more staple sequences.

76. The microorganism of paragraph 75, where the ribozymes are Twister and Pistol ribozymes that cleave near their 5' and 3' ends, respectively.

77. The microorganism of any one of paragraph 69-76, wherein the microorganism comprises the genome of the M13 bacteriophage.

78. A bacteriophage produced by the microorganism of paragraph any one of paragraphs 69-77.

79. The bacteriophage of paragraph 78, wherein the total amount of DNA within the bacteriophage particle comprises less than 10%, less than 5%, preferably less than 1% weight:weight of double-stranded DNA.

80. The bacteriophage of any one of paragraphs 78 or 79, wherein the bacteriophage genome is mutated to disrupt the capsid package to directly export ssDNA to the media.

EXAMPLES

Example 1: Plasmid Assembly by Single-Stranded DNA

Methods

All sequences of primers and templates are provided in Table 1.

TABLE 1

Staples for pentagonal bipyramid nanoparticle from pPB52 phagemid.

| | |
|---|---|
| pbip52_1-1293-V | TCTCAACAGCGTTTTTGTAAGATCCTAACAT GGGGGATTTTTTCATGTAACT (SEQ ID NO: 18) |
| pbip52_1-1520-E | TTTTTCTAAAAGTGGGTTACATCGAACTGGA CTATTTGTTTA (SEQ ID NO: 19) |

TABLE 1-continued

Staples for pentagonal bipyramid nanoparticle from pPB52 phagemid.

| Name | Sequence |
|---|---|
| pbip52_1-1510-E | TACATTCAAATGGGTGCACG (SEQ ID NO: 61) |
| pbip52_2-1261-E | GCCCCGAAGAGAGCTAACCGCTTTTTTGCACTGAGAGTTTTC (SEQ ID NO: 20) |
| pbip52_2-1251-E | ACGTTTTCCAAGGACCGAAG (SEQ ID NO: 21) |
| pbip52_3-1088-V | GTAAGAGAATTTTTTTATGCAGTGCTCTTACTTCTGATTTTTCAACGATCGGATGATGAGCACTTTTTTTTTAAAGTT (SEQ ID NO: 22) |
| pbip52_3-783-E | TCTGCGCTGGCGGATAAAGTTGCAACGGATG (SEQ ID NO: 23) |
| pbip52_3-1096-E | GCATGACAACAGAAAAGCATCTTGGACCACT (SEQ ID NO: 24) |
| pbip52_4-880-V | CAACGTTGCGCTTTTTAAACTATTAAGACAGATCGCTTTTTTGAGATAGGTG (SEQ ID NO: 25) |
| pbip52_4-1043-E | GCGGCCAAGCCATAACCATGAGTGCTGTAGC (SEQ ID NO: 26) |
| pbip52_4-888-E | AATGGCAAGTGACACCACGATGCATAACACT (SEQ ID NO: 27) |
| pbip52_5-484-E | ATCTCATGACCGCTACAGGGCGCCACTTTTCCCTTTTTGATA (SEQ ID NO: 28) |
| pbip52_5-474-E | CAAAATCCCTCTTAAAGCGC (SEQ ID NO: 29) |
| pbip52_6-516-V | TAAAAGGATCTTTTTTAGGTGAAGATGGGGAAATGTGTTTTTCGCGGAACCC (SEQ ID NO: 30) |
| pbip52_6-951-E | TTGGGAACCGTTTAAAACTTCATTTTTAATTCGCCTTGATCG (SEQ ID NO: 31) |
| pbip52_6-941-E | GAGCTGAATGTTTAGATTGA (SEQ ID NO: 32) |
| pbip52_7-568-V | ACCAAGTTTACTTTTTTCATATATACAAGCCATACCATTTTTAACGACGAGC (SEQ ID NO: 33) |
| pbip52_7-419-E | TTAAATTTTGAGCGTCAGACCCCAATTGGTA (SEQ ID NO: 34) |
| pbip52_7-576-E | ACTGTCAGCCTCACTGATTAAGCAATTCGCG (SEQ ID NO: 35) |
| pbip52_8-828-V | ACAATTAATAGTTTTTACTGGATGGACGGCCCTTCCGTTTTTGCTGGCTGGT (SEQ ID NO: 36) |
| pbip52_8-848-E | CTTACTCTAGCAACTATGGATGAACGAAATACTGGCGAACTA (SEQ ID NO: 37) |
| pbip52_8-838-E | CTTCCCGGCAGGGAGTCAGG (SEQ ID NO: 38) |
| pbip52_9-1190-V | GACGCCGGGCATTTTTAGAGCAACTCTTGGTTGAGTATTTTTCTCACCAGTC (SEQ ID NO: 39) |
| pbip52_9-1345-V | TAAAAGATGCTTTTTTGAAGATCAGTTATGTATCCGCTTTTTTCATGAGACA (SEQ ID NO: 40) |
| pbip52_9-1353-E | GGTGAAAGTGTTTTTGCTCACCCAGTATTAT (SEQ ID NO: 41) |
| pbip52_9-1198-E | CCCGTATTCTGCTATGTGGCGCGGAAACGCT (SEQ ID NO: 42) |
| pbip52_10-157-E | GCCCCCGACACTAAATCGGAACCCCGCCCTT (SEQ ID NO: 43) |
| pbip52_10-1406-E | ATTCCCTTTCAACATTTCCGTGTTAAAGGGA (SEQ ID NO: 44) |
| pbip52_11-1449-V | AAAAAGGAAGATTTTTGTATGAGTATTTTTGCGGCATTTTTTTTTGCCTTCC (SEQ ID NO: 45) |
| pbip52_11-44-V | GTAACCACCACTTTTTACCCGCCGCGTAACGTGAGTTTTTTTTTCGTTCCACTTGTTAAATCATTTTTGCTCATTTTT (SEQ ID NO: 46) |
| pbip52_11-52-E | CGCTGCGCGGGCGCTGGCAAGTGTGCTTCAA (SEQ ID NO: 47) |
| pbip52_11-1457-E | TAATATTGATAACCCTGATAAATAGCGGTCA (SEQ ID NO: 48) |
| pbip52_12-308-V | AACAAGAGTCCTTTTTACTATTAAAGCGTCTATCAGGTTTTTGCGATGGCCC (SEQ ID NO: 49) |
| pbip52_12-328-E | TGAGTGTTGTTGGCGAGAAAGGAAGGGAAGACGAGATAGGGT (SEQ ID NO: 50) |
| pbip52_12-318-E | TCCAGTTTGGCCGGCGAACG (SEQ ID NO: 51) |
| pbip52_13-202-V | TGGGGTCGAGGTTTTTTGCCGTAAAGTTTAGAGCTTGTTTTTACGGGGAAAG (SEQ ID NO: 52) |
| pbip52_13-210-E | AAGTTTTTACTACGTGAACCATCATATTCTC (SEQ ID NO: 53) |
| pbip52_13-1147-E | AGAATGACGGTCGCCGCATACACCCCTAATC (SEQ ID NO: 54) |
| pbip52_14-360-V | TTATAAATCAATTTTTAAGAATAGACAAGCGAAAGGATTTTTGCGGGCGCTA (SEQ ID NO: 55) |
| pbip52_14-679-E | CCTCCCGTCAGCACTGGGGCCAGAAATCGGC (SEQ ID NO: 56) |
| pbip52_14-368-E | AAAATCCCTAACCAATAGGCCGATGGTAAGC (SEQ ID NO: 57) |
| pbip52_15-724-V | GTGGGTCTCGCTTTTTGGTATCATTGATCGTAGTTATTTTTCTACACGACG (SEQ ID NO: 58) |
| pbip52_15-263-E | CGAAAAACAACGTGGACTCCAACGCTGGAGC (SEQ ID NO: 59) |
| pbip52_15-732-E | CGGTGAGCTTATTGCTGATAAATTCAAAGGG (SEQ ID NO: 60) |

The sequence from the f1-origin of replication was ordered from Integrated DNA Technologies (IDT, Inc., Coralville, Iowa) as a GBLOCK™ with 20 nt primers flanking the 5' and 3' sides designed to have a calculated melting temperature of 57° C. Single stranded DNA was generated by first amplifying the GBLOCK f1 sequence with PHUSION™ polymerase, followed by gel purification and silica column cleanup. Asymmetric polymerase chain reaction was subsequently applied using 200 ng of purified dsDNA and 1 uM of the 5'-phosphorylated 3' reverse primer with QUANTABIO ACCUSTART HIFI polymerase, as previously described (Veneziano, et al. bioRxiv. (2017)). The beta-lactamase (bla) ampicillin resistance gene (ApR) and its promoter and terminator sequences were amplified from the widely available pUC19 plasmid using PHUSION™ polymerase and New England Biolabs (NEB, Inc., Ipswich, Mass.) PHUSION HF buffer using a 3' reverse primer and a 5' primer that is additionally extended on the 5' side by the reverse complement of the reverse primer of the f1 gBlock fragment. The amplicon was gel- and column-purified. Asymmetric PCR was then used to amplify single-stranded DNA using 200 ng of purified amplicon as a template with QUANTABIO ACCUSTART HIFI buffer and enzyme and 1 uM 5'-phosphorylated reverse primer. The two single-stranded DNA products were then mixed in a 1:1 molar ratio and the ssDNA was converted to dsDNA using Phusion polymerase, followed by amplification using the flanking forward and reverse phosphorylated primers, and subsequently purified. Blunt-end ligation using T4 DNA ligase (NEB) in 1×T4 DNA ligation buffer with 30 ng of amplified DNA incubated at room temperature overnight was then used to close the plasmid.

E. coli strain DH5aF were made competent by washing log-phase grown cells in ice cold 100 mM $CaCl_2$. Competent cells were transformed with 1 ng of helper plasmid DNA and 2 µL of plasmid DNA ligation mix were added to 20 µL of cells. Cells were incubated on ice for 30 minutes, heat shocked at 42° C. for 45 seconds, put back on ice before added pre-warmed SOB media and shaken at 37° C. for 1 hour. 100 µL was plated evenly across a Luria Agar (LA) media plate made with 100 µg/mL ampicillin and 15 µg/mL chloramphenicol.

Single, individual colonies were selected and grown in 5 mL of Terrific Broth (TB) supplemented with 1% glycerol for 36 hours at 37° C. 1 mL of the growth was then removed to a 1.5 mL spin column and spun in a centrifuge at 4,000 rpm for 5 minutes. Supernatant was removed and placed in a new 1.5 mL spin column and spun at 4,000 rpm for an additional 10 minutes. 1 µL of the supernatant was added to 20 uL of nuclease-free water and heated to 95 C for 5 minutes. 1 µL of the heated solution was added to a PHUSION PCR mix containing enzyme, buffer, nucleotides, and forward and reverse primers used to generate the plasmid. Positive colonies were determined by the presence of the amplicon from the media as determined by agarose gel. Positive colonies were sent for Sanger sequencing.

Results

Of 8 colonies chosen, two were shown to be positive for the correct sequence.

This method can be used to generate phagemid containing ampicillin resistance for selection with only an f1-origin of replication. The use of asymmetric PCR described here generally allows for synthesis of any naturally or non-naturally occurring DNA sequence onto a plasmid assembled by overlapping sequences at the 3' ends of the DNA followed by sequence completion and amplification by standard PCR methods.

Example 2: Recombinant Phage Production

Methods

Phage (sPhage) producing colonies, as judged by positive PCR, gel visualization, and sequencing, were grown in 5 mL TB supplemented with glycerol, as recommended by the manufacturer (Sigma-Aldrich, Inc.), inoculated by a single colony from an Luria-Agar plate. The colony was grown in a 15 mL culture tube shaken at 200 RPMs at 37° C. for 36-48 hours. The culture was then spun down in 2 mL centrifuge tubes at 4,000 RPMs for 5 minutes, the supernatant was removed to a fresh tube and spun at 4,000 RPMs for an additional 10 minutes. The supernatant (approximately 5 mL) was refrigerated until ready for DNA preparation.

SPhage particles containing the f1-origin were precipitated by adding 10% acetate pH 5.2 and 2.5 volumes of 100% ethanol and freezing at −20 C for at least 1 hour, or, alternatively, by adding 6% polyethylene glycol 8000 (PEG 8000) final concentration and shaking at 37 C for 30 minutes. Precipitated sPhage were pelleted by centrifugation at 13,000 RPMs for 10 minutes in PEG 8000 or at 4 C at 13,000 RPMs for 30 minutes in ethanol. Supernatant was removed and the pellet. The sPhage pellet was brought up in Tris-buffered 2% sodium dodecyl sulfate (SDS) and heated to 70 C for 30 minutes. The lysed sPhage was ran through a silica-based column (QIAGEN ENDOFREE MAXIPREP, THERMOFISHER HIPURE) to purify the DNA following the manufacturers' protocols. DNA was eluted in 10 mM Tris-HCl elution buffer. Yields of up 750 µg are theoretically attainable with 1 liter of culture.

Method B (Alternative Approach)

SPhage producing colonies, as judged by positive PCR, gel visualization, and sequencing, were grown in 10 mL TB supplemented with glycerol, as recommended by the manufacturer (Sigma-Aldrich, Inc.), inoculated by a single colony from a Luria-Agar plate. The colony was grown in a 15 mL culture tube shaken at 200 RPM at 37° C. for 36-48 hours. The culture was then spun down in 2 mL centrifuge tubes at 4,000 RPM for 30 minutes at 4 C, the supernatant was removed to fresh tubes and spun at 4,000 RPM for an additional 30 minutes at 4 C. The supernatant (approximately 10 mL) was run through a silica-based column (QIAGEN MINIPREP) to purify the DNA following the manufacturer's protocols, besides the lysis step, at which the supernatant was heated at 80° C. for 10 minutes to lyse the sPhage particles. All spin steps were performed at 4 C. DNA was eluted in 30 uL $ddH_2O$.

DNA Origami Assembly

DNA purified from the sPhage was used to fold a pentagonal bipyramid with edge length 52 base pairs. The particle was generated by using staples generated from an automated scaffold routing and staple design software DAEDALUS (Veneziano, R et al., Science, 352, 1534 (2016)). The staples were synthesized by Integrated DNA Technologies (IDT, Inc., Coralville, Iowa). 20 nM of bacterially produced scaffold was incubated with 20-molar excess of staples in 1× Tris-Acetate-EDTA buffer with 12 mM $MgCl_2$. The object was annealed over 13 hours from 95° C. to 24° C. The folded particle was run against the ssDNA scaffold and a clear gel shift was indicated, indicating folding of the particle. Particle folding was also verified using high-resolution transmission electron microscopy.

DNA Origami Assembly Direct from Phage.

Phage was collected from the media by first purifying away from bacteria by 2 rounds of centrifugation at 4,000 RPMs for 30 minutes. The supernatant was then concentrated on a 100 kDa MWCO spin concentrator (Amicon) and brought to equivalent volumes with 1×TAE buffer with 12 mM MgCl2 3 times. 20 nM phage material was combined with 400 nM staples in 1×TAE buffer with 12 mM $MgCl_2$ and 0.2% sodium dodecyl sulfate (SDS) in 50 µL total volume. The solution was annealed over 13 hours from 95°

C. to 24° C. and the folded particle was run on an agarose gel with the ssDNA scaffold for reference.

Transmission Electron Microscopy.

The structured DNA pentagonal bipyramid with 52-base-pair edge length assembled using the phage-produced scaffold was visualized by transmission electron microscopy (TEM). 200 µL of folded reaction was buffer exchanged into 20 mM Tris-HCl pH 8.1 and 12 mM MgCl2 using a 100 kDa MWCO spin concentrator (Amicon, Merck Millipore, Billerica, Mass.) and concentrated to 40 nM. Carbon film with copper grids (CF200H-CU; Electron Microscopy Sciences Inc., Hatfield, Pa.) were glow discharged and sample was applied for 45 seconds. The sample was then blotted from the grid using Whatman 42 ashless paper, and the grid was placed on 2% uranyl-formate with 5 mM NaOH for 30 s. Remaining stain was wicked away using Whatman 42 paper and dried before imaging. The grid was imaged on a Technai FEI with a Gatan camera.

Results

DNA was produced in vivo with minimal sequence requirements. One limitation in such a system is the cloning and production of custom phagemids containing only the f1-origin, and existing systems are therefore often cloned with the high-copy double-stranded pUC or similar origins.

Figure 7:
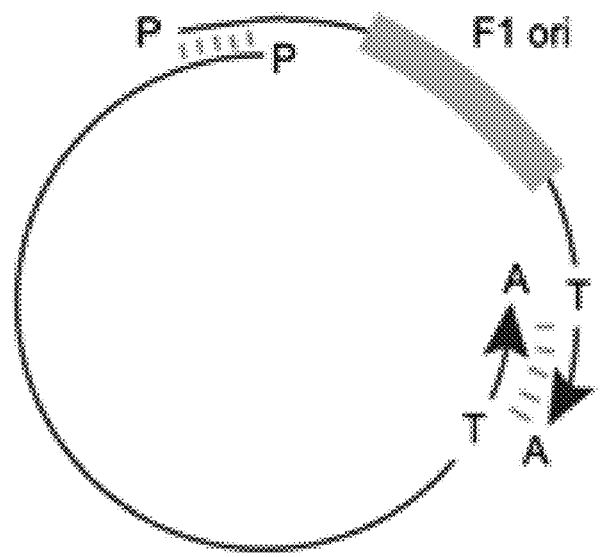
FIG. 7 is a schematic representation of de novo plasmid assembly using ssDNA components.
Figure 8A:
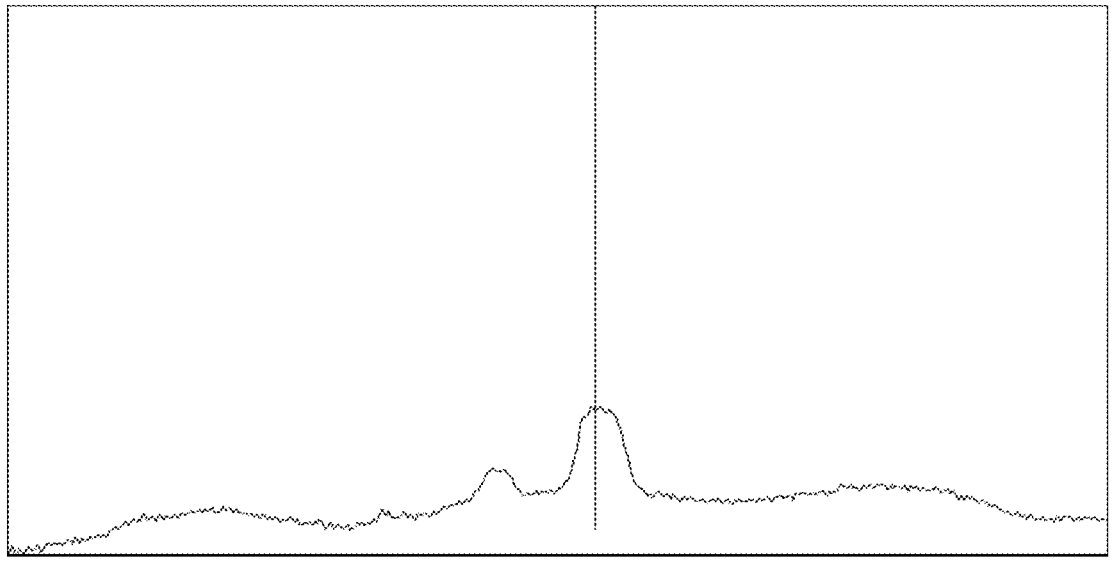
FIGS. 8A and 8B are line graphs.
Figure 8B:
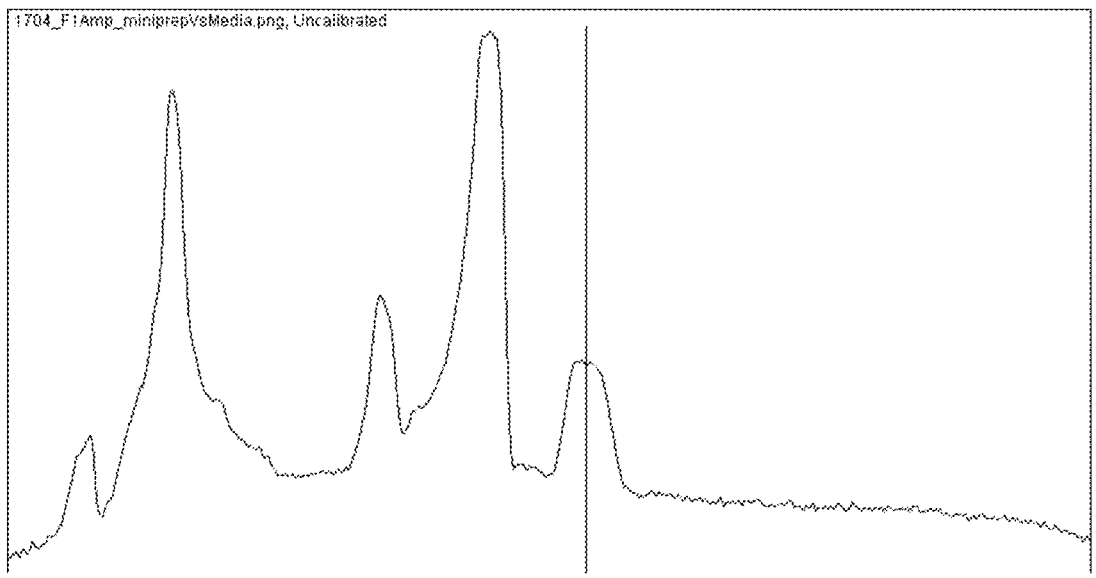
Figure 9A:
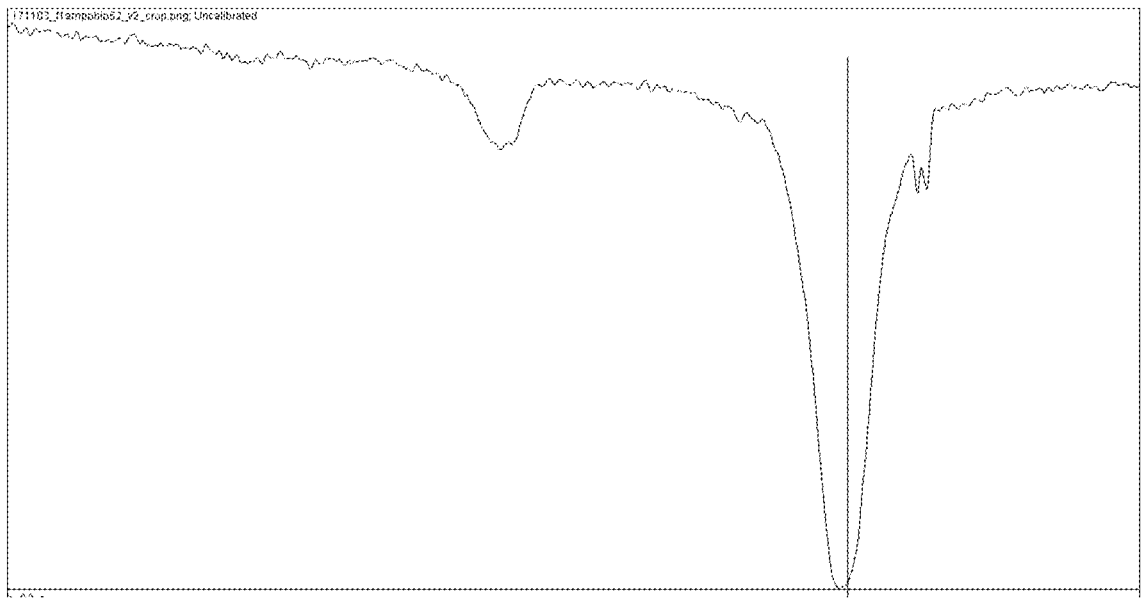
FIGS. 9A and 9B are line graphs.
Figure 9B:
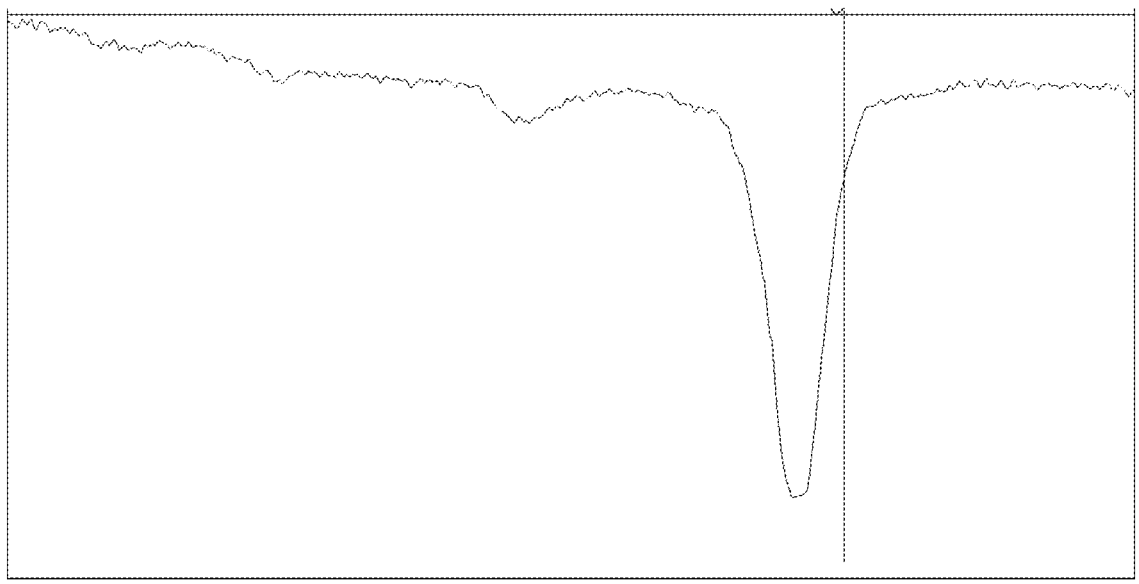

To achieve high cloning efficiency and minimal production of off-target sequences, restriction-free cloning from long ssDNA was used (FIG. 3, FIG. 7). The f1-origin sequence was synthesized and amplified with a 20-nt complementary overlap sequence to an ampicillin cistron. Megaprimer ssDNA was then produced using asymmetric PCR (aPCR) (Veneziano, et al. (2017) bioRxiv). The bottom-strand ampicillin cistron, including the 20-nt reverse complement of the overlapping sequence, was also amplified to ssDNA using aPCR. The two ssDNAs sequences were mixed at equimolar concentration and completed to dsDNA using PCR. They were then transformed into chemically competent M13cp strain E. coli, yielding several colonies of identical appearance when dual-selected by chloramphenicol and ampicillin. Colonies were selected, and sequencing and PCR identified 2 colonies of the correct sequence (pPB52).

Once the phagemid was cloned, M13cp transformed with pPB52 was grown in TB for 48 h, ensuring high yields of ssDNA in the surrounding media as phage material accumulated (Tomley, F. M. (1996) Methods Mol Biol, 58, 359-362). The bacteria were removed from the media by centrifugation and DNA was purified from both the bacterial pellet and from the clarified phage-containing media. Direct extraction from ethanol precipitation and silica column purification showed a clean ssDNA band present in both the E. coli pellet and the surrounding media. While the pellet was contaminated with both dsDNA intermediate and helper phage, the phage in the media contained only pure ssDNA.

The purified ssDNA was then used for folding of a DNA nanoparticle. The phagemid sequence was used as an input to the DAEDALUS automated design algorithm for a pentagonal bipyramid with a 52 base-pair edge length. The staples (Table 1) were added in 20 molar excess and the nanoparticle was folded in the presence of 12 mM MgCl2 using the protocol as previously described (Veneziano, R., Ratanalert, S., Zhang, K., Zhang, F., Yan, H., Chiu, W. and Bathe, M. (2016), Science, 352, 1534). Gel migration shift assays showed a clear shift in the band upon folding with high yield (FIGS. 8A, 8B, 9A, and 9B). The folded nanostructures were then purified, dried with negative stain, and visualized using transmission electron microscopy (TEM). The particles were homogeneous and monodispersed, and showed clear pentagonal signature for particles in the flat orientation.

Having shown ssDNA production from bacteria for DNA origami, this production system was used to fold DNA nanoparticles direct from phage without purification. Media saturated with phage production from E. coli M13cp was clarified by centrifugation to remove the bacteria while leaving the phage. The phage was buffer exchanged on a spin concentrator from spent broth into folding buffer. Nanoparticles were folded from either buffer exchanged phage, or from the phage media directly, with folding achieving high yield for each according to gel migration shift assays. To ensure proper folding, the phage, and crude phage material with DNA folded were imaged by TEM. Notable, the assembled phage are approximately 150 nm in length, which is consistent given the wild-type 7,000 nt M13 assembles to 900 nm phage.

Thus, the M13cp strain was applied in combined with restriction free cloning for the production of pure ssDNA direct from bacteria. This method of assembly and direct purification of phagemid ssDNA without additional dsDNA contamination allows for new technology development in ssDNA sequence production that can be made bio-orthogonal and scalable, suitable for use in therapeutic and materials applications.

Example 3: Cloning a DNA Containing Only the f1-Origin with a User-Determined Sequence Methods A nucleic acid sequence was generated by AES encryption of a line from the play "The Crucible" encoding forward paging barcodes, magic filetype barcodes, End Of File barcode, and slack space to fill to 1,100 nucleotides. Primers that overlap in sequence by 20 nucleotides at the end of the ampicillin terminator from the mini f1-Amp plasmid and a complementary primer that overlapped between the terminator and the sequence in the reverse complement orientation. The sequence was amplified with a 50-fold excess of phosphorylated reverse primer and the Amp-to-Crucible forward primer. A second single-stranded DNA was amplified by 50-fold excess of phosphorylated f1 forward primer over the Crucible-to-Amp reverse primer. aPCR was then used to generate these two 1,000-nt ssDNA primers, which were subsequently purified from agarose gel separation. The two primers were mixed in equimolar concentration at 1 ng each in 50 uL of Phusion reaction. These long primers overlapped by 20 nt which annealed at 63 C. The phosphorylated f1 forward primer and the Crucible reverse primers were additionally added to 500 nM concentration and amplified with 25 cycles. The resulting band was gel purified and ligated by T4 DNA ligase and transformed to helper strain competent cells and selected on chloramphenicol/ampicillin selection Loria-Agar plates.

Results

Four clones were tested by PCR, agarose gel visualization, and sequencing. All 4 colonies were positive for the f1-Amp-Crucible sPhage (FIG. 10).

Example 4: Paranemic Crossover DNA Nanoparticles Produced In Vivo by Bacterial Production of Specific ssDNAs DNA nanoparticles can be produced by a single strand of DNA using paranemic crossovers (PX), where each helix crosses over to an adjacent helix at every possible meeting position without disruption of the geometry of the helices. Therefore, a particle geometry such as, for example, a tetrahedron, octahedron, petagonal bipyramid, can be generated by a single strand of DNA routed around the entire structure without staples. The procedure for making a PX open wireframe particle has been automated. A sequence satisfying the ability to form a routed tetrahedron has been cloned to the f1-origin.

A sequence encoding an ssDNA that folds into a staple-free PX tetrahedron was cloned with the f1-origin of replication and the ampicillin selection cistron and transformed into M13cp *E. coli* for the biological production of PX-tetrahedron to test assembly of nanoparticles in situ. To test such a system, two phagemids were independently produced from the strain, f1-Amp alone, and f1-Amp-PXtet66. F1-Amp bacterial growth was spun down twice at 4,000 RPMs and the supernatant was taken, and concentrated on a 100 kDA molecular weight cut off filter, and buffer exchanged to 1× tris-EDTA-acetate with 12 mM MgCl2 3 times 5 fold each round. The phage was then mixed with 20-fold molar ratio of staples and folding buffer with 0.2% SDS, and brought to 100 µL and folded from 95° C. to 24° C. over 13 hours. A clear gel shift was noted to the same level as the purified ssDNA, and thus folding direct from phage is possible using this sequence (see FIGS. 11A-11D).

The DNA from the f1-Amp-PXtet66 was also purified and tested for folding both alone in the absence of staples (thus yielding a PX tetrahedron in buffer similar to the DX structures except for 16 mM $MgCl_2$ and not 12 mM, and a folding time of 21 hours and not 13 hours. This folding was additionally carried out in the presence of the pentagonal bipyramid staples specific to the f1-Amp phagemid, thus allowing for co-folding of a pentagonal bipyramid DX with a tetrahedron PX structure. Thus these plasmids allow for a wide variety of DX and PX structures to be built and characterized direct from the bacterial product. Structures made from purified ssDNA and direct from phage will be characterized by cryo electron microscopy and transmission electron microscopy.

Example 5: An Exemplary Protocol Produces Purified ssDNA

Materials and Methods
Dual-selective agar plates:
  20 mL plate
  20 mL 1×LA
  50 µg/mL Ampicillin
  15 µg/mL Chloramphenicol
Media Broth:
  31 g 2×YT powder (Sigma-Aldrich Y2377)
  1 L $H_2O$
  2 mM $MgCl_2$
  50 µg/mL Ampicillin (1:1000× concentrate in −20° C.)
  15 µg/mL Chloramphenicol (1:2000× concentrate in −20° C.)
  Sterilize by filtration or autoclave
Day 1:
  From glycerol stock stored in −80° C., under sterile conditions, streak to single colonies on a dual selective plate.
  Incubate plates over night at 37° C.
Day 2:
  Prepare pre-culture:
    Add 4 mL of Media Broth to a culture tube
    Inoculate with a single colony grown overnight on the dual-selective plate
    Shake the liquid culture at 32° C. for 16 hrs at 200 rpm
Day 3:
  Expand into larger culture:
    Add 4 mL preculture at a ratio of 1:100 to 400 mL Media Broth
    Split to 2 2 L baffled shaker flasks with 200 mL in each
    Shake the culture at 37° C. for 12-16 hrs at 200 rpm
Day 4:
  Clarify media:
    Decant culture media to conical centrifuge tubes
    Centrifuge cultures at 4,000 rpm for 20 min at 4° C.
    Pour supernatant into a fresh set of conical centrifuge tubes
    Centrifuge a second time at 4,000 rpm for 20 min at 4° C.
    Centrifuge 3 mL of original growth and keep the bacterial pellet for processing total DNA
    Carefully decant the clarified media (containing phage) to a fresh container for further purification
  Filtration:
    Filter supernatant through 0.45 µm cellulose acetate filter (vacuum filter for large volumes)
  Concentration: (use Amicon Ultra Centrifugal Filter Ultracel 100K)
    Prewash centrifuge filter using 15 mL PBS
    Centrifuge at 4,000 rpm for 10 min at room temperature
    Discard both flow through and any PBS retained in the upper chamber
    Pour 15 mL filtered supernatant into upper chamber
    Centrifuge at 3,000 rpm for 20 min at room temperature
    Discard flow through, refill the upper chamber to 15 mL
    Centrifuge at 3,000 rpm for 20 min at room temperature
    Repeat until all of the supernatant has been processed
    Pour retained supernatant into a fresh 50 mL conical tube for DNA extraction
  DNA extraction:
    To the retained phage, add SDS to 0.02% w/v final concentration
    Incubate at 70° C. for 15 min
    Put the culture on ice
    Add 0.1 volumes of 3 M sodium acetate pH 5.2 (300 mM final concentration)
    Add 2.5 volumes ice-cold 100% ethanol
    Incubate at −20° C. overnight
    Centrifuge at 14,000 rpm for 30 min at 4° C. to pellet precipitated DNA
    Toss out supernatant, resuspend pellet in 2 mL Qiagen buffer P1
    Add 40 µg/mL RNase A/T1 and 200 µg/mL Proteinase K
    Incubate at 37 C for 1-2 hrs
    Add 2 mL buffer P2, incubate at 80° C. for 10 min
    Follow the rest of the Miraprep protocol using a Qiagen silica column purification (Pronobis, et al., PLoS ONE 11(8): e0160509. doi: 10.1371/journal.pone.0160509 (2016))
    Elute in 50 µL nuclease-free water
    Determine DNA concentration by UV260 absorption (Nanodrop)
    Run 200 ng of DNA sample on a 1% agarose gel stained with SybrSafe, 90V for 60 min.
Time course assay protocol:
  Prepare 4 mL pre-culture:
    TB with glycerol or 2×YT broth (Sigma-Aldrich Y2377)
    2 mM $MgCl_2$ 50 µg/mL ampicillin
15 µg/mL chloramphenicol
Inoculate the 4 mL media with a single colony from the selective plate
Incubate at 32° C. for 16 hrs at 200 rpm
Expand into larger culture:
　Add 4 mL preculture at a ratio of 1:100 to TB or 2×YT broth containing 2 mM MgCl$_2$, 50 µg/mL ampicillin and 15 µg/mL chloramphenicol (400 mL final)
　Split to incubate 200 mL at 37° C. for 24 hrs at 200 rpm in a baffled 2 liter shaker flask
Sampling time points:
　Extract 5 mL from each culture
　Measure OD600 with 1 mL, diluted with original media as necessary to achieve absorbance less than 0
　Spin down remaining 4 mL at 4000 rpm for 10 min at 4° C.
　Pour supernatant into fresh tubes, then spin down again with same conditions
Filtration:
　Filter supernatant through 0.45 µm cellulose acetate filter
DNA extraction:
　Split samples into two sets, set aside one set (no additional treatment)
　Treat other set with 40 µg/mL RNase A/T1 and 200 µg/mL
　Proteinase K
　Incubate for 1 hour at 37° C.
　Add 2 mL buffer P2, incubate at 80° C. for 10 min
　Follow the rest of the Miraprep protocol (Pronobis, et al., PLoS ONE 11(8):e0160509. doi:10.1371/journal.pone.0160509 (2016))
　Elute in 50 µL nuclease-free water
　Nanodrop
　Run on 1% agarose gel at 90V for 60 min to check bands
　Perform gel densitometry using FIJI image processing software
Results Intensity is determined via gel densitometry and corresponds to the amount of ssDNA produced at that time point, whereas OD600 is an estimate of the concentration of bacteria in culture at that time point. The Intensity/OD600 at each time point therefore is a metric for the amount of target ssDNA produced with respect to the bacterial biomass. The 2×YT culture did not reach the same OD600 as the TB culture because both grown over a 24 hour period and bacteria proliferate more slowly in 2×YT. However, with the available data points, it is still clear that 2×YT media allows for higher production of the target ssDNA than TB media. Additionally, the gel images of the DNA extracted from the TB and 2×YT cultures show that there is less contamination from dsDNA and bacterial genomic DNA in 2×YT cultures than in TB cultures. Based on these results, it was concluded that better yields of the target ssDNA can be achieved using 2×YT media than TB media. Individual plots for each media type and DNA extraction protocol are shown below.

Unless defined otherwise, all technical and scientific terms used have the same meanings as commonly understood by one of skill in the art to which the disclosed invention belongs. Publications cited and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An nucleic acid comprising or encoding
   (i) a bacteriophage origin of replication as the only origin of replication,
   (ii) a bacteriophage packaging signal,
   (iii) a target single-strand DNA (ssDNA) sequence of interest heterologous to the bacteriophage origin of replication, and
   (iv) a selectable marker,
   wherein the nucleic acid does not comprise or encode a virus's genome.

2. The nucleic acid of claim 1, wherein (iii) and (iv) are different nucleic acid sequences.

3. The nucleic acid of claim 2, wherein the nucleic acid does not encode bacteriophage proteins.

4. The nucleic acid of claim 1, wherein the nucleic acid is single stranded.

5. The nucleic acid of claim 4, wherein the nucleic acid is circular.

6. The nucleic acid of claim 4, wherein the nucleic acid is linear.

7. The nucleic acid of claim 1, wherein the nucleic acid is double stranded.

8. The nucleic acid of claim 1, wherein the nucleic acid is circular and double stranded.

9. The nucleic acid of claim 1, wherein the nucleic acid is circular and single stranded.

10. The nucleic acid of claim 1, wherein the target ssDNA sequence of interest is a scaffold sequence that can form a 2D or 3D DNA origami structure.

11. The nucleic acid of claim 1, wherein the target ssDNA sequence of interest encodes bitstream data.

12. The nucleic acid of claim 1, wherein the heterologous target single-strand DNA (ssDNA) sequence of interest comprises a bait or capture sequence that can anneal or bind a single-guide- or crispr-RNAs (crRNA), anti-sense DNA, anti-sense RNA, a DNA coding for therapeutic or non-therapeutic proteins, mRNA, miRNA, piRNA, siRNA, or DNA-interacting protein.

13. The nucleic acid of claim 1 comprising or encoding the nucleic acid sequence of SEQ ID NO: 1 or a variant thereof with at least 75% sequence identity to SEQ ID NO: 1, wherein SEQ ID NO: 1 encodes (i), (ii), and (iv).

14. The nucleic acid of claim 1 comprising or encoding the nucleic acid sequence of SEQ ID NO: 4 without nucleic acids 469-1555, or a variant thereof with at least 75% sequence identity to SEQ ID NO: 4, wherein SEQ ID NO: 4 encodes (i) and (ii) and (ii).

15. The nucleic acid of claim 1 comprising or encoding the nucleic acid sequence of SEQ ID NO: 5 without nucleic acids 1683-2769, or a variant thereof with at least 75% sequence identity to SEQ ID NO: 5, wherein SEQ ID NO: 5 encodes (i), (ii), and (iv).

16. The nucleic acid of claim 1 comprising or encoding the nucleic acid sequence of SEQ ID NO: 6 without nucleic acids 1683- 2514, or a variant thereof with at least 75% sequence identity to SEQ ID NO: 6, wherein SEQ ID NO: 6 encodes (i), (ii), and (iv).

17. The nucleic acid of claim 1 comprising or encoding the nucleic acid sequence of SEQ ID NO: 7 without nucleic acids 1683-3229, or a variant thereof with at least 75% sequence identity to SEQ ID NO: 7, wherein SEQ ID NO: 7 encodes (i), (ii), and (iv).

18. A host cell comprising the nucleic acid of claim 1.

19. The host cell of claim 18, further comprising a double stranded nucleic acid helper plasmid, wherein the helper plasmid encodes one or more bacteriophage factors capable of packaging a single strand of the nucleic acid into a bacteriophage particle, and wherein the helper plasmid lacks a packaging signal.

20. The host cell of claim 19 wherein the helper plasmid, or a second plasmid, encodes one or more additional functional elements that can be incorporated into or onto the target ssDNA of interest.

21. The host cell of claim 20 wherein the one or more functional elements are selected from the group consisting of single-guide- or crispr-RNAs (crRNA), anti-sense DNA, anti-sense RNA, one or more proteins, or a combination thereof.

22. The host cell of claim 21, wherein the functional elements comprise single-guide- or crispr-RNAs (crRNA) alone or in combination with a Cas protein.

23. The host cell of claim 18
   wherein the host cell comprises a disrupted lipopolysaccharide pathway,
   the host cell lacks a functional RNase H gene (rnh),
   or a combination thereof.

24. The host cell of claim 18, wherein the target ssDNA sequence of interest is a scaffold sequence that can form a 2D or 3D DNA origami structure, and
   wherein the host cell expresses one or more staple strand nucleic acids that facilitate folding of the ssDNA into a 2D or 3D DNA origami structure.

25. The host cell of claim 18, further comprising a plasmid comprising the nucleic acid sequence of SEQ ID NO:8, or a variant thereof with at least 75%, 80%, 85%, 90%, or 95% sequence identity to SEQ ID NO:8.

26. A microorganism that produces pure single stranded nucleic acid of a user-defined length and sequence, the microorganism comprising
   (a) the nucleic acid of claim 1,
   and
   (b) a double stranded nucleic acid helper plasmid,
   wherein the helper plasmid comprises genes of the corresponding phage and optionally lacks the phage packaging signal.

27. A method for the in vivo production of a single-stranded nucleic acid comprising
   culturing in growth medium a microorganism transfected with the nucleic acid of claim 1 and a medium copy number helper plasmid comprising a nucleic acid sequence encoding phage proteins and absent a phage packaging signal under conditions sufficient to generate a plurality of the target ssDNA and optionally package the ssDNA into bacteriophage particles.

28. The method of claim 27, further comprising isolating the target ssDNA from the microorganism, the bacteriophage particles, or the growth medium.

\* \* \* \* \*

SEQUENCE LISTING

```
<160> NUMBER OF SEQ ID NOS: 64

<210> SEQ ID NO 1
<211> LENGTH: 1676
<212> TYPE: DNA
<213> ORGANISM: Artificial Sequence
<220> FEATURE:
<223> OTHER INFORMATION: synthetic polynucleotide

<400> SEQUENCE: 1
gagcgcaacg caattaatgt gcgccctgta gcggcgcatt aagcgcggcg ggtgtggtgg      60
ttacgcgcag cgtgaccgct acacttgcca gcgccctagc gcccgctcct ttcgctttct     120
tcccttcctt tctcgccacg ttcgccggct ttccccgtca agctctaaat cggggggctcc    180 ctttagggtt ccgatttagt gctttacggc acctcgaccc caaaaaactt gattagggtg     240
atggttcacg tagtgggcca tcgccctgat agacggtttt tcgccctttg acgttggagt     300
ccacgttctt taatagtgga ctcttgttcc aaactggaac aacactcaac cctatctcgg     360
tctattcttt tgatttataa gggattttgc cgatttcggc ctattggtta aaaaatgagc     420
tgatttaaca aaaatttaac gcgaattaca accggggtac atatgattgg ggtctgacgc     480
tcagtggaac gaaaactcac gttaagggat tttggtcatg agattatcaa aaaggatctt     540
cacctagatc cttttaaatt aaaaatgaag ttttaaatca atctaaagta tatatgagta     600
aacttggtct gacagttacc aatgcttaat cagtgaggca cctatctcag cgatctgtct     660
```

```
atttcgttca tccatagttg cctgactccc cgtcgtgtag ataactacga tacgggaggg      720
cttaccatct ggccccagtg ctgcaatgat accgcgagac ccacgctcac cggctccaga      780
tttatcagca ataaaccagc cagccggaag ggccgagcgc agaagtggtc ctgcaacttt      840
atccgcctcc atccagtcta ttaattgttg ccgggaagct agagtaagta gttcgccagt      900
taatagtttg cgcaacgttg ttgccattgc tacaggcatc gtggtgtcac gctcgtcgtt      960
tggtatggct tcattcagct ccggttccca acgatcaagg cgagttacat gatccccat     1020 gttgtgcaaa aaagcggtta gctccttcgg tcctccgatc gttgtcagaa gtaagttggc     1080
cgcagtgtta tcactcatgg ttatggcagc actgcataat tctcttactg tcatgccatc     1140
cgtaagatgc ttttctgtga ctggtgagta ctcaaccaag tcattctgag aatagtgtat     1200
gcggcgaccg agttgctctt gcccggcgtc aataccggga ataccgcgc cacatagcag     1260 aactttaaaa gtgctcatca ttggaaaacg ttcttcgggg cgaaaactct caaggatctt     1320
accgctgttg agatccagtt cgatgtaacc cactcgtgca cccaactgat cttcagcatc     1380
ttttactttc accagcgttt ctgggtgagc aaaaacagga aggcaaaatg ccgcaaaaaa     1440
gggaataagg gcgacacgga aatgttgaat actcatactc ttcctttttc aatattattg     1500
aagcatttat cagggttatt gtctcatgag cggatacata tttgaatgta tttagaaaaa     1560
taaacaaata ggggttccgc gcacatttcc ccgaaaagtg ccacctgacg tctaagaaac     1620
cattattatc atgacattaa cctataaaaa taggcgtatc acgaggccct ttcgtc        1676
```

<210> SEQ ID NO 2
<211> LENGTH: 1152
<212> TYPE: DNA
<213> ORGANISM: Artificial Sequence
<220> FEATURE:
<223> OTHER INFORMATION: synthetic polynucleotide

<400> SEQUENCE: 2

```
acaaccgggg tacatatgat tgggtctga cgctcagtgg aacgaaaact cacgttaagg        60 gatttggtc atgagattat caaaaggat cttcacctag atccttttaa attaaaaatg       120
aagttttaaa tcaatctaaa gtatatatga gtaaacttgg tctgacagtt accaatgctt       180
aatcagtgag gcacctatct cagcgatctg tctatttcgt tcatccatag ttgcctgact       240
ccccgtcgtg tagataacta cgatacggga gggcttacca tctggcccca gtgctgcaat       300
gataccgcga gacccacgct caccggctcc agatttatca gcaataaacc agccagccgg       360
aagggccgag cgcagaagtg gtcctgcaac tttatccgcc tccatccagt ctattaattg       420
ttgccgggaa gctagagtaa gtagttcgcc agttaatagt ttgcgcaacg ttgttgccat       480
tgctacaggc atcgtggtgt cacgctcgtc gtttggtatg gcttcattca gctccggttc       540
ccaacgatca aggcgagtta catgatcccc catgttgtgc aaaaaagcgg ttagctcctt       600
cggtcctccg atcgttgtca gaagtaagtt ggccgcagtg ttatcactca tggttatggc       660
agcactgcat aattctctta ctgtcatgcc atccgtaaga tgcttttctg tgactggtga       720
gtactcaacc aagtcattct gagaatagtg tatgcggcga ccgagttgct cttgcccggc       780
gtcaatacgg gataataccg cgccacatag cagaacttta aaagtgctca tcattggaaa       840
acgttcttcg gggcgaaaac tctcaaggat cttaccgctg ttgagatcca gttcgatgta       900
acccactcgt gcacccaact gatcttcagc atcttttact ttcaccagcg tttctgggtg       960
agcaaaaaca ggaaggcaaa atgccgcaaa aagggaata agggcgacac ggaaatgttg      1020
aatactcata ctcttccttt tcaatatta ttgaagcatt tatcagggtt attgtctcat      1080
```

```
gagcggatac atatttgaat gtatttagaa aaataaacaa ataggggttc cgcggagcgc    1140
aacgcaatta at                                                       1152

<210> SEQ ID NO 3
<211> LENGTH: 468
<212> TYPE: DNA
<213> ORGANISM: Artificial Sequence
<220> FEATURE:
<223> OTHER INFORMATION: synthetic polynucleotide

<400> SEQUENCE: 3
gagcgcaacg caattaatgt gcgccctgta gcggcgcatt aagcgcggcg ggtgtggtgg      60
ttacgcgcag cgtgaccgct acacttgcca gcgccctagc gcccgctcct ttcgctttct     120
tcccttcctt tctcgccacg ttcgccggct tccccgtca agctctaaat cggggggctcc    180 ctttagggtt ccgatttagt gctttacggc acctcgaccc caaaaaactt gattagggtg     240
atggttcacg tagtgggcca tcgccctgat agacggtttt tcgccctttg acgttggagt     300
ccacgttctt taatagtgga ctcttgttcc aaactggaac aacactcaac cctatctcgg     360
tctattcttt tgatttataa gggattttgc cgatttcggc ctattggtta aaaaatgagc     420
tgatttaaca aaaatttaac gcgaattaca accggggtac atatgatt                468

<210> SEQ ID NO 4
<211> LENGTH: 1555
<212> TYPE: DNA
<213> ORGANISM: Artificial Sequence
<220> FEATURE:
<223> OTHER INFORMATION: synthetic polynucleotide

<400> SEQUENCE: 4
gagcgcaacg caattaatgt gcgccctgta gcggcgcatt aagcgcggcg ggtgtggtgg      60
ttacgcgcag cgtgaccgct acacttgcca gcgccctagc gcccgctcct ttcgctttct     120
tcccttcctt tctcgccacg ttcgccggct tccccgtca agctctaaat cggggggctcc    180 ctttagggtt ccgatttagt gctttacggc acctcgaccc caaaaaactt gattagggtg     240
atggttcacg tagtgggcca tcgccctgat agacggtttt tcgccctttg acgttggagt     300
ccacgttctt taatagtgga ctcttgttcc aaactggaac aacactcaac cctatctcgg     360
tctattcttt tgatttataa gggattttgc cgatttcggc ctattggtta aaaaatgagc     420
tgatttaaca aaaatttaac gcgaattaca accggggtac atatgattgt cgtcgtcccc    480
tcaaactctt gggtggagag gctattcgtt taaggtcaca tcgcatgtaa tttacttatt    540
ctctgttgtt gagccacccg ggcgccagat tttgtttaaa gctttgtctc ttagtttgta    600
tagacagatt cagagtgcaa ggtttcgttc gctcgtacct ggttttccct ggttcttcac    660
agataggatt tgactttcta caacacttat gcggcttcct acccgtttga aggccgatac    720
aggtgctgcg caaaatgcgg gcgaacatag agtatcaaaa caacgccttc taatctagga    780
atatagggaa gatacgtatt tgctaccatg ctttctgggg tcattaacga ccaacctctt    840
ttcttttaaa gtaggattgc acaatgaatg aatacacgtg gtccgataac tgaccaagta    900
acatggttat cactcgatgt ccgccagacg tgtgcaaacc aacccgggag ttacgtcact    960
aatccttcgc tacgtcgtga agatatttac ttgtgaatat cgagggtaat aagataatag   1020
actgtgacta gtattgccag actgtcgcta cctgcaacac ataactatcc tgaggttact   1080
gcatagtact gattacaccc gagtcaaaat ttctaacttc taacatgtac ctagtaacca   1140
```

```
gctcaataat tatgtcagaa tatagctctg ggaaccctcg acaattatg atacacggta    1200 ttaatatctt gcttgcgtta gccacttctc atctttggat accgattcta ttttgcatag   1260
cagttccttt tacacatata agaatttcgc cataggtatg acctacccca gatcgtcgat   1320
tatctgctgg aaaatttatt taacactatg tttctctcca gatgtgagta tacacgataa   1380
ataatacctg ggtaccggtt ggtgttatta ccttgtttct aagtgcttaa tcggcgctta   1440
gtgataaggt tgtactagtc gacgcgtggc cgccaattat tcttgtcata atttgacttt   1500
gttctatatg actatgatct cctgtcatct cacctattga tgccacctttt tcagc        1555
```

<210> SEQ ID NO 5
<211> LENGTH: 2775
<212> TYPE: DNA
<213> ORGANISM: Artificial Sequence
<220> FEATURE:
<223> OTHER INFORMATION: synthetic polynucleotide

<400> SEQUENCE: 5

```
gagcgcaacg caattaatgt gcgccctgta gcggcgcatt aagcgcggcg ggtgtggtgg     60
ttacgcgcag cgtgaccgct acacttgcca gcgccctagc gcccgctcct ttcgctttct    120
tcccttcctt tctcgccacg ttcgccggct ttccccgtca gctctaaat cggggggctcc    180 ctttagggtt ccgatttagt gctttacggc acctcgaccc caaaaaactt gattagggtg    240
atggttcacg tagtgggcca tcgccctgat agacggtttt tcgccctttg acgttggagt    300
ccacgttctt taatagtgga ctcttgttcc aaactggaac aacactcaac cctatctcgg    360
tctattcttt tgatttataa gggattttgc cgatttcggc ctattggtta aaaaatgagc    420
tgatttaaca aaaatttaac gcgaattaca accggggtac atatgattgg ggtctgacgc    480
tcagtggaac gaaaactcac gttaagggat tttggtcatg agattatcaa aaaggatctt    540
cacctagatc cttttaaatt aaaaatgaag ttttaaatca atctaaagta tatatgagta    600
aacttggtct gacagttacc aatgcttaat cagtgaggca cctatctcag cgatctgtct    660
atttcgttca tccatagttg cctgactccc cgtcgtgtag ataactacga tacggagggg    720
cttaccatct ggccccagtg ctgcaatgat accgcgagac ccacgctcac cggctccaga    780
tttatcagca ataaaccagc cagccggaag ggccgagcgc agaagtggtc ctgcaacttt    840
atccgcctcc atccagtcta ttaattgttg ccgggaagct agagtaagta gttcgccagt    900
taatagtttg cgcaacgttg ttgccattgc tacaggcatc gtggtgtcac gctcgtcgtt    960
tggtatggct tcattcagct ccggttccca acgatcaagg cgagttacat gatcccccat   1020
gttgtgcaaa aaagcggtta gctccttcgg tcctccgatc gttgtcagaa gtaagttggc   1080
cgcagtgtta tcactcatgg ttatggcagc actgcataat tctcttactg tcatgccatc   1140
cgtaagatgc ttttctgtga ctggtgagta ctcaaccaag tcattctgag aatagtgtat   1200
gcggcgaccg agttgctctt gcccggcgtc aatacgggat aataccgcgc cacatagcag   1260
aactttaaaa gtgctcatca ttggaaaacg ttcttcgggg cgaaaactct caaggatctt   1320
accgctgttg agatccagtt cgatgtaacc cactcgtgca cccaactgat cttcagcatc   1380
ttttactttc accagcgttt ctgggtgagc aaaaacagga aggcaaaatg ccgcaaaaaa   1440
gggaataagg gcgacacgga aatgttgaat actcatactc ttcctttttc aatattattg   1500
aagcatttat cagggttatt gtctcatgag cggatacata tttgaatgta tttagaaaaa   1560
taaacaaata ggggttccgc gcacatttcc ccgaaaagtg ccacctgacg tctaagaaac   1620
cattattatc atgacattaa cctataaaaa taggcgtatc acgaggccct ttcgtcgaat   1680
```

```
tcgtcgtcgt cccctcaaac tcttgggtgg agaggctatt cgtttaaggt cacatcgcat      1740
gtaatttact tattctctgt tgttgagcca cccgggcgcc agattttgtt taaagctttg      1800
tctcttagtt tgtatagaca gattcagagt gcaaggtttc gttcgctcgt acctggtttt      1860
ccctggttct tcacagatag gatttgactt tctacaacac ttatgcggct tcctacccgt      1920
ttgaaggccg atacaggtgc tgcgcaaaat gcgggcgaac atagagtatc aaaacaacgc      1980
cttctaatct aggaatatag ggaagatacg tatttgctac catgctttct ggggtcatta      2040
acgaccaacc tcttttcttt taaagtagga ttgcacaatg aatgaataca cgtggtccga      2100
taactgacca agtaacatgg ttatcactcg atgtccgcca gacgtgtgca aaccaacccg      2160
ggagttacgt cactaatcct tcgctacgtc gtgaagatat ttacttgtga atatcgaggg      2220
taataagata atagactgtg actagtattg ccagactgtc gctacctgca acacataact      2280
atcctgaggt tactgcatag tactgattac acccgagtca aaatttctaa cttctaacat      2340
gtacctagta accagctcaa taattatgtc agaatatagc tctgggaacc ctcggacaat      2400
tatgatacac ggtattaata tcttgcttgc gttagccact tctcatcttt ggataccgat      2460
tctattttgc atagcagttc cttttacaca tataagaatt cgccatagg tatgacctac       2520
cccagatcgt cgattatctg ctggaaaatt tatttaacac tatgtttctc tccagatgtg      2580
agtatacacg ataaataata cctgggtacc ggttggtgtt attccttgt ttctaagtgc       2640
ttaatcggcg cttagtgata aggttgtact agtcgacgcg tggccgccaa ttattcttgt      2700
cataatttga ctttgttcta tatgactatg atctcctgtc atctcaccta ttgatgccac      2760
cttttcagcc tgcag                                                       2775
```

<210> SEQ ID NO 6
<211> LENGTH: 2520
<212> TYPE: DNA
<213> ORGANISM: Artificial Sequence
<220> FEATURE:
<223> OTHER INFORMATION: synthetic polynucleotide

<400> SEQUENCE: 6

```
gagcgcaacg caattaatgt gcgccctgta gcggcgcatt aagcgcggcg ggtgtggtgg        60
ttacgcgcag cgtgaccgct acacttgcca gcgccctagc gcccgctcct ttcgctttct       120
tcccttcctt tctcgccacg ttcgccggct tccccgtca agctctaaat cggggggctcc      180
ctttagggtt ccgatttagt gctttacggc acctcgaccc caaaaaactt gattagggtg       240
atggttcacg tagtgggcca tcgccctgat agacggtttt tcgccctttg acgttggagt       300
ccacgttctt taatagtgga ctcttgttcc aaactggaac aacactcaac cctatctcgg       360
tctattcttt tgatttataa gggattttgc cgatttcggc ctattggtta aaaatgagc        420
tgatttaaca aaaatttaac gcgaattaca accggggtac atatgattgg ggtctgacgc       480
tcagtggaac gaaaactcac gttaagggat tttggtcatg agattatcaa aaaggatctt       540
cacctagatc cttttaaatt aaaaatgaag ttttaaatca atctaaagta tatatgagta       600
aacttggtct gacagttacc aatgcttaat cagtgaggca cctatctcag cgatctgtct       660
atttcgttca tccatagttg cctgactccc cgtcgtgtag ataactacga tacgggaggg      720
cttaccatct ggccccagtg ctgcaatgat accgcgagac ccacgctcac cggctccaga       780
tttatcagca ataaaccagc cagccggaag ggccgagcgc ataagtggtc ctgcaacttt       840
atccgcctcc atccagtcta ttaattgttg ccgggaagct agagtaagta gttcgccagt       900
```

```
taatagtttg cgcaacgttg ttgccattgc tacaggcatc gtggtgtcac gctcgtcgtt    960
tggtatggct tcattcagct ccggttccca acgatcaagg cgagttacat gatcccccat   1020
gttgtgcaaa aaagcggtta gctccttcgg tcctccgatc gttgtcagaa gtaagttggc   1080
cgcagtgtta tcactcatgg ttatggcagc actgcataat tctcttactg tcatgccatc   1140
cgtaagatgc ttttctgtga ctggtgagta ctcaaccaag tcattctgag aatagtgtat   1200
gcggcgaccg agttgctctt gcccggcgtc aatacgggat aataccgcgc cacatagcag   1260
aactttaaaa gtgctcatca ttggaaaacg ttcttcgggg cgaaaactct caaggatctt   1320
accgctgttg agatccagtt cgatgtaacc cactcgtgca cccaactgat cttcagcatc   1380
ttttactttc accagcgttt ctgggtgagc aaaaacagga aggcaaaatg ccgcaaaaaa   1440
gggaataagg cgacacggaa atgttgaat actcatactc ttccttttc aatattattg     1500
aagcatttat cagggttatt gtctcatgag cggatacata tttgaatgta tttagaaaaa   1560
taaacaaata ggggttccgc gcacatttcc ccgaaaagtg ccacctgacg tctaagaaac   1620
cattattatc atgacattaa cctataaaaa taggcgtatc acgaggccct ttcgtcgaat   1680
tcgtcgtcgt cccctcaaac tcttgggtgg agaggctatt cgtttaaggt cacatcgcat   1740
gtaatttact tattctctgt tgttgagcca cccgggcgcc agattttgtt taaagctttg   1800
tctcttagtt tgtatagaca gattcagagt gcaaggtttc gttcgctcgt acctggtttt   1860
ccctggttct tcacagatag gatttgactt tctacaacac ttatgcggct tcctacccgt   1920
ttgaaggccg atacaggtgc tgcgcaaaat gcgggcgaac atagagtatc aaaacaacgc   1980
cttctaatct aggaatatag ggaagatacg tatttgctac catgctttct tgggtcatta   2040
acgaccaacc tcttttctt taaagtagga ttgcacaatg aatgaataca cgtggtccga    2100
taactgacca agtaacatgg ttatcactag atgtccgcca gacgtgtgca aaccaacccg   2160
ggagttacgt cactaatcct tcgctacgtc gtgaagatat ttacttgtga atatcgaggg   2220
taataagata atagactgtg actagtattg ccagactgtc gctacctgca acacataact   2280
atcctgaggt tactgcatag tactgattac acccgagtca aaatttctaa cttctaacat   2340
gtacctagta accagctcaa taattatgtc agaatatagc tctgggaacc ctcggacaat   2400
tatgatacac ggtattaata tcttgcttgc gttagccact tctcatcttt ggataccgat   2460
tctattttgc atagcagttc cttttacaca tataagaatt tcgccatagg tatgctgcag   2520
```

<210> SEQ ID NO 7
<211> LENGTH: 3229
<212> TYPE: DNA
<213> ORGANISM: Artificial Sequence
<220> FEATURE:
<223> OTHER INFORMATION: synthetic polynucleotide

<400> SEQUENCE: 7

```
gagcgcaacg caattaatgt gcgccctgta gcggcgcatt aagcgcggcg ggtgtggtgg     60
ttacgcgcag cgtgaccgct acacttgcca gcgccctagc gcccgctcct ttcgctttct   120
tcccttcctt tctcgccacg ttcgccggct ttccccgtca agctctaaat cggggggctcc   180
ctttagggtt ccgatttagt gctttacggc acctcgaccc caaaaaactt gattagggtg   240
atggttcacg tagtgggcca tcgccctgat agacggtttt tcgccctttg acgttggagt   300
ccacgttctt taatagtgga ctcttgttcc aaactggaac aacactcaac cctatctcgg   360
tctattcttt tgatttataa gggattttgc cgatttcggc ctattggtta aaaaatgagc   420
tgatttaaca aaaatttaac gcgaattaca accgggtac atatgattgg ggtctgacgc     480
```

```
tcagtggaac gaaaactcac gttaagggat tttggtcatg agattatcaa aaaggatctt    540
cacctagatc cttttaaatt aaaaatgaag ttttaaatca atctaaagta tatatgagta    600
aacttggtct gacagttacc aatgcttaat cagtgaggca cctatctcag cgatctgtct    660
atttcgttca tccatagttg cctgactccc cgtcgtgtag ataactacga tacgggaggg    720
cttaccatct ggccccagtg ctgcaatgat accgcgagac ccacgctcac cggctccaga    780
tttatcagca ataaaccagc cagccggaag ggccgagcgc ataagtggtc ctgcaacttt    840
atccgcctcc atccagtcta ttaattgttg ccgggaagct agagtaagta gttcgccagt    900
taatagtttg cgcaacgttg ttgccattgc tacaggcatc gtggtgtcac gctcgtcgtt    960
tggtatggct tcattcagct ccggttccca acgatcaagg cgagttacat gatccccat    1020 gttgtgcaaa aaagcggtta gctccttcgg tcctccgatc gttgtcagaa gtaagttggc   1080
cgcagtgtta tcactcatgg ttatggcagc actgcataat tctcttactg tcatgccatc   1140
cgtaagatgc ttttctgtga ctggtgagta ctcaaccaag tcattctgag aatagtgtat   1200
gcggcgaccg agttgctctt gcccggcgtc aatacgggat aataccgcgc cacatagcag   1260
aactttaaaa gtgctcatca ttggaaaacg ttcttcgggg cgaaaactct caaggatctt   1320
accgctgttg agatccagtt cgatgtaacc cactcgtgca cccaactgat cttcagcatc   1380
ttttactttc accagcgttt ctgggtgagc aaaaacagga aggcaaaatg ccgcaaaaaa   1440
gggaataagg gcgacacgga aatgttgaat actcatactc ttcctttttc aatattattg   1500
aagcatttat cagggttatt gtctcatgag cggatacata tttgaatgta tttagaaaaa   1560
taaacaaata ggggttccgc gcacatttcc ccgaaaagtg ccacctgacg tctaagaaac   1620
cattattatc atgacattaa cctataaaaa taggcgtatc acgaggccct tcgtcgaat    1680 tcggtctcgc tggtgaaaag aaaggcgcgc cacagggcaa tatcttacaa ttcaatcgag   1740
ccattaccac gaggggtcag ttttctgacc cccacttgta atgtacacgt tgaagctact   1800
gatatcttaa agtggctcgc tcgtcgaacg agcgtgctgc gtcttgatttt tgcgaataac   1860 ccgcaaataa accgtaaata tagtgtaaga gcccttggcg tatgtgtggc tcgaggaagc   1920
tcaacccgga tgcgaaactc aggaagaagg cttttgccca gagcctgagt ccatcatccg   1980
tccttagctt cggcccgcca cagctgcgcc aagggttcac aagtagcgta ttgtacggtg   2040
tcatacctca ccttttaggg gtgcggtcct cctgcttttg catctacgac cgctgggata   2100
aaggtgtcgt atgacattat acaatattgt ccttgtgaac tcttacacta taatattcgt   2160
ttacggctcg gttagtgaca aaatccgggt gcagcatgtt tttacaaact gcacccgcca   2220
tttgtcactc ctagagccgt acgggaatat ttcccgtctt ttgacgggaa tttacgccgt   2280
atttgcgtag gattcgcaaa tggaagacgc agttcgctcg ttcgatcttt cggggggtatc   2340 tccgtacact ctcaccaggt ccctagctga atgggtcatg gcgcatccga tcctgagagg   2400
aaggttaaga ccccaccggg tgaggcacgt aaccgttgca atcgctatga ttttcagac    2460 aaattgcaat aattacgtgc gacacccggt tcccacttaa cgtagatctc aggatgttta   2520
aaattaccgc ccgtgataga cagagccaaa tttctgacac gggcctcccc gtcagttttt   2580
acttcactgg aggcataggt cagaagtgcc gctctggtct tcacgggcgt aaatttaaa    2640 ccggatgcgc catgccgctt tcagcagaag tcctggtaaa cttgtacctc ctcaccccct   2700
cttttgagac gaggaggagt atagagttta gcggcacttc taatacaagc ggttcggccc   2760 tttgggccg aaacccatgt atttagggag ccgctgagag ctataggaga tctcgtcgaa   2820
```

```
agatcgacga gcgagcgcgt ttaaggcccc agtagcattt gcgtgtaaag ctcaagtgaa    2880
aggagaggat agctttccgg acggcaggct ccgtgggagg gatttgtagt gctctattct    2940
gttcggtacc tttttaggtt acgaacagaa agacgcacta ggcacccctc ccctatagcc    3000
tgagtgacgg aaagctacta ggctttctta gcatgtttcg aagcacggtt gccccgactc    3060
gaacggtcca tactaatttt ttagcagcga ccgtgggcct cggggaagga gtgcttatgg    3120
acatgctctc tgagcctagt atatcctctc cttttcgtgg agcttgctcg acaaatttgt    3180
aaggggctgc cctcgcgcgc gccctaccct ctccggcatt aatctgcag                3229

<210> SEQ ID NO 8
<211> LENGTH: 12548
<212> TYPE: DNA
<213> ORGANISM: Artificial Sequence
<220> FEATURE:
<223> OTHER INFORMATION: synthetic polynucleotide

<400> SEQUENCE: 8
cacattctta agcctgtgga acacctacat ctgtattaac gaagcgctaa ccgttttttat    60 caggctctgg gaggcagaat aaatgatcat atcgtcaatt attacctcca cggggagagc   120
ctgagcaaac tggcctcagg catttgagaa gcacacggtc acactgcttc cggtagtcaa   180
taaaccggta aaccagcaat agcataagc ggctatttaa cgaccctgcc ctgaaccgac    240 gacccgggtcg aatttgcttt cgaatttctg ccattcatcc gcttattatc acttattcag   300
gcgtagcaac caggcgttta agggcaccaa taactgcctt aaaaaaatta cgccccgccc   360
tgccactcat cgcagtactg ttgtaattca ttaagcattc tgccgacatg gaagccatca   420
caaacggcat gatgaacctg aatcgccagc ggcatcagca ccttgtcgcc ttgcgtataa   480
tatttgccca tggtgaaaac ggggggcgaag aagttgtcca tattggccac gtttaaatca   540
aaactggtga aactcaccca gggattggct gagacgaaaa acatattctc aataaaccct   600
ttagggaaat aggccaggtt ttcaccgtaa acgccacat cttgcgaata tatgtgtaga   660
aactgccgga atcgtcgtg gtattcactc cagagcgatg aaaacgtttc agtttgctca    720
tggaaaacgg tgtaacaagg gtgaacacta tcccatatca ccagctcacc gtctttcatt   780
gccatacgga attccggatg agcattcatc aggcgggcaa gaatgtgaat aaaggccgga   840
taaaacttgt gcttattttt ctttacggtc tttaaaaagg ccgtaatatc cagctgaacg   900
gtctggttat aggtacattg agcaactgac tgaaatgcct caaaatgttc tttacgatgc   960
cattgggata tatcaacggt ggtatatcca gtgattttt tctccatttt agcttcctta   1020
gctcctgaaa atctcgataa ctcaaaaaat acgcccggta gtgatcttat ttcattatgg   1080
tgaaagttgg aacctcttac gtgccgatca acgtctcatt ttcgccaaaa gttggcccag   1140
ggcttcccgg tatcaacagg acaccagga tttattatt ctgcgaagtg atcttccgtc    1200
acaggtattt attcggcgca aagtgcgtcg ggtgatgctg ccaacttact gatttagtgt   1260
atgatggtgt ttttgaggtg ctccagtggc ttctgtttct atcagctgtc cctcctgttc   1320
agctactgac ggggtggtgc gtaacggcaa agcaccgcc ggacatcagc gctagcggag    1380
tgtatactgg cttactatgt tggcactgat gagggtgtca gtgaagtgct tcatgtggca   1440
ggagaaaaaa ggctgcaccg gtgcgtcagc agaatatgtg atacaggata tattccgctt   1500
cctcgctcac tgactcgcta cgctcggtcg ttcgactgcg gcgagcggaa atggcttacg   1560 aacggggcg agatttcctg gaagatgcca ggaagatact aacagggaa gtgagagggc    1620 cgcggcaaag ccgtttttcc ataggctccg cccccctgac aagcatcacg aaatctgacg   1680
```

```
ctcaaatcag tggtggcgaa acccgacagg actataaaga taccaggcgt ttccccctgg   1740
cggctccctc gtgcgctctc ctgttcctgc ctttcggttt accggtgtca ttccgctgtt   1800
atggccgcgt ttgtctcatt ccacgcctga cactcagttc cgggtaggca gttcgctcca   1860
agctggactg tatgcacgaa ccccccgttc agtccgaccg ctgcgcctta ccggtaact    1920
atcgtcttga gtccaacccg gaaagacatg caaaagcacc actggcagca gccactggta   1980
attgatttag aggagttagt cttgaagtca tgcgccggtt aaggctaaac tgaaaggaca   2040
agttttggtg actgcgctcc tccaagccag ttacctcggt tcaaagagtt ggtagctcag   2100
agaaccttcg aaaaaccgcc ctgcaaggcg ttttttcgt tttcagagca agagattacg     2160
cgcagaccaa aacgatctca agaagatcat cttattaatc agataaaata tttctagatt   2220
tcagtgcaat ttatctcttc aaatgtagca cctgaagtca gccactagtc atatcgggga   2280
tctcgatccc gcgaaattaa tacgactcac tatagggaa ttgtgagcgg ataacaattc    2340
ccctctagaa ataattttgt taactttaa gaaggagata tacatatggc tagcaccatg    2400
gatatcaagc ttaccggtga attcgctatg acaaagatt gcgaaatgaa acgtaccacc    2460
ctggatagcc cgctgggcaa actggaactg agcggctgcg aacagggcct gcatgaaatt   2520
aaactgctgg gtaaaggcac cagcgcggcc gatgcggttg aagttccggc cccggccgcc   2580
gtgctgggtg tccggaacc gctgatgcag gcgaccgcgt ggctgaacgc gtattttcat    2640
cagccggaag cgattgaaga atttccggtt ccggcgctgc atcatccggt gtttcagcag   2700
gagagcttta cccgtcaggt gctgtggaaa ctgctgaaag tggttaaatt tggcgaagtg   2760
attagctatc agcagctggc ggccctggcg ggtaatccgg cggccaccgc cgccgttaaa   2820
accgcgctga gcgtaaccc ggtgccgatt ctgattccgt gccatcgtgt ggttagctct    2880
agcggtgcgg ttggcggtta tgaaggtggt ctggcggtga agagtggct gctggcccat    2940
gaaggtcatc gtctgggtaa accgggtctg gacctgcag tggataagaa atactcaata    3000
ggcttagata tcggcacaaa tagcgtcgga tgggcggtga tcactgatga atataaggtt   3060
ccgtctaaaa agttcaaggt tctgggaaat acagaccgcc acagtatcaa aaaaaatctt   3120
atagggctc ttttatttga cagtggagag acagcggaag cgactcgtct caaacggaca    3180
gctcgtagaa ggtatacacg tcggaagaat cgtatttgtt atctacagga gattttttca   3240
aatgagatgg cgaaagtaga tgatagtttc tttcatcgac ttgaagagtc ttttttggtg   3300
gaagaagaca agaagcatga acgtcatcct attttttggaa atatagtaga tgaagttgct   3360
tatcatgaga aatatccaac tatctatcat ctgcgaaaaa aattggtaga ttctactgat   3420
aaagcggatt tgcgcttaat ctatttggcc ttagcgcata tgattaagtt tcgtggtcat   3480
tttttgattg agggagattt aaatcctgat aatagtgatg tggacaaact atttatccag   3540
ttggtacaaa cctacaatca attatttgaa gaaaaccctta ttaacgcaag tggagtagat   3600
gctaaagcga ttctttctgc acgattgagt aaatcaagac gattagaaaa tctcattgct   3660
cagctccccg gtgagaagaa aaatggctta tttgggaatc tcattgcttt gtcattgggt   3720
ttgaccccta ttttaaatc aaattttgat ttggcagaag atgctaaatt acagctttca   3780
aaagatactt acgatgatga tttagataat ttattggcgc aaattggaga tcaatatgct   3840
gatttgtttt tggcagctaa gaatttatca gatgctattt tactttcaga tatcctaaga   3900
gtaaatactg aaataactaa ggctccccta tcagcttcaa tgattaaacg ctacgatgaa   3960
catcatcaag acttgactct ttttaaaagct ttagttcgac aacaacttcc agaaaagtat  4020
```

```
aaagaaatct tttttgatca atcaaaaaac ggatatgcag gttatattga tgggggagct    4080
agccaagaag aatttataaa atttatcaaa ccaattttag aaaaaatgga tggtactgag    4140
gaattattgg tgaaactaaa tcgtgaagat ttgctgcgca agcaacggac ctttgacaac    4200
ggctctattc cccatcaaat tcacttgggt gagctgcatg ctattttgag aagacaagaa    4260
gacttttatc cattttaaaa agacaatcgt gagaagattg aaaaaatctt gacttttcga    4320
attccttatt atgttggtcc attggcgcgt ggcaatagtc gttttgcatg gatgactcgg    4380
aagtctgaag aaacaattac cccatggaat tttgaagaag ttgtcgataa aggtgcttca    4440
gctcaatcat ttattgaacg catgacaaac tttgataaaa tcttccaaa tgaaaaagta    4500 ctaccaaaac atagtttgct ttatgagtat tttacggttt ataacgaatt gacaaaggtc    4560
aaatatgtta ctgaaggaat gcgaaaacca gcatttcttt caggtgaaca gaagaaagcc    4620
attgttgatt tactcttcaa aacaaatcga aaagtaaccg ttaagcaatt aaaagaagat    4680
tatttcaaaa aaatagaatg ttttgatagt gttgaaattt caggagttga agatagattt    4740
aatgcttcat taggtaccta ccatgatttg ctaaaaatta ttaaagataa agatttttg    4800 gataatgaag aaaatgaaga tatcttagag gatattgttt taacattgac cttatttgaa    4860
gatagggaga tgattgagga aagacttaaa acatatgctc acctctttga tgataaggtg    4920
atgaaacagc ttaaacgtcg ccgttatact ggttggggac gtttgtctcg aaaattgatt    4980
aatggtatta gggataagca atctggcaaa acaatattag atttttttgaa atcagatggt    5040 tttgccaatc gcaattttat gcagctgatc catgatgata gtttgacatt taaagaagac    5100
attcaaaaag cacaagtgtc tggacaaggc gatagtttac atgaacatat tgcaaattta    5160
gctggtagcc ctgctattaa aaaaggtatt ttacagactg taaaagttgt tgatgaattg    5220
gtcaaagtaa tggggcggca taagccagaa aatatcgtta ttgaaatggc acgtgaaaat    5280
cagacaactc aaaagggcca gaaaaattcg cgagagcgta tgaaacgaat cgaagaaggt    5340
atcaaagaat taggaagtca gattcttaaa gagcatcctg ttgaaaatac tcaattgcaa    5400
aatgaaaagc tctatctcta ttatctccaa aatggaagag acatgtatgt ggaccaagaa    5460
ttagatatta atcgtttaag tgattatgat gtcgatcaca ttgttccaca aagtttcctt    5520
aaagacgatt caatagacaa taaggtctta acgcgttctg ataaaaatcg tggtaaatcg    5580
gataacgttc caagtgaaga agtagtcaaa aagatgaaaa actattggag acaacttcta    5640
aacgccaagt taatcactca acgtaagttt gataatttaa cgaaagctga acgtggaggt    5700
ttgagtgaac ttgataaagc tggttttatc aaacgccaat tggttgaaac tcgccaaatc    5760
actaagcatg tggcacaaat tttggatagt cgcatgaata ctaaatacga tgaaaatgat    5820
aaacttattc gagaggttaa agtgattacc ttaaaatcta aattagtttc tgacttccga    5880
aaagatttcc aattctataa agtacgtgag attaacaatt accatcatgc ccatgatgcg    5940
tatctaaatg ccgtcgttgg aactgctttg attaagaaat atccaaaact gaatcggag    6000 tttgtctatg gtgattataa agtttatgat gttcgtaaaa tgattgctaa gtctgagcaa    6060
gaaataggca agcaaccgc aaaatatttc ttttactcta atatcatgaa cttcttcaaa    6120
acagaaatta cacttgcaaa tggagagatt cgcaaacgcc ctctaatcga aactaatggg    6180
gaaactggag aaattgtctg ggataaaggg cgagattttg ccacagtgcg caaagtattg    6240
tccatgcccc aagtcaatat tgtcaagaaa acagaagtac agacaggcgg attctccaag    6300
gagtcaattt taccaaaaag aaaattcgga caagcttattg ctcgtaaaaa agactggat    6360 ccaaaaaaat atggtggttt tgatagtcca acggtagctt attcagtcct agtggttgct    6420
```

```
aaggtggaaa aagggaaatc gaagaagtta aaatccgtta aagagttact agggatcaca    6480
attatggaaa gaagttcctt tgaaaaaaat ccgattgact ttttagaagc taaaggatat    6540
aaggaagtta aaaaagactt aatcattaaa ctacctaaat atagtctttt tgagttagaa    6600
aacggtcgta aacggatgct ggctagtgcc ggagaattac aaaaaggaaa tgagctggct    6660
ctgccaagca aatatgtgaa ttttttatat ttagctagtc attatgaaaa gttgaagggt    6720
agtccagaag ataacgaaca aaaacaattg tttgtggagc agcataagca ttatttagat    6780
gagattattg agcaaatcag tgaattttct aagcgtgtta ttttagcaga tgccaattta    6840
gataaagttc ttagtgcata taacaaacat agagacaaac caatacgtga acaagcagaa    6900
aatattattc atttatttac gttgacgaat cttggagctc ccgctgcttt taaatatttt    6960
gatacaacaa ttgatcgtaa acgatatacg tctacaaaag aagttttaga tgccactctt    7020
atccatcaat ccatcactgg tctttatgaa acacgcattg atttgagtca gctaggaggt    7080
gaccccaaga agaagaggaa ggtgatggat aagcatcacc accaccatca ctaactcgag    7140
gttaattaag cggccgcatt gatccggctg ctaacaaagc ccgaaaggaa gctgagttgg    7200
ctgctgccac cgctgagcaa taactagcat aaccccttgg ggcctctaaa cgggtcttga    7260
ggggttttt gctgaaagga ggaactatat ccggatgtag aggatcgaga tctcgatccc    7320
gcgaaattaa tacgactcac tatagggaa ttgtgagcgg ataacaattc ccctctagaa    7380
ataattttgt ttaactttaa gaaggagata tacatatgca tcatcatcat catcatattg    7440
acatgctagt tttacgatta ccgttcatcg attctcttgt ttgctccaga ctctcaggca    7500
atgacctgat agcctttgta gatctctcaa aaatagctac cctctccggc attaatttat    7560
cagctagaac ggttgaatat catattgatg gtgatttgac tgtctccggc ctttctcacc    7620
cttttgaatc tttacctaca cattactcag gcattgcatt taaaatatat gagggttcta    7680
aaaattttta tccttgcgtt gaaataaagg cttctcccgc aaaagtatta cagggtcata    7740
atgttttgg tacaaccgat ttagctttat gctctgaggc tttattgctt aattttgcta    7800
attctttgcc ttgcctgtat gatttattgg atgttaatgc tactactatt agtagaattg    7860
atgccacctt ttcagctcgc gccccaaatg aaaatatagc taaacaggtt attgaccatt    7920
tgcgaaatgt atctaatggt caaactaaat ctactcgttc gcagaattgg gaatcaactg    7980
ttatatggaa tgaaacttcc agacaccgta ctttagttgc atatttaaaa catgttgagc    8040
tacagcatta tattcagcaa ttaagctcta agccatccgc aaaaatgacc tcttatcaaa    8100
aggagcaatt aaaggtactc tctaatcctg acctgttgga gtttgcttcc ggtctggttc    8160
gctttgaagc tcgaattaaa acgcgatatt tgaagtcttt cgggcttcct cttaatcttt    8220
ttgatgcaat ccgctttgct tctgactata atagtcaggg taaagacctg attttttgatt    8280
tatggtcatt ctcgttttct gaactgttta aagcatttga ggggattca atgaatattt    8340
atgacgattc gcagtattg gacgctatcc agtctaaaca ttttactatt accccctctg    8400
gcaaaacttc ttttgcaaaa gcctctcgct attttggttt ttatcgtcgt ctggtaaacg    8460
agggttatga tagtgttgct cttactatgc ctcgtaattc cttttggcgt tatgtatctg    8520
cattagttga atgtggtatt cctaaatctc aactgatgaa tctttctacc tgtaataatg    8580
ttgttccgtt agttcgtttt attaacgtag attttttcttc ccaacgtcct gactggtata    8640
atgagccagt tcttaaaatc gcataaggta attcacaatg attaaagttg aaattaaacc    8700
atctcaagcc caatttacta ctcgttctgg tgtttctcgt cagggcaagc cttattcact    8760
```

-continued

```
gaatgagcag ctttgttacg ttgatttggg taatgaatat ccggttcttg tcaagattac    8820
tcttgatgaa ggtcagccag cctatgcgcc tggtctgtac accgttcatc tgtcctcttt    8880
caaagttggt cagttcggtt cccttatgat tgaccgtctg cgcctcgttc cggctaagca    8940
ccaccaccac caccactaat ctcgaggggtg gtggtagcga ttataaagat gatgatgata    9000
aaggcctgaa cgatatcttt gaagcccaga aaattgaatg gcacgagtaa aagcttgtcg    9060
agcaccacca ccaccaccac tgagatccgg ctgctaacaa agcccgaaag gaagctgagt    9120
tggctgctgc caccgctgag caataactag cataacccct tggggcctct aaacgggtct    9180
tgaggggttt tttgctgaaa ggaggaacta tatctaatac gactcactat agctggagaa    9240
ctgtaatgaa ccgtgagagg ctgagtgccg tgggcgccgc ctaacactgc caatgccggt    9300
cccaagcccg gataaaagtg gaggggcggg ggagccgttc gggcggctat aaacagacct    9360
caggcccgaa gcgtggcggc ttcggccgcc ggtggtacga tgcgttgagc taaccggtac    9420
aggggggctg ctcctagtac gagaggaccg gaggtaagcg cagccgccta acactgccaa    9480
tgccggtccc aagcccggat aaaagtggag ggggcgggga gccgttcggg cggctataaa    9540
cagacctcag gcccgaagcg tggcggcttc ggccgccggt ggtaacgacg ttgattttttt   9600 aggccggtg ttggacgcat cattttttctg gtgttcggaa gcatctaagt tttttcacgaa   9660 acttgccgcc taacactgcc aatgccggtc ccaagcccgg ataaaagtgg aggggcggg    9720 gagccgttcg gcggctata acagacctc aggcccgaag cgtggcggct tcggccgccg     9780
gtggtaaacg ttgaagacgc cccgagatga gttctccctg acccttttaac ttgagagaac   9840 tcgggtgaag gaacacaggt ggtcaggtag agaataccaa ggcggggtcc tgaaggtaat    9900
acgactcact atagactgcc cggtagctgg cacctcgatg tcggctcatc accgcccaag    9960
agttcatatc gacggcggtg tttaaatgcg gaagagataa gtgctgagtt gtcatgccaa   10020
tggcccgcct aacactgcca atgccggtcc caagcccgga taaaagtgga ggggcgggg   10080 agccgttcgg gcggctataa acagacctca ggcccgaagc gtggcggctt cggccgccg   10140 tggtacggcg gccgtaaaaa aactataacg gttaatccgg gttaaaagga gacaagaata   10200
aacgctcaat gattttgcag cacttcttgt tatcttaacg aactgttgat gattcgacag   10260
gaggctcaca acaggcaaaa gcggacagtg tgtgagacag ttaaaaacgg tccctatcgc   10320
gtgatgacga aaaaaggcac tacgccgcc taacactgcc aatgccggtc caagcccgg    10380 ataaaagtgg aggggcgggg agccgttcgg gcggctata acagacctc aggcccgaag   10440 cgtggcggct tcggccgccg gtggtatttg actgggcgc gagctgggtt tagaacgtcc   10500
tggtgggtag ccgcctaaca ctgccaatgc cggtcccaag cccggataaa agtggagggg   10560 gcgggagcc gttcggcgg ctataaacag acctcaggcc cgaagcgtgg cggcttcggc    10620
cgccggtggt ataaagagta acggaggagc acgcaagggt atggctgttc gccatttaaa   10680
gtggtacggt ctcctcctaa tacgactcac tatagcgagc aggtgctttt tgaaagcagg   10740
tctccgggga taatttttca ggctgataca tcctggggct tttttgaagt aggtccaagg   10800
ttggctattt ttatcctggt cggccgccta acactgccaa tgccggtccc aagcccggat   10860
aaaagtggag ggggcgggga gccgttcggg cggctataaa cagacctcag gcccgaagcg   10920
tggcggcttc ggccgccggt ggtatcgcgg atggagctga aattcgggag aaggcacgct   10980
gatatgtagg tgaccatcgc tcaacggata aaaggtacat agtgatccgg tggttctgaa   11040
tggaaggggg tccccgcct aacactgcca atgccggtcc caagcccgga taaaagtgga   11100 ggggcgggg agccgttcgg gcggctataa acagacctca ggcccgaagc gtggcggctt   11160
```

-continued

```
cggccgccgg tggtacgagc gtgacggcga catcaggagg ttagtgcaat ggcataagca    11220
tgtgtaggat aggtgggagg ctttctatag cttgacactg aacattgagc cttgcagctt    11280
gactgccgcc taacactgcc aatgccggtc ccaagcccgg ataaaagtgg aggggcggg     11340 gagccgttcg ggcggctata acagacctc aggcccgaag cgtggcggct cggccgccg      11400 gtggtagaaa ttccttgttg atgttctaac gttgacccgc ctaaggtagc taatacgact    11460
cactatagtc cgacctgcac gaatggcgta atggagccga ccttgaaata ccacccttta    11520
atgttcgggt aagtccgcct aacactgcca atgccggtcc caagcccgga taaaagtgga    11580
gggggcgggg agccgttcgg gcggctataa acagacctca ggcccgaagc gtggcggctt    11640
cggccgccgg tggtaggaaa gacccctttt tgtgaacctt tagaagtgtg gactttttgc    11700
cagtctgcat gatggccagg ttttttctgtc tccaccccgc ctaacactgc caatgccggt    11760
cccaagcccg gataaaagtg gaggggcggg ggagccgttc gggcggctat aaacagacct    11820
caggcccgaa gcgtggcggc ttcggccgcc ggtggtaagt gtacccgcgg caagaccgag    11880
actcagtgaa attgaactcg ctgtgacaaa cacgaaagtg gacgtatacg ggcaactgtt    11940
tattaaaaac acagcactgt gagatgcccg cctaacactg ccaatgccgg tcccaagccc    12000
ggataaaagt ggaggggcg gggagccgtt cgggcggcta taaacagacc tcaggcccga    12060
agcgtggcgg cttcggccgc cggtggtaca aatgccctgt cttgatcgaa gccccggtaa    12120
atgctgaagc aaccgcctaa cactgccaat gccggtccca agcccggata aaagtggagg    12180
gggcggggag ccgttcgggc ggctataaac agacctcagg cccgaagcgt ggcggcttcg    12240
gccgccggtg gtaagcctct aagcatcagg taacaaaggt taattgatgg ggttagcgca    12300
agcgaagcct tccaggaaac cgcctaacac tgccaatgcc ggtcccaagc ccggataaaa    12360
gtggaggggg cggggagccg ttcgggcggc tataaacaga cctcaggccc gaagcgtggc    12420
ggcttcggcc gccggtggta tcaaatcgta cttttttccca aaccgactag caaaatgtt    12480 tttgtgccgt aactcagtcg aagatttttt accagctggc ttgtgacgcc tgttttttccc    12540 ggtgccgg                                                              12548
```

<210> SEQ ID NO 9
<211> LENGTH: 286
<212> TYPE: PRT
<213> ORGANISM: Artificial Sequence
<220> FEATURE:
<223> OTHER INFORMATION: synthetic polypeptide

<400> SEQUENCE: 9

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110
```

```
Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 10
<211> LENGTH: 286
<212> TYPE: PRT
<213> ORGANISM: Artificial Sequence
<220> FEATURE:
<223> OTHER INFORMATION: synthetic polypeptide

<400> SEQUENCE: 10

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190
```

```
Thr Gly Glu Leu Leu Thr Leu Ala Ser Arg Gln Gln Leu Ile Asp Trp
        195                 200                 205

Met Glu Ala Asp Lys Val Ala Gly Pro Leu Met Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
                275                 280                 285

<210> SEQ ID NO 11
<211> LENGTH: 219
<212> TYPE: PRT
<213> ORGANISM: Artificial Sequence
<220> FEATURE:
<223> OTHER INFORMATION: synthetic polypeptide

<400> SEQUENCE: 11

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
            210                 215

<210> SEQ ID NO 12
<211> LENGTH: 1582
<212> TYPE: PRT
<213> ORGANISM: Artificial Sequence
<220> FEATURE:
<223> OTHER INFORMATION: synthetic polypeptide
```

```
<400> SEQUENCE: 12

Met Ala Ser Thr Met Asp Ile Lys Leu Thr Gly Glu Phe Ala Met Asp
1               5                   10                  15

Lys Asp Cys Glu Met Lys Arg Thr Thr Leu Asp Ser Pro Leu Gly Lys
            20                  25                  30

Leu Glu Leu Ser Gly Cys Glu Gln Gly Leu His Glu Ile Lys Leu Leu
        35                  40                  45

Gly Lys Gly Thr Ser Ala Ala Asp Ala Val Glu Val Pro Ala Pro Ala
    50                  55                  60

Ala Val Leu Gly Gly Pro Glu Pro Leu Met Gln Ala Thr Ala Trp Leu
65                  70                  75                  80

Asn Ala Tyr Phe His Gln Pro Glu Ala Ile Glu Glu Phe Pro Val Pro
                85                  90                  95

Ala Leu His His Pro Val Phe Gln Gln Glu Ser Phe Thr Arg Gln Val
            100                 105                 110

Leu Trp Lys Leu Leu Lys Val Val Lys Phe Gly Glu Val Ile Ser Tyr
        115                 120                 125

Gln Gln Leu Ala Ala Leu Ala Gly Asn Pro Ala Ala Thr Ala Ala Val
    130                 135                 140

Lys Thr Ala Leu Ser Gly Asn Pro Val Pro Ile Leu Ile Pro Cys His
145                 150                 155                 160

Arg Val Val Ser Ser Gly Ala Val Gly Gly Tyr Glu Gly Gly Leu
                165                 170                 175

Ala Val Lys Glu Trp Leu Leu Ala His Glu Gly His Arg Leu Gly Lys
            180                 185                 190

Pro Gly Leu Gly Pro Ala Val Asp Lys Lys Tyr Ser Ile Gly Leu Asp
        195                 200                 205

Ile Gly Thr Asn Ser Val Gly Trp Ala Val Ile Thr Asp Glu Tyr Lys
    210                 215                 220

Val Pro Ser Lys Lys Phe Lys Val Leu Gly Asn Thr Asp Arg His Ser
225                 230                 235                 240

Ile Lys Lys Asn Leu Ile Gly Ala Leu Leu Phe Asp Ser Gly Glu Thr
                245                 250                 255

Ala Glu Ala Thr Arg Leu Lys Arg Thr Ala Arg Arg Tyr Thr Arg
            260                 265                 270

Arg Lys Asn Arg Ile Cys Tyr Leu Gln Glu Ile Phe Ser Asn Glu Met
        275                 280                 285

Ala Lys Val Asp Asp Ser Phe Phe His Arg Leu Glu Glu Ser Phe Leu
    290                 295                 300

Val Glu Glu Asp Lys Lys His Glu Arg His Pro Ile Phe Gly Asn Ile
305                 310                 315                 320

Val Asp Glu Val Ala Tyr His Glu Lys Tyr Pro Thr Ile Tyr His Leu
                325                 330                 335

Arg Lys Lys Leu Val Asp Ser Thr Asp Lys Ala Asp Leu Arg Leu Ile
            340                 345                 350

Tyr Leu Ala Leu Ala His Met Ile Lys Phe Arg Gly His Phe Leu Ile
        355                 360                 365

Glu Gly Asp Leu Asn Pro Asp Asn Ser Asp Val Asp Lys Leu Phe Ile
    370                 375                 380

Gln Leu Val Gln Thr Tyr Asn Gln Leu Phe Glu Glu Asn Pro Ile Asn
385                 390                 395                 400

Ala Ser Gly Val Asp Ala Lys Ala Ile Leu Ser Ala Arg Leu Ser Lys
                405                 410                 415
```

```
Ser Arg Arg Leu Glu Asn Leu Ile Ala Gln Leu Pro Gly Glu Lys Lys
            420                 425                 430

Asn Gly Leu Phe Gly Asn Leu Ile Ala Leu Ser Leu Gly Leu Thr Pro
        435                 440                 445

Asn Phe Lys Ser Asn Phe Asp Leu Ala Glu Asp Ala Lys Leu Gln Leu
    450                 455                 460

Ser Lys Asp Thr Tyr Asp Asp Leu Asp Asn Leu Leu Ala Gln Ile
465                 470                 475                 480

Gly Asp Gln Tyr Ala Asp Leu Phe Leu Ala Ala Lys Asn Leu Ser Asp
                485                 490                 495

Ala Ile Leu Leu Ser Asp Ile Leu Arg Val Asn Thr Glu Ile Thr Lys
                500                 505                 510

Ala Pro Leu Ser Ala Ser Met Ile Lys Arg Tyr Asp Glu His His Gln
            515                 520                 525

Asp Leu Thr Leu Leu Lys Ala Leu Val Arg Gln Gln Leu Pro Glu Lys
    530                 535                 540

Tyr Lys Glu Ile Phe Phe Asp Gln Ser Lys Asn Gly Tyr Ala Gly Tyr
545                 550                 555                 560

Ile Asp Gly Gly Ala Ser Gln Glu Glu Phe Tyr Lys Phe Ile Lys Pro
                565                 570                 575

Ile Leu Glu Lys Met Asp Gly Thr Glu Glu Leu Leu Val Lys Leu Asn
            580                 585                 590

Arg Glu Asp Leu Leu Arg Lys Gln Arg Thr Phe Asp Asn Gly Ser Ile
                595                 600                 605

Pro His Gln Ile His Leu Gly Glu Leu His Ala Ile Leu Arg Arg Gln
    610                 615                 620

Glu Asp Phe Tyr Pro Phe Leu Lys Asp Asn Arg Glu Lys Ile Glu Lys
625                 630                 635                 640

Ile Leu Thr Phe Arg Ile Pro Tyr Tyr Val Gly Pro Leu Ala Arg Gly
                645                 650                 655

Asn Ser Arg Phe Ala Trp Met Thr Arg Lys Ser Glu Glu Thr Ile Thr
            660                 665                 670

Pro Trp Asn Phe Glu Glu Val Val Asp Lys Gly Ala Ser Ala Gln Ser
    675                 680                 685

Phe Ile Glu Arg Met Thr Asn Phe Asp Lys Asn Leu Pro Asn Glu Lys
690                 695                 700

Val Leu Pro Lys His Ser Leu Leu Tyr Glu Tyr Phe Thr Val Tyr Asn
705                 710                 715                 720

Glu Leu Thr Lys Val Lys Tyr Val Thr Glu Gly Met Arg Lys Pro Ala
                725                 730                 735

Phe Leu Ser Gly Glu Gln Lys Lys Ala Ile Val Asp Leu Leu Phe Lys
            740                 745                 750

Thr Asn Arg Lys Val Thr Val Lys Gln Leu Lys Glu Asp Tyr Phe Lys
    755                 760                 765

Lys Ile Glu Cys Phe Asp Ser Val Glu Ile Ser Gly Val Glu Asp Arg
770                 775                 780

Phe Asn Ala Ser Leu Gly Thr Tyr His Asp Leu Leu Lys Ile Ile Lys
785                 790                 795                 800

Asp Lys Asp Phe Leu Asp Asn Glu Glu Asn Glu Asp Ile Leu Glu Asp
                805                 810                 815

Ile Val Leu Thr Leu Thr Leu Phe Glu Asp Arg Glu Met Ile Glu Glu
            820                 825                 830
```

```
Arg Leu Lys Thr Tyr Ala His Leu Phe Asp Asp Lys Val Met Lys Gln
             835                 840                 845

Leu Lys Arg Arg Tyr Thr Gly Trp Gly Arg Leu Ser Arg Lys Leu
850                 855                 860

Ile Asn Gly Ile Arg Asp Lys Gln Ser Gly Lys Thr Ile Leu Asp Phe
865                 870                 875                 880

Leu Lys Ser Asp Gly Phe Ala Asn Arg Asn Phe Met Gln Leu Ile His
             885                 890                 895

Asp Asp Ser Leu Thr Phe Lys Glu Asp Ile Gln Lys Ala Gln Val Ser
             900                 905                 910

Gly Gln Gly Asp Ser Leu His Glu His Ile Ala Asn Leu Ala Gly Ser
             915                 920                 925

Pro Ala Ile Lys Lys Gly Ile Leu Gln Thr Val Lys Val Val Asp Glu
930                 935                 940

Leu Val Lys Val Met Gly Arg His Lys Pro Glu Asn Ile Val Ile Glu
945                 950                 955                 960

Met Ala Arg Glu Asn Gln Thr Thr Gln Lys Gly Gln Lys Asn Ser Arg
                 965                 970                 975

Glu Arg Met Lys Arg Ile Glu Glu Gly Ile Lys Glu Leu Gly Ser Gln
             980                 985                 990

Ile Leu Lys Glu His Pro Val Glu Asn Thr Gln Leu Gln Asn Glu Lys
             995                 1000                1005

Leu Tyr Leu Tyr Tyr Leu Gln Asn Gly Arg Asp Met Tyr Val Asp
1010                1015                1020

Gln Glu Leu Asp Ile Asn Arg Leu Ser Asp Tyr Asp Val Asp His
1025                1030                1035

Ile Val Pro Gln Ser Phe Leu Lys Asp Asp Ser Ile Asp Asn Lys
1040                1045                1050

Val Leu Thr Arg Ser Asp Lys Asn Arg Gly Lys Ser Asp Asn Val
1055                1060                1065

Pro Ser Glu Glu Val Val Lys Lys Met Lys Asn Tyr Trp Arg Gln
1070                1075                1080

Leu Leu Asn Ala Lys Leu Ile Thr Gln Arg Lys Phe Asp Asn Leu
1085                1090                1095

Thr Lys Ala Glu Arg Gly Gly Leu Ser Glu Leu Asp Lys Ala Gly
1100                1105                1110

Phe Ile Lys Arg Gln Leu Val Glu Thr Arg Gln Ile Thr Lys His
1115                1120                1125

Val Ala Gln Ile Leu Asp Ser Arg Met Asn Thr Lys Tyr Asp Glu
1130                1135                1140

Asn Asp Lys Leu Ile Arg Glu Val Lys Val Ile Thr Leu Lys Ser
1145                1150                1155

Lys Leu Val Ser Asp Phe Arg Lys Asp Phe Gln Phe Tyr Lys Val
1160                1165                1170

Arg Glu Ile Asn Asn Tyr His His Ala His Asp Ala Tyr Leu Asn
1175                1180                1185

Ala Val Val Gly Thr Ala Leu Ile Lys Lys Tyr Pro Lys Leu Glu
1190                1195                1200

Ser Glu Phe Val Tyr Gly Asp Tyr Lys Val Tyr Asp Val Arg Lys
1205                1210                1215

Met Ile Ala Lys Ser Glu Gln Glu Ile Gly Lys Ala Thr Ala Lys
1220                1225                1230

Tyr Phe Phe Tyr Ser Asn Ile Met Asn Phe Phe Lys Thr Glu Ile
```

```
                    1235                1240                1245

Thr Leu Ala Asn Gly Glu Ile Arg Lys Arg Pro Leu Ile Glu Thr
            1250                1255                1260

Asn Gly Glu Thr Gly Glu Ile Val Trp Asp Lys Gly Arg Asp Phe
        1265                1270                1275

Ala Thr Val Arg Lys Val Leu Ser Met Pro Gln Val Asn Ile Val
    1280                1285                1290

Lys Lys Thr Glu Val Gln Thr Gly Gly Phe Ser Lys Glu Ser Ile
1295                1300                1305

Leu Pro Lys Arg Asn Ser Asp Lys Leu Ile Ala Arg Lys Lys Asp
    1310                1315                1320

Trp Asp Pro Lys Lys Tyr Gly Gly Phe Asp Ser Pro Thr Val Ala
        1325                1330                1335

Tyr Ser Val Leu Val Val Ala Lys Val Glu Lys Gly Lys Ser Lys
            1340                1345                1350

Lys Leu Lys Ser Val Lys Glu Leu Leu Gly Ile Thr Ile Met Glu
                1355                1360                1365

Arg Ser Ser Phe Glu Lys Asn Pro Ile Asp Phe Leu Glu Ala Lys
                    1370                1375                1380

Gly Tyr Lys Glu Val Lys Lys Asp Leu Ile Ile Lys Leu Pro Lys
                        1385                1390                1395

Tyr Ser Leu Phe Glu Leu Glu Asn Gly Arg Lys Arg Met Leu Ala
                    1400                1405                1410

Ser Ala Gly Glu Leu Gln Lys Gly Asn Glu Leu Ala Leu Pro Ser
                1415                1420                1425

Lys Tyr Val Asn Phe Leu Tyr Leu Ala Ser His Tyr Glu Lys Leu
            1430                1435                1440

Lys Gly Ser Pro Glu Asp Asn Glu Gln Lys Gln Leu Phe Val Glu
        1445                1450                1455

Gln His Lys His Tyr Leu Asp Glu Ile Ile Glu Gln Ile Ser Glu
    1460                1465                1470

Phe Ser Lys Arg Val Ile Leu Ala Asp Ala Asn Leu Asp Lys Val
1475                1480                1485

Leu Ser Ala Tyr Asn Lys His Arg Asp Lys Pro Ile Arg Glu Gln
    1490                1495                1500

Ala Glu Asn Ile Ile His Leu Phe Thr Leu Thr Asn Leu Gly Ala
        1505                1510                1515

Pro Ala Ala Phe Lys Tyr Phe Asp Thr Thr Ile Asp Arg Lys Arg
            1520                1525                1530

Tyr Thr Ser Thr Lys Glu Val Leu Asp Ala Thr Leu Ile His Gln
                1535                1540                1545

Ser Ile Thr Gly Leu Tyr Glu Thr Arg Ile Asp Leu Ser Gln Leu
                    1550                1555                1560

Gly Gly Asp Pro Lys Lys Lys Arg Lys Val Met Asp Lys His His
                        1565                1570                1575

His His His His
    1580

<210> SEQ ID NO 13
<211> LENGTH: 7
<212> TYPE: PRT
<213> ORGANISM: Artificial Sequence
<220> FEATURE:
<223> OTHER INFORMATION: synthetic polypeptide
```

<400> SEQUENCE: 13

Pro Lys Lys Lys Arg Lys Val
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 14

His His His His His His
1               5

<210> SEQ ID NO 15
<211> LENGTH: 409
<212> TYPE: PRT
<213> ORGANISM: Artificial Sequence
<220> FEATURE:
<223> OTHER INFORMATION: synthetic polypeptide

<400> SEQUENCE: 15

Ile Asp Met Leu Val Leu Arg Leu Pro Phe Ile Asp Ser Leu Val Cys
1               5                   10                  15

Ser Arg Leu Ser Gly Asn Asp Leu Ile Ala Phe Val Asp Leu Ser Lys
            20                  25                  30

Ile Ala Thr Leu Ser Gly Ile Asn Leu Ser Ala Arg Thr Val Glu Tyr
        35                  40                  45

His Ile Asp Gly Asp Leu Thr Val Ser Gly Leu Ser His Pro Phe Glu
    50                  55                  60

Ser Leu Pro Thr His Tyr Ser Gly Ile Ala Phe Lys Ile Tyr Glu Gly
65                  70                  75                  80

Ser Lys Asn Phe Tyr Pro Cys Val Glu Ile Lys Ala Ser Pro Ala Lys
                85                  90                  95

Val Leu Gln Gly His Asn Val Phe Gly Thr Thr Asp Leu Ala Leu Cys
            100                 105                 110

Ser Glu Ala Leu Leu Asn Phe Ala Asn Ser Leu Pro Cys Leu Tyr
        115                 120                 125

Asp Leu Leu Asp Val Asn Ala Thr Thr Ile Ser Arg Ile Asp Ala Thr
130                 135                 140

Phe Ser Ala Arg Ala Pro Asn Glu Asn Ile Ala Lys Gln Val Ile Asp
145                 150                 155                 160

His Leu Arg Asn Val Ser Asn Gly Gln Thr Lys Ser Thr Arg Ser Gln
                165                 170                 175

Asn Trp Glu Ser Thr Val Ile Trp Asn Glu Thr Ser Arg His Arg Thr
            180                 185                 190

Leu Val Ala Tyr Leu Lys His Val Glu Leu Gln His Tyr Ile Gln Gln
        195                 200                 205

Leu Ser Ser Lys Pro Ser Ala Lys Met Thr Ser Tyr Gln Lys Glu Gln
    210                 215                 220

Leu Lys Val Leu Ser Asn Pro Asp Leu Leu Glu Phe Ala Ser Gly Leu
225                 230                 235                 240

Val Arg Phe Glu Ala Arg Ile Lys Thr Arg Tyr Leu Lys Ser Phe Gly
                245                 250                 255

Leu Pro Leu Asn Leu Phe Asp Ala Ile Arg Phe Ala Ser Asp Tyr Asn
            260                 265                 270

```
Ser Gln Gly Lys Asp Leu Ile Phe Asp Leu Trp Ser Phe Ser Phe Ser
            275                 280                 285

Glu Leu Phe Lys Ala Phe Glu Gly Asp Ser Met Asn Ile Tyr Asp Asp
        290                 295                 300

Ser Ala Val Leu Asp Ala Ile Gln Ser Lys His Phe Thr Ile Thr Pro
305                 310                 315                 320

Ser Gly Lys Thr Ser Phe Ala Lys Ala Ser Arg Tyr Phe Gly Phe Tyr
                325                 330                 335

Arg Arg Leu Val Asn Glu Gly Tyr Asp Ser Val Ala Leu Thr Met Pro
            340                 345                 350

Arg Asn Ser Phe Trp Arg Tyr Val Ser Ala Leu Val Glu Cys Gly Ile
        355                 360                 365

Pro Lys Ser Gln Leu Met Asn Leu Ser Thr Cys Asn Asn Val Val Pro
    370                 375                 380

Leu Val Arg Phe Ile Asn Val Asp Phe Ser Ser Gln Arg Pro Asp Trp
385                 390                 395                 400

Tyr Asn Glu Pro Val Leu Lys Ile Ala
                405

<210> SEQ ID NO 16
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 16

Met Asn Ile Tyr Asp Asp Ser Ala Val Leu Asp Ala Ile Gln Ser Lys
1               5                   10                  15

His Phe Thr Ile Thr Pro Ser Gly Lys Thr Ser Phe Ala Lys Ala Ser
            20                  25                  30

Arg Tyr Phe Gly Phe Tyr Arg Arg Leu Val Asn Glu Gly Tyr Asp Ser
        35                  40                  45

Val Ala Leu Thr Met Pro Arg Asn Ser Phe Trp Arg Tyr Val Ser Ala
    50                  55                  60

Leu Val Glu Cys Gly Ile Pro Lys Ser Gln Leu Met Asn Leu Ser Thr
65                  70                  75                  80

Cys Asn Asn Val Val Pro Leu Val Arg Phe Ile Asn Val Asp Phe Ser
                85                  90                  95

Ser Gln Arg Pro Asp Trp Tyr Asn Glu Pro Val Leu Lys Ile Ala
            100                 105                 110

<210> SEQ ID NO 17
<211> LENGTH: 87
<212> TYPE: PRT
<213> ORGANISM: Artificial Sequence
<220> FEATURE:
<223> OTHER INFORMATION: synthetic polypeptide

<400> SEQUENCE: 17

Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60
```

Leu Ser Ser Phe Lys Val Gly Gln Phe Gly Ser Leu Met Ile Asp Arg
65                  70                  75                  80

Leu Arg Leu Val Pro Ala Lys
            85

<210> SEQ ID NO 18
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 18
tctcaacagc gttttgtaa gatcctaaca tgggggattt ttcatgtaa ct         52

<210> SEQ ID NO 19
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 19
tttttctaaa agtgggttac atcgaactgg actatttgtt ta             42

<210> SEQ ID NO 20
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 20
gccccgaaga gagctaaccg cttttttgca ctgagagttt tc             42

<210> SEQ ID NO 21
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 21
acgttttcca aggaccgaag                                      20

<210> SEQ ID NO 22
<211> LENGTH: 78
<212> TYPE: DNA
<213> ORGANISM: Artificial Sequence
<220> FEATURE:
<223> OTHER INFORMATION: synthetic polynucleotide

<400> SEQUENCE: 22
gtaagagaat ttttttatgc agtgctctta cttctgattt ttcaacgatc ggatgatgag   60
cacttttttt ttaaagtt                                        78

<210> SEQ ID NO 23
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 23
tctgcgctgg cggataaagt tgcaacggat g                                   31

<210> SEQ ID NO 24
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 24
gcatgacaac agaaaagcat cttggaccac t                                   31

<210> SEQ ID NO 25
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 25
caacgttgcg ctttttaaac tattaagaca gatcgctttt ttgagatagg tg            52

<210> SEQ ID NO 26
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 26
gcggccaagc cataaccatg agtgctgtag c                                   31

<210> SEQ ID NO 27
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 27
aatggcaagt gacaccacga tgcataacac t                                   31

<210> SEQ ID NO 28
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 28
atctcatgac cgctacaggg cgccactttt ccctttttga ta                       42

<210> SEQ ID NO 29
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 29
caaaatccct cttaaagcgc                                                20

<210> SEQ ID NO 30
<211> LENGTH: 52
<212> TYPE: DNA
<213> ORGANISM: Artificial Sequence

```
<220> FEATURE:
<223> OTHER INFORMATION: synthetic polynucleotide

<400> SEQUENCE: 30
taaaaggatc ttttttaggt gaagatgggg aaatgtgttt tcgcggaac cc         52

<210> SEQ ID NO 31
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 31
ttgggaaccg tttaaaactt catttttaat tcgccttgat cg                   42

<210> SEQ ID NO 32
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 32
gagctgaatg tttagattga                                            20

<210> SEQ ID NO 33
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 33
accaagttta cttttttcat atatacaagc cataccattt ttaacgacga gc         52

<210> SEQ ID NO 34
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 34
ttaaattttg agcgtcagac cccaattggt a                               31

<210> SEQ ID NO 35
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 35
actgtcagcc tcactgatta agcaattcgc g                               31

<210> SEQ ID NO 36
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 36
acaattaata gtttttactg gatggacggc ccttccgttt ttgctggctg gt         52
```

<210> SEQ ID NO 37
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 37
cttactctag caactatgga tgaacgaaat actggcgaac ta        42

<210> SEQ ID NO 38
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 38
cttcccggca gggagtcagg        20

<210> SEQ ID NO 39
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 39
gacgccgggc attttagag caactcttgg ttgagtattt ttctcaccag tc        52

<210> SEQ ID NO 40
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 40
taaaagatgc tttttgaag atcagttatg tatccgcttt tttcatgaga ca        52

<210> SEQ ID NO 41
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 41
ggtgaaagtg tttttgctca cccagtatta t        31

<210> SEQ ID NO 42
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 42
cccgtattct gctatgtggc gcggaaacgc t        31

<210> SEQ ID NO 43
<211> LENGTH: 31
<212> TYPE: DNA
<213> ORGANISM: Artificial Sequence
<220> FEATURE:
<223> OTHER INFORMATION: synthetic polynucleotide

```
<400> SEQUENCE: 43
gcccccgaca ctaaatcgga accccgccct t                                  31

<210> SEQ ID NO 44
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 44 attcccttc aacatttccg tgttaaaggg a                                   31

<210> SEQ ID NO 45
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 45
aaaaaggaag atttttgtat gagtatttt gcggcatttt ttttttgcctt cc           52

<210> SEQ ID NO 46
<211> LENGTH: 78
<212> TYPE: DNA
<213> ORGANISM: Artificial Sequence
<220> FEATURE:
<223> OTHER INFORMATION: synthetic polynucleotide

<400> SEQUENCE: 46
gtaaccacca cttttaccc gccgcgtaac gtgagttttt ttttcgttcc acttgttaaa    60
tcatttttgc tcattttt                                                 78

<210> SEQ ID NO 47
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 47
cgctgcgcgg gcgctggcaa gtgtgcttca a                                  31

<210> SEQ ID NO 48
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 48
taatattgat aaccctgata aatagcggtc a                                  31

<210> SEQ ID NO 49
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 49
aacaagagtc ctttttacta ttaaagcgtc tatcaggttt ttgcgatggc cc           52
```

```
<210> SEQ ID NO 50
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 50
tgagtgttgt tggcgagaaa ggaagggaag acgagatagg gt                42

<210> SEQ ID NO 51
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 51
tccagtttgg ccggcgaacg                                         20

<210> SEQ ID NO 52
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 52
tggggtcgag gtttttttgcc gtaaagttta gagcttgttt ttacggggaa ag    52

<210> SEQ ID NO 53
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 53
aagtttttac tacgtgaacc atcatattct c                            31

<210> SEQ ID NO 54
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 54
agaatgacgg tcgccgcata caccectaat c                            31

<210> SEQ ID NO 55
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 55
ttataaatca attttttaaga atagacaagc gaaaggattt tgcgggcgc ta     52

<210> SEQ ID NO 56
<211> LENGTH: 31
<212> TYPE: DNA
<213> ORGANISM: Artificial Sequence
<220> FEATURE:
<223> OTHER INFORMATION: synthetic polynucleotide
```

<400> SEQUENCE: 56
cctcccgtca gcactggggc cagaaatcgg c					31

<210> SEQ ID NO 57
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 57
aaaatcccta accaataggc cgatggtaag c					31

<210> SEQ ID NO 58
<211> LENGTH: 52
<212> TYPE: DNA
<213> ORGANISM: Artificial Sequence
<220> FEATURE:
<223> OTHER INFORMATION: synthetic polynucleotide

<400> SEQUENCE: 58
gtgggtctcg cttttggta tcattgatcg tagttatttt ttctacacga cg					52

<210> SEQ ID NO 59
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 59
cgaaaaacaa cgtggactcc aacgctggag c					31

<210> SEQ ID NO 60
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 60
cggtgagctt attgctgata aattcaaagg g					31

<210> SEQ ID NO 61
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 61
tacattcaaa tgggtgcacg					20

<210> SEQ ID NO 62
<211> LENGTH: 499
<212> TYPE: DNA
<213> ORGANISM: Artificial Sequence
<220> FEATURE:
<223> OTHER INFORMATION: synthetic polynucleotide

<400> SEQUENCE: 62
ctaatacgac tcactataga cgactggagc agtaatgccg ttttagagct agaaatagca					60 agttaaaata aggctagtcc gttatcaact tgaaaaagtg gcaccgagtc ggtgcaaaaa					120

```
tccgacctgc acgaatggcg taatggagcc gaccttgaaa taccacccct taatgttcgg      180
gtaagtaaca ctgccaatgc cggtcccaag cccggataaa agtggagggc ttacactcgt      240
ttgagcgagt ataaacagcg ccgtaggctc aaagcggaga gcagattcgt ctgctctcgc      300
ggcggccgta aaaaactat aacggttaat ccgggttaaa aggagacaag aataaacgct      360
caatgatttt gcagcacttc ttgttatctt aacgaactgt tgatgattcg acaggaggct      420
cacaacaggc aaaagcggac agtgtgtgag acagttaaaa acggtcccta tcgcgtgatg      480
acgaaaaaag gcactacgg                                                   499

<210> SEQ ID NO 63
<211> LENGTH: 257
<212> TYPE: DNA
<213> ORGANISM: Artificial Sequence
<220> FEATURE:
<223> OTHER INFORMATION: synthetic polynucleotide

<400> SEQUENCE: 63
ctaatacgac tcactatagg aaagacccct ttttgtgaac ctttagaagt gtggactttt       60
tgccagtctg catgatggcc aggttttttct gtctccacct aacactgcca atgccggtcc     120
caagcccgga taaagtgga gggggtggac tcgtttgagc gagtataaac agatttctag       180
gctcaaagcg gagagcagat tcgtctgctc tcggaaattc cttgttgatg ttctaacgtt      240
gacccgccta aggtagc                                                    257

<210> SEQ ID NO 64
<211> LENGTH: 1185
<212> TYPE: DNA
<213> ORGANISM: Artificial Sequence
<220> FEATURE:
<223> OTHER INFORMATION: synthetic polynucleotide

<400> SEQUENCE: 64
gaattcgcgg ccgcttctag agctaatacg actcactata gacgactgga gcagtaatgc       60
cgttttagag ctagaaatag caagttaaaa taaggctagt ccgttatcaa cttgaaaaag      120
tggcaccgag tcggtgcaaa atccgacct gcacgaatgg cgtaatggag ccgaccttga       180
ataccacccc tttaatgttc gggtaagtaa cactgccaat gccggtccca agcccggata      240
aaagtggagg gcttacactc gtttgagcga gtataaacag cgccgtaggc tcaaagcgga      300
gagcagattc gtctgctctc gcggcggccg taaaaaaact ataacggtta atccgggtta      360
aaaggagaca agaataaacg ctcaatgatt ttgcagcact tcttgttatc ttaacgaact      420
gttgatgatt cgacaggagg ctcacaacag gcaaaagcgg acagtgtgtg agacagttaa      480
aaacggtccc tatcgcgtga tgacgaaaaa aggcactacg gtaacactgc caatgccggt      540
cccaagcccg gataaaagtg gagggccgta tatctgttag ttttttttcta ctagactgct      600 aacaaagccc gaaaggaagc tgagttggct gctgccaccg ctgagcaata actagcataa      660
ccccttgggg cctctaaacg ggtcttgagg ggttttttgc tgaaaggagg aactctaata      720
cgactcacta taggaaagac ccctttttgt gaacctttag aagtgtggac ttttgccag      780 tctgcatgat ggccaggttt ttctgtctcc acctaacact gccaatgccg gtcccaagcc      840
cggataaaag tggagggggt ggactcgttt gagcgagtat aaacagattt ctaggctcaa      900
agcggagagc agattcgtct gctctcggaa attccttgtt gatgttctaa cgttgacccg      960
cctaaggtag ctaacactgc caatgccggt cccaagcccg dataaaagtg gaggggctac     1020
tatctgttag ttttttttcta ctagactgct aacaaagccc gaaaggaagc tgagttggct     1080
```

```
gctgccaccg ctgagcaata actagcataa cccttgggg cctctaaacg ggtcttgagg    1140 ggtttttgc tgaaaggagg aacttactag tagcggccgc tgcag                    1185
```